US012758632B2

(12) United States Patent
Snook et al.

(10) Patent No.: US 12,758,632 B2
(45) Date of Patent: Oct. 13, 2026

(54) DESMOGLEIN 2-DIRECTED CHIMERIC ANTIGEN RECEPTOR (CAR) CONSTRUCTS AND METHODS OF USE

(71) Applicant: Thomas Jefferson University, Philadelphia, PA (US)

(72) Inventors: Adam Eugene Snook, Aston, PA (US); My Georgia Mahoney, Yardley, PA (US); Robert Devlin Carlson, Sewell, NJ (US)

(73) Assignee: Thomas Jefferson University, Philadelphia, PA (US)

(*) Notice: Subject to any disclaimer, the term of this patent is extended or adjusted under 35 U.S.C. 154(b) by 663 days.

(21) Appl. No.: 18/255,633

(22) PCT Filed: Dec. 2, 2021

(86) PCT No.: PCT/US2021/061548
§ 371 (c)(1),
(2) Date: Jun. 2, 2023

(87) PCT Pub. No.: WO2022/120010
PCT Pub. Date: Jun. 9, 2022

(65) Prior Publication Data
US 2024/0108651 A1 Apr. 4, 2024

Related U.S. Application Data

(60) Provisional application No. 63/120,356, filed on Dec. 2, 2020.

(51) Int. Cl.
*A61P 35/00* (2006.01)
*A61K 40/11* (2025.01)
(Continued)

(52) U.S. Cl.
CPC .......... *A61K 40/4202* (2025.01); *A61K 40/11* (2025.01); *A61K 40/15* (2025.01);
(Continued)

(58) Field of Classification Search
CPC .... A61K 40/4202; A61K 40/11; A61K 40/15; A61K 40/31; A61K 40/4254;
(Continued)

(56) References Cited

U.S. PATENT DOCUMENTS 8,067,547 B2 * 11/2011 Ewert .................... A61P 27/02 530/387.3
11,242,398 B2 * 2/2022 Calzone ............ C07K 16/2878
(Continued)

FOREIGN PATENT DOCUMENTS

| | | | |
|---|---|---|---|
| WO | 2015121454 | 8/2015 | |
| WO | WO-2015121454 A1 * | 8/2015 | C07K 14/705 |
| WO | 2019152660 | 8/2019 | |

OTHER PUBLICATIONS

Harrison OJ, Brasch J, Lasso G, et al. Structural basis of adhesive binding by desmocollins and desmogleins. Proc Natl Acad Sci U S A. 2016;113(26):7160-7165. (Year: 2016).*
(Continued)

*Primary Examiner* — Joanne Hama
*Assistant Examiner* — Hannah Sunshine
(74) *Attorney, Agent, or Firm* — Riverside Law LLP

(57) ABSTRACT

The present disclosure relates to Dsg2 binding molecules, nucleic acid molecules encoding the Dsg2 binding molecules and compositions comprising the same and methods of use thereof for treating or preventing cancer.

21 Claims, 22 Drawing Sheets

Specification includes a Sequence Listing.

(51) Int. Cl.
*A61K 40/15* (2025.01)
*A61K 40/31* (2025.01)
*A61K 40/42* (2025.01)
*A61K 40/50* (2025.01)
*C07K 16/28* (2006.01)
*C12N 5/0783* (2010.01)

(52) U.S. Cl.
CPC .......... *A61K 40/31* (2025.01); *A61K 40/4254* (2025.01); *A61P 35/00* (2018.01); *C07K 16/28* (2013.01); *C12N 5/0636* (2013.01); *A61K 40/50* (2025.01); *A61K 2239/13* (2023.05); *A61K 2239/38* (2023.05)

(58) Field of Classification Search
CPC ................ A61K 40/50; A61K 2239/13; A61K 2239/38; A61K 2039/505; A61P 35/00; C07K 16/28; C07K 2317/33; C07K 2317/622; C07K 2319/03; C07K 14/7051; C07K 2319/02; C12N 5/0636; C12N 2510/00; C12N 5/0646
See application file for complete search history.

(56) References Cited

U.S. PATENT DOCUMENTS

2015/0284448 A1 10/2015 Weiner
2016/0053318 A1 2/2016 Bonder
2018/0371052 A1 12/2018 Ma
2019/0300604 A1* 10/2019 Chen ...................... A61P 35/00

OTHER PUBLICATIONS

Müller S, Bexte T, Gebel V, et al. High Cytotoxic Efficiency of Lentivirally and Alpharetrovirally Engineered CD19-Specific Chimeric Antigen Receptor Natural Killer Cells Against Acute Lymphoblastic Leukemia. Front Immunol. 2020;10:3123. (Year: 2020).*

Cancer risk and prevention. American Cancer Society. Accessed Mar. 21, 2025. https://www.cancer.org/cancer/risk-prevention.html. Internet; Wayback Machine (Year: 2025).*

Herold EM, John C, Weber B, et al. Determinants of the assembly and function of antibody variable domains. Sci Rep. 2017;7(1):12276. (Year: 2017).*

Hummer AM, Abanades B, Deane CM. Advances in computational structure-based antibody design. Curr Opin Struct Biol. 2022;74:102379. (Year: 2022).*

Koenig P, Lee CV, Walters BT, et al. Mutational landscape of antibody variable domains reveals a switch modulating the interdomain conformational dynamics and antigen binding. Proc Natl Acad Sci U S A. 2017;114(4):E486-E495. (Year: 2017).*

Rabia LA, Desai AA, Jhaj HS, Tessier PM. Understanding and overcoming trade-offs between antibody affinity, specificity, stability and solubility. Biochem Eng J. Sep. 15, 2018;137:365-374. (Year: 2018).*

Wagner HJ, Wehrle S, Weiss E, Cavallari M, Weber W. A Two-Step Approach for the Design and Generation of Nanobodies. Int J Mol Sci. Nov. 2, 2018;19(11):3444. (Year: 2018).*

Zabetakis D, Anderson GP, Bayya N, Goldman ER. Contributions of the complementarity determining regions to the thermal stability of a single-domain antibody. PLoS One. 2013;8(10):e77678. (Year: 2013).*

Aas-Hanssen, K et al., "Mus musculus isolate LNVH-21-669 immunoglobulin heavy chain variable region mRNA, partial cds", nucleotide, (May 21, 2015), Database accession No. KJ144113.1, URL: ncbi, XP055941581.

Barber et al., "Characterization of desmoglein expression in the normal prostatic gland. Desmoglein 2 is an independent prognostic factor for aggressive prostate cancer," PLoS One. Jun. 4, 2014;9(6):e98786.

Baybutt et al., "Advances in Chimeric Antigen Receptor T-Cell Therapies for Solid Tumors," Clin Pharmacol Ther. Jan. 2019;105(1):71-78.

Biedermann et al., "Desmoglein 2 is expressed abnormally rather than mutated in familial and sporadic gastric cancer," J Pathol. Oct. 2005;207(2):199-206.

Brennan et al., "A role for caveolin-1 in desmoglein binding and desmosome dynamics," Oncogene. Mar. 29, 2012;31(13):1636-48.

Brennan et al., "Increased expression of Dsg2 in malignant skin carcinomas: A tissue-microarray based study," Cell Adh Migr. Apr.-Jun. 2009;3(2):148-54.

Brennan et al., "Suprabasal Dsg2 expression in transgenic mouse skin confers a hyperproliferative and apoptosis-resistant phenotype to keratinocytes," J Cell Sci. Mar. 1, 2007;120(Pt 5):758-71.

Brennan-Crispi et al., "Crosstalk between Desmoglein 2 and Patched 1 accelerates chemical-induced skin tumorigenesis," Oncotarget. Apr. 20, 2015;6(11):8593-605.

Brennan-Crispi et al., "Overexpression of Desmoglein 2 in a Mouse Model of Gorlin Syndrome Enhances Spontaneous Basal Cell Carcinoma Formation through STAT3-Mediated Gli1 Expression," J Invest Dermatol. Feb. 2019;139(2):300-307.

Brudno et al., "Chimeric antigen receptor T-cell therapies for lymphoma," Nat Rev Clin Oncol. Jan. 2018;15(1):31-46.

Carrillo, J et al., "Monoclonal autoantibody light chain variable region, partial", Protein, (Jul. 26, 2016), Database accession No. ACB48035, URL: ncbi, XP055941573.

Castellarin et al., "A rational mouse model to detect on-target, off-tumor Car T cell toxicity," JCI Insight. Jul. 23, 2020;5(14):e136012.

Ellebrecht et al., "Synthetic construct Dsg3 EC 1-4 CAAR gene, complete cds", Nucleotide, (Jul. 19, 2016), Database accession No. KX348140, URL: NCBI, XP055941585.

Eshkind et al., "Loss of desmoglein 2 suggests essential functions for early embryonic development and proliferation of embryonal stem cells," Eur J Cell Biol. Nov. 2002;81(11):592-8.

Gupta et al. "Cell cycle- and cancer-associated gene networks activated by Dsg2: evidence of cystatin A deregulation and a potential role in cell-cell adhesion," PLoS One. Mar. 18, 2015;10(3):e0120091.

Hay et al., "Kinetics and biomarkers of severe cytokine release syndrome after CD19 chimeric antigen receptor- modified T-cell therapy," Blood. Nov. 23, 2017;130(21):2295-2306.

Kamekura et al., "Loss of the desmosomal cadherin desmoglein-2 suppresses colon cancer cell proliferation through EGFR signaling," Oncogene. Sep. 4, 2014;33(36):4531-6.

Kant et al., "Desmoglein 2-Dependent Arrhythmogenic Cardiomyopathy Is Caused by a Loss of Adhesive Function," Circ Cardiovasc Genet. Aug. 2015;8(4):553-63.

Kochenderfer et al., "Construction and preclinical evaluation of an anti-CD19 chimeric antigen receptor," J Immunother. Sep. 2009;32(7):689-702.

Kowalczyk et al., "Structure, function, and regulation of desmosomes," Prog Mol Biol Transl Sci. 2013:116:95-118.

Lombardi et al., "Arrhythmogenic right ventricular cardiomyopathy is a disease of cardiac stem cells," Curr Opin Cardiol. May 2010;25(3):222-8.

Magee et al. "GUCY2C-directed CAR-T cells oppose colorectal cancer metastases without autoimmunity," Oncoimmunology. Sep. 2, 2016;5(10):e1227897.

Magee et al. "Human GUCY2C-Targeted Chimeric Antigen Receptor (CAR)-Expressing T Cells Eliminate Colorectal Cancer Metastases," Cancer Immunol Res. May 2018;6(5):509-516.

Morgan et al., "Case report of a serious adverse event following the administration of T cells transduced with a chimeric antigen receptor recognizing ERBB2," Mol Ther. Apr. 2010;18(4):843-51.

Najor, "Desmosomes in Human Disease," Annu Rev Pathol. Jan. 24, 2018:13:51-70.

Overmiller et al., "c-Src/Cav1-dependent activation of the EGFR by Dsg2," Oncotarget. Jun. 21, 2016;7(25):37536-37555.

Park et al., "DSG2 Is a Functional Cell Surface Marker for Identification and Isolation of Human Pluripotent Stem Cells," Stem Cell Reports. Jul. 10, 2018;11(1):115-127.

(56) References Cited

OTHER PUBLICATIONS

Rufener, GA et al., "1 F5-NQ-28-BB-z-2A-trCD19 [synthetic construct]", Protein, (May 31, 2016), Database accession No. ANG83989, URL: ncbi, XP055941576.
Sewell, et al. "Challenges and opportunities for the future of monoclonal antibody development: Improving safety assessment and reducing animal use," MAbs. Jul. 2017;9(5):742-755.
Tan et al. "Desmoglein 2 promotes vasculogenic mimicry in melanoma and is associated with poor clinical outcome," Oncotarget. Jul. 19, 2016;7(29):46492-46508.
Wahl, "Generation of monoclonal antibodies specific for desmoglein family members," Hybrid Hybridomics. Feb. 2002;21(1):37-44.
Wang et al. "Desmoglein 2 is a receptor for adenovirus serotypes 3, 7, 11 and 14," Nat Med. Jan. 2011;17(1):96-104.
Wang et al., "A new human DSG2-transgenic mouse model for studying the tropism and pathology of human adenoviruses," J Virol. Jun. 2012;86(11):6286-302.
Yang et al., "T cells expressing NKG2D chimeric antigen receptors efficiently eliminate glioblastoma and cancer stem cells," J Immunother Cancer. Jul. 9, 2019;7(1):171.

* cited by examiner

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Chemically Synthesized, 6D8 Antibody HC CDR1

<400> SEQUENCE: 1

ggctacacgt tcaccaacta cggt                                       24


<210> SEQ ID NO 2
<211> LENGTH: 8
<212> TYPE: PRT
<213> ORGANISM: Artificial Sequence
<220> FEATURE:
<223> OTHER INFORMATION: Chemically Synthesized, 6D8 Antibody HC CDR1

<400> SEQUENCE: 2

Gly Tyr Thr Phe Thr Asn Tyr Gly
1               5


<210> SEQ ID NO 3
<211> LENGTH: 24
<212> TYPE: DNA
<213> ORGANISM: Artificial Sequence
<220> FEATURE:
<223> OTHER INFORMATION: Chemically Synthesized, 6D8 Antibody HC CDR2

<400> SEQUENCE: 3

atcaatactt acaccggtaa tcca                                       24


<210> SEQ ID NO 4
<211> LENGTH: 8
<212> TYPE: PRT
<213> ORGANISM: Artificial Sequence
<220> FEATURE:
<223> OTHER INFORMATION: Chemically Synthesized, 6D8 Antibody HC CDR2
```

<400> SEQUENCE: 4

Ile Asn Thr Tyr Thr Gly Asn Pro
1 5

<210> SEQ ID NO 5
<211> LENGTH: 30
<212> TYPE: DNA
<213> ORGANISM: Artificial Sequence
<220> FEATURE:
<223> OTHER INFORMATION: Chemically Synthesized, 6D8 Antibody HC CDR3

<400> SEQUENCE: 5
gctcgcgaca ggggcaactc cttcgactat 30

<210> SEQ ID NO 6
<211> LENGTH: 10
<212> TYPE: PRT
<213> ORGANISM: Artificial Sequence
<220> FEATURE:
<223> OTHER INFORMATION: Chemically Synthesized, 6D8 Antibody HC CDR3

<400> SEQUENCE: 6

Ala Arg Asp Arg Gly Asn Ser Phe Asp Tyr
1 5 10

<210> SEQ ID NO 7
<211> LENGTH: 351
<212> TYPE: DNA
<213> ORGANISM: Artificial Sequence
<220> FEATURE:
<223> OTHER INFORMATION: Chemically Synthesized, 6D8 Antibody HC

<400> SEQUENCE: 7
cagatccagc ttgtgcagag cggccccgag ctgaagaagc ccggggagac tgtcaagatc 60
tcttgcaagg cgtccggcta cacgttcacc aactacggta tgaactgggt gaagcaggcc 120
ccggggcgtg gcttgaaatg gatgggttgg atcaatactt acaccggtaa tccaacctac 180
gcggatgact tcaagggccg cttcgatttt tcgctggaga cctccgctag cactgcctac 240
ctgcaaatta acaacctcaa aaacgaggac atggccatct atttctgtgc tcgcgacagg 300
ggcaactcct tcgactattg gggccagggt accacactga ccgtctcttc t 351

<210> SEQ ID NO 8
<211> LENGTH: 117
<212> TYPE: PRT
<213> ORGANISM: Artificial Sequence
<220> FEATURE:
<223> OTHER INFORMATION: Chemically Synthesized, 6D8 Antibody HC

<400> SEQUENCE: 8

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Arg Gly Leu Lys Trp Met
35 40 45

Gly Trp Ile Asn Thr Tyr Thr Gly Asn Pro Thr Tyr Ala Asp Asp Phe
50 55 60

Lys Gly Arg Phe Asp Phe Ser Leu Glu Thr Ser Ala Ser Thr Ala Tyr
65 70 75 80

Leu Gln Ile Asn Asn Leu Lys Asn Glu Asp Met Ala Ile Tyr Phe Cys

```
                85                  90                  95

Ala Arg Asp Arg Gly Asn Ser Phe Asp Tyr Trp Gly Gln Gly Thr Thr
            100                 105                 110

Leu Thr Val Ser Ser
        115


<210> SEQ ID NO 9
<211> LENGTH: 18
<212> TYPE: DNA
<213> ORGANISM: Artificial Sequence
<220> FEATURE:
<223> OTHER INFORMATION: Chemically Synthesized, 6D8 Antibody LC CDR1

<400> SEQUENCE: 9

gagaacatct actcgaac                                                    18


<210> SEQ ID NO 10
<211> LENGTH: 6
<212> TYPE: PRT
<213> ORGANISM: Artificial Sequence
<220> FEATURE:
<223> OTHER INFORMATION: Chemically Synthesized, 6D8 Antibody LC CDR1

<400> SEQUENCE: 10

Glu Asn Ile Tyr Ser Asn
1               5


<210> SEQ ID NO 11
<211> LENGTH: 9
<212> TYPE: DNA
<213> ORGANISM: Artificial Sequence
<220> FEATURE:
<223> OTHER INFORMATION: Chemically Synthesized, 6D8 Antibody LC CDR2

<400> SEQUENCE: 11

atcgccatt                                                               9


<210> SEQ ID NO 12
<211> LENGTH: 3
<212> TYPE: PRT
<213> ORGANISM: Artificial Sequence
<220> FEATURE:
<223> OTHER INFORMATION: Chemically Synthesized, 6D8 Antibody LC CDR2

<400> SEQUENCE: 12

Ile Ala Ile
1


<210> SEQ ID NO 13
<211> LENGTH: 27
<212> TYPE: DNA
<213> ORGANISM: Artificial Sequence
<220> FEATURE:
<223> OTHER INFORMATION: Chemically Synthesized, 6D8 Antibody LC CDR3

<400> SEQUENCE: 13

cagcactttt ggggcactcc gcgcacc                                          27


<210> SEQ ID NO 14
<211> LENGTH: 9
<212> TYPE: PRT
<213> ORGANISM: Artificial Sequence
<220> FEATURE:
<223> OTHER INFORMATION: Chemically Synthesized, 6D8 Antibody LC CDR3

<400> SEQUENCE: 14
```

```
Gln His Phe Trp Gly Thr Pro Arg Thr
1               5


<210> SEQ ID NO 15
<211> LENGTH: 321
<212> TYPE: DNA
<213> ORGANISM: Artificial Sequence
<220> FEATURE:
<223> OTHER INFORMATION: Chemically Synthesized, 6D8 Antibody LC

<400> SEQUENCE: 15

gacatccaga tgacccagag ccctgctagt ctctccgtgt ccgttggcga gacggtgacc      60

atcacctgcc gcgcatccga gaacatctac tcgaacctgg cctggtacca gcagaagcag     120

ggcaagagcc ctcagctgct ggtgtacatc gccattaacc tggcggacgg cgtaccctct     180

cggttttcag ggagcggctc ggggacccag tacagtctaa aaattaattc ccttcagtcc     240

gaagatttcg gcaactatta ctgtcagcac ttttggggca ctccgcgcac cttcggcgga     300

ggtaccaagc tggagatcaa g                                               321


<210> SEQ ID NO 16
<211> LENGTH: 107
<212> TYPE: PRT
<213> ORGANISM: Artificial Sequence
<220> FEATURE:
<223> OTHER INFORMATION: Chemically Synthesized, 6D8 Antibody LC

<400> SEQUENCE: 16

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ile Ala Ile Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asn Tyr Tyr Cys Gln His Phe Trp Gly Thr Pro Arg
                85                  90                  95

Thr Phe Gly Gly Gly Thr Lys Leu Glu Ile Lys
            100                 105


<210> SEQ ID NO 17
<211> LENGTH: 15
<212> TYPE: DNA
<213> ORGANISM: Artificial Sequence
<220> FEATURE:
<223> OTHER INFORMATION: Chemically Synthesized, 10D2 Antibody HC CDR1

<400> SEQUENCE: 17

agctacatct tgcat                                                       15


<210> SEQ ID NO 18
<211> LENGTH: 5
<212> TYPE: PRT
<213> ORGANISM: Artificial Sequence
<220> FEATURE:
<223> OTHER INFORMATION: Chemically Synthesized, 10D2 Antibody HC CDR1

<400> SEQUENCE: 18
```

Ser Tyr Ile Leu His
1 5

<210> SEQ ID NO 19
<211> LENGTH: 51
<212> TYPE: DNA
<213> ORGANISM: Artificial Sequence
<220> FEATURE:
<223> OTHER INFORMATION: Chemically Synthesized, 10D2 Antibody HC CDR2

<400> SEQUENCE: 19
tatattaacc cgtacaacga cgccaccaag tacaacgaga aatttaaggg c 51

<210> SEQ ID NO 20
<211> LENGTH: 17
<212> TYPE: PRT
<213> ORGANISM: Artificial Sequence
<220> FEATURE:
<223> OTHER INFORMATION: Chemically Synthesized, 10D2 Antibody HC CDR2

<400> SEQUENCE: 20

Tyr Ile Asn Pro Tyr Asn Asp Ala Thr Lys Tyr Asn Glu Lys Phe Lys
1 5 10 15

Gly

<210> SEQ ID NO 21
<211> LENGTH: 14
<212> TYPE: DNA
<213> ORGANISM: Artificial Sequence
<220> FEATURE:
<223> OTHER INFORMATION: Chemically Synthesized, 10D2 Antibody HC CDR3

<400> SEQUENCE: 21
acaccacagc ctat 14

<210> SEQ ID NO 22
<211> LENGTH: 5
<212> TYPE: PRT
<213> ORGANISM: Artificial Sequence
<220> FEATURE:
<223> OTHER INFORMATION: Chemically Synthesized, 10D2 Antibody HC CDR3

<400> SEQUENCE: 22

Ile Thr Thr Ala Tyr
1 5

<210> SEQ ID NO 23
<211> LENGTH: 354
<212> TYPE: DNA
<213> ORGANISM: Artificial Sequence
<220> FEATURE:
<223> OTHER INFORMATION: Chemically Synthesized, 10D2 Antibody HC

<400> SEQUENCE: 23
gaggtgcagc tgcagcagag cgggcccgag ctggtgaatc caggcgcgtc agtgaagatg 60
tcatgcaaag cttctggcta ctccttcacc agctacatct tgcattgggt caagcagaag 120
cctggacagg gtctggagtg gatcggttat attaacccgt acaacgacgc caccaagtac 180
aacgagaaat ttaagggcaa ggccacgctc actagcgata aaagctcgtc cacggcctac 240
atggaattga gttccgtcac ctccgaggac agcgcggtgt actactgttg ctctatgatc 300
accacagcct attgggcgta ctggggccag ggcactcttg ttacagtatc tgct 354

<210> SEQ ID NO 24

```
<211> LENGTH: 118
<212> TYPE: PRT
<213> ORGANISM: Artificial Sequence
<220> FEATURE:
<223> OTHER INFORMATION: Chemically Synthesized, 10D2 Antibody HC

<400> SEQUENCE: 24

Glu Val Gln Leu Gln Gln Ser Gly Pro Glu Leu Val Asn Pro Gly Ala
1               5                   10                  15

Ser Val Lys Met Ser Cys Lys Ala Ser Gly Tyr Ser Phe Thr Ser Tyr
            20                  25                  30

Ile Leu His Trp Val Lys Gln Lys Pro Gly Gln Gly Leu Glu Trp Ile
        35                  40                  45

Gly Tyr Ile Asn Pro Tyr Asn Asp Ala Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Val Thr Ser Glu Asp Ser Ala Val Tyr Tyr Cys
                85                  90                  95

Cys Ser Met Ile Thr Thr Ala Tyr Trp Ala Tyr Trp Gly Gln Gly Thr
            100                 105                 110

Leu Val Thr Val Ser Ala
        115


<210> SEQ ID NO 25
<211> LENGTH: 51
<212> TYPE: DNA
<213> ORGANISM: Artificial Sequence
<220> FEATURE:
<223> OTHER INFORMATION: Chemically Synthesized, 10D2 Antibody LC CDR1

<400> SEQUENCE: 25

aaatcctctc aatctatcct gtacggctcg acccagaaga actacctggc a              51


<210> SEQ ID NO 26
<211> LENGTH: 17
<212> TYPE: PRT
<213> ORGANISM: Artificial Sequence
<220> FEATURE:
<223> OTHER INFORMATION: Chemically Synthesized, 10D2 Antibody LC CDR1

<400> SEQUENCE: 26

Lys Ser Ser Gln Ser Ile Leu Tyr Gly Ser Thr Gln Lys Asn Tyr Leu
1               5                   10                  15

Ala


<210> SEQ ID NO 27
<211> LENGTH: 21
<212> TYPE: DNA
<213> ORGANISM: Artificial Sequence
<220> FEATURE:
<223> OTHER INFORMATION: Chemically Synthesized, 10D2 Antibody LC CDR2

<400> SEQUENCE: 27

tgggcttcca ctcgtgagag c                                               21


<210> SEQ ID NO 28
<211> LENGTH: 7
<212> TYPE: PRT
<213> ORGANISM: Artificial Sequence
<220> FEATURE:
<223> OTHER INFORMATION: Chemically Synthesized, 10D2 Antibody LC CDR2
```

<400> SEQUENCE: 28

Trp Ala Ser Thr Arg Glu Ser
1 5

<210> SEQ ID NO 29
<211> LENGTH: 24
<212> TYPE: DNA
<213> ORGANISM: Artificial Sequence
<220> FEATURE:
<223> OTHER INFORMATION: Chemically Synthesized, 10D2 Antibody LC CDR3

<400> SEQUENCE: 29
caccagtacc tttcgagcta cacc 24

<210> SEQ ID NO 30
<211> LENGTH: 8
<212> TYPE: PRT
<213> ORGANISM: Artificial Sequence
<220> FEATURE:
<223> OTHER INFORMATION: Chemically Synthesized, 10D2 Antibody LC CDR3

<400> SEQUENCE: 30

His Gln Tyr Leu Ser Ser Tyr Thr
1 5

<210> SEQ ID NO 31
<211> LENGTH: 336
<212> TYPE: DNA
<213> ORGANISM: Artificial Sequence
<220> FEATURE:
<223> OTHER INFORMATION: Chemically Synthesized, 10D2 Antibody LC

<400> SEQUENCE: 31
aacatcatga tgacccagag cccgtcgtcc ctcaccgtgt ccgctggcga gaaggtgacc 60
atgtcttgca aatcctctca atctatcctg tacggctcga cccagaagaa ctacctggca 120
tggtaccagc agaagcccgg gcagagccct aagctgctga tttattgggc ttccactcgt 180
gagagcgggg tccccgaccg cttcaccggc tccggctccg gcaccgactt caccctgacc 240
atctcttccg tgcaggccga agatctggcc gtgtattact gtcaccagta cctttcgagc 300
tacaccttcg gcggtggcac taagttagag atcaag 336

<210> SEQ ID NO 32
<211> LENGTH: 112
<212> TYPE: PRT
<213> ORGANISM: Artificial Sequence
<220> FEATURE:
<223> OTHER INFORMATION: Chemically Synthesized, 10D2 Antibody LC

<400> SEQUENCE: 32

Asn Ile Met Met Thr Gln Ser Pro Ser Ser Leu Thr Val Ser Ala Gly
1 5 10 15

Glu Lys Val Thr Met Ser Cys Lys Ser Ser Gln Ser Ile Leu Tyr Gly
20 25 30

Ser Thr Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys His Gln
85 90 95

```
Tyr Leu Ser Ser Tyr Thr Phe Gly Gly Gly Thr Lys Leu Glu Ile Lys
            100                 105                 110


<210> SEQ ID NO 33
<211> LENGTH: 1593
<212> TYPE: DNA
<213> ORGANISM: Artificial Sequence
<220> FEATURE:
<223> OTHER INFORMATION: Chemically Synthesized, 6D8-28BBz_CAR

<400> SEQUENCE: 33

atggcattgc ctgttacagc tctgctgctg cccctggctc tgcttctgca tgctgccaga     60

cctgacatcc agatgaccca gagccctgct agtctctccg tgtccgttgg cgagacggtg    120

accatcacct gccgcgcatc cgagaacatc tactcgaacc tggcctggta ccagcagaag    180

cagggcaaga gccctcagct gctggtgtac atcgccatta acctggcgga cggcgtaccc    240

tctcggtttt cagggagcgg ctcggggacc cagtacagtc taaaaattaa ttcccttcag    300

tccgaagatt tcggcaacta ttactgtcag cacttttggg gcactccgcg caccttcggc    360

ggaggtacca agctggagat caagtcgggc ggaggaggca gcggcggcgg gggttccggt    420

ggaggcggct ctggcggcgg gggttctcag atccagcttg tgcagagcgg ccccgagctg    480

aagaagcccg gggagactgt caagatctct tgcaaggcgt ccggctacac gttcaccaac    540

tacggtatga actgggtgaa gcaggccccg gggcgtggct tgaaatggat gggttggatc    600

aatacttaca ccggtaatcc aacctacgcg gatgacttca agggccgctt cgatttttcg    660

ctggagacct ccgctagcac tgcctacctg caaattaaca acctcaaaaa cgaggacatg    720

gccatctatt tctgtgctcg cgacaggggc aactccttcg actattgggg ccagggtacc    780

acactgaccg tctcttctac aacaacccct gctcctcggc ctcctacacc agctcctaca    840

attgccagcc agcctctgtc tctgaggccc gaagcttgta gacctgctgc tggcggagcc    900

gtgcatacaa gaggactgga tttcgcctgc gacatctaca tctgggctcc tctggccgga    960

acatgtggcg tgctgctgct gagcctggtc atcaccctgt actgccggtc caagagaagc   1020

agactgctgc acagcgacta catgaacatg acccctagac ggcccggacc taccagaaag   1080

cactaccagc cttacgctcc tcctcgggac ttcgctgcct acagaagcaa gcggggcaga   1140

aagaagctgc tgtacatctt caagcagccc ttcatgcggc ccgtgcagac cacacaagag   1200

gaagatggct gctcctgcag attccccgag gaagaagaag gcggctgcga gctgagagtg   1260

aagttcagca gatccgctga cgcccctgcc tacaagcagg gacagaacca gctgtacaac   1320

gagctgaacc tggggagaag agaagagtac gacgtgctgg acaagcggag aggcagagat   1380

cctgagatgg gcggcaagcc cagacggaag aatcctcaag agggcctgta taatgagctg   1440

cagaaagaca agatggccga ggcctacagc gagatcggaa tgaagggcga gcgcagaaga   1500

ggcaagggac acgatggact gtaccagggc ctgagcaccg ccaccaagga tacctatgat   1560

gccctgcaca tgcaggccct gcctccaaga tag                                1593


<210> SEQ ID NO 34
<211> LENGTH: 530
<212> TYPE: PRT
<213> ORGANISM: Artificial Sequence
<220> FEATURE:
<223> OTHER INFORMATION: Chemically Synthesized, 6D8-28BBz_CAR

<400> SEQUENCE: 34

Met Ala Leu Pro Val Thr Ala Leu Leu Leu Pro Leu Ala Leu Leu Leu
```

-continued

```
1               5                   10                  15

His Ala Ala Arg Pro Asp Ile Gln Met Thr Gln Ser Pro Ala Ser Leu
            20                  25                  30

Ser Val Ser Val Gly Glu Thr Val Thr Ile Thr Cys Arg Ala Ser Glu
        35                  40                  45

Asn Ile Tyr Ser Asn Leu Ala Trp Tyr Gln Gln Lys Gln Gly Lys Ser
    50                  55                  60

Pro Gln Leu Leu Val Tyr Ile Ala Ile Asn Leu Ala Asp Gly Val Pro
65                  70                  75                  80

Ser Arg Phe Ser Gly Ser Gly Ser Gly Thr Gln Tyr Ser Leu Lys Ile
                85                  90                  95

Asn Ser Leu Gln Ser Glu Asp Phe Gly Asn Tyr Tyr Cys Gln His Phe
            100                 105                 110

Trp Gly Thr Pro Arg Thr Phe Gly Gly Gly Thr Lys Leu Glu Ile Lys
        115                 120                 125

Ser Gly Gly Gly Gly Ser Gly Gly Gly Gly Ser Gly Gly Gly Gly Ser
    130                 135                 140

Gly Gly Gly Gly Ser Gln Ile Gln Leu Val Gln Ser Gly Pro Glu Leu
145                 150                 155                 160

Lys Lys Pro Gly Glu Thr Val Lys Ile Ser Cys Lys Ala Ser Gly Tyr
                165                 170                 175

Thr Phe Thr Asn Tyr Gly Met Asn Trp Val Lys Gln Ala Pro Gly Arg
            180                 185                 190

Gly Leu Lys Trp Met Gly Trp Ile Asn Thr Tyr Thr Gly Asn Pro Thr
        195                 200                 205

Tyr Ala Asp Asp Phe Lys Gly Arg Phe Asp Phe Ser Leu Glu Thr Ser
    210                 215                 220

Ala Ser Thr Ala Tyr Leu Gln Ile Asn Asn Leu Lys Asn Glu Asp Met
225                 230                 235                 240

Ala Ile Tyr Phe Cys Ala Arg Asp Arg Gly Asn Ser Phe Asp Tyr Trp
                245                 250                 255

Gly Gln Gly Thr Thr Leu Thr Val Ser Ser Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Lys
            420                 425                 430
```

```
Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
        515                 520                 525

Pro Arg
    530


<210> SEQ ID NO 35
<211> LENGTH: 1611
<212> TYPE: DNA
<213> ORGANISM: Artificial Sequence
<220> FEATURE:
<223> OTHER INFORMATION: Chemically Synthesized, 10D2-28BBz_CAR

<400> SEQUENCE: 35

atggcattgc ctgttacagc tctgctgctg cccctggctc tgcttctgca tgctgccaga     60

cctaacatca tgatgaccca gagcccgtcg tccctcaccg tgtccgctgg cgagaaggtg    120

accatgtctt gcaaatcctc tcaatctatc ctgtacggct cgacccagaa gaactacctg    180

gcatggtacc agcagaagcc cgggcagagc cctaagctgc tgatttattg ggcttccact    240

cgtgagagcg gggtccccga ccgcttcacc ggctccggct ccggcaccga cttcaccctg    300

accatctctt ccgtgcaggc cgaagatctg gccgtgtatt actgtcacca gtacctttcg    360

agctacacct tcggcggtgg cactaagtta gagatcaagt cgggcggggg aggaagtggc    420

gggggtggtt ctggcggcgg tggttccggc ggaggagggt ccgaggtgca gctgcagcag    480

agcgggcccg agctggtgaa tccaggcgcg tcagtgaaga tgtcatgcaa agcttctggc    540

tactccttca ccagctacat cttgcattgg gtcaagcaga agcctggaca gggtctggag    600

tggatcggtt atattaaccc gtacaacgac gccaccaagt acaacgagaa atttaagggc    660

aaggccacgc tcactagcga taaaagctcg tccacggcct acatggaatt gagttccgtc    720

acctccgagg acagcgcggt gtactactgt tgctctatga tcaccacagc ctattgggcg    780

tactggggcc agggcactct tgttacagta tctgctacaa caacccctgc tcctcggcct    840

cctacaccag ctcctacaat tgccagccag cctctgtctc tgaggcccga agcttgtaga    900

cctgctgctg gcggagccgt gcatacaaga ggactggatt tcgcctgcga catctacatc    960

tgggctcctc tggccggaac atgtggcgtg ctgctgctga gcctggtcat caccctgtac   1020

tgccggtcca agagaagcag actgctgcac agcgactaca tgaacatgac ccctagacgg   1080

cccggaccta ccagaaagca ctaccagcct tacgctcctc ctcgggactt cgctgcctac   1140

agaagcaagc ggggcagaaa gaagctgctg tacatcttca agcagccctt catgcggccc   1200

gtgcagacca cacaagagga agatggctgc tcctgcagat tccccgagga agaagaaggc   1260

ggctgcgagc tgagagtgaa gttcagcaga tccgctgacg cccctgccta caagcaggga   1320

cagaaccagc tgtacaacga gctgaacctg gggagaagag aagagtacga cgtgctggac   1380

aagcggagag gcagagatcc tgagatgggc ggcaagccca gacggaagaa tcctcaagag   1440
```

```
ggcctgtata atgagctgca gaaagacaag atggccgagg cctacagcga gatcggaatg   1500

aagggcgagc gcagaagagg caagggacac gatggactgt accagggcct gagcaccgcc   1560

accaaggata cctatgatgc cctgcacatg caggccctgc ctccaagata g            1611


<210> SEQ ID NO 36
<211> LENGTH: 536
<212> TYPE: PRT
<213> ORGANISM: Artificial Sequence
<220> FEATURE:
<223> OTHER INFORMATION: Chemically Synthesized, 10D2-28BBz_CAR

<400> SEQUENCE: 36

Met Ala Leu Pro Val Thr Ala Leu Leu Leu Pro Leu Ala Leu Leu Leu
1               5                   10                  15

His Ala Ala Arg Pro Asn Ile Met Met Thr Gln Ser Pro Ser Ser Leu
            20                  25                  30

Thr Val Ser Ala Gly Glu Lys Val Thr Met Ser Cys Lys Ser Ser Gln
        35                  40                  45

Ser Ile Leu Tyr Gly Ser Thr Gln Lys Asn Tyr Leu Ala Trp Tyr Gln
    50                  55                  60

Gln Lys Pro Gly Gln Ser Pro Lys Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Ala Glu Asp Leu Ala Val
            100                 105                 110

Tyr Tyr Cys His Gln Tyr Leu Ser Ser Tyr Thr Phe Gly Gly Gly Thr
        115                 120                 125

Lys Leu Glu Ile Lys Ser Gly Gly Gly Gly Ser Gly Gly Gly Gly Ser
    130                 135                 140

Gly Gly Gly Gly Ser Gly Gly Gly Gly Ser Glu Val Gln Leu Gln Gln
145                 150                 155                 160

Ser Gly Pro Glu Leu Val Asn Pro Gly Ala Ser Val Lys Met Ser Cys
                165                 170                 175

Lys Ala Ser Gly Tyr Ser Phe Thr Ser Tyr Ile Leu His Trp Val Lys
            180                 185                 190

Gln Lys Pro Gly Gln Gly Leu Glu Trp Ile Gly Tyr Ile Asn Pro Tyr
        195                 200                 205

Asn Asp Ala Thr Lys Tyr Asn Glu Lys Phe Lys Gly Lys Ala Thr Leu
    210                 215                 220

Thr Ser Asp Lys Ser Ser Ser Thr Ala Tyr Met Glu Leu Ser Ser Val
225                 230                 235                 240

Thr Ser Glu Asp Ser Ala Val Tyr Tyr Cys Cys Ser Met Ile Thr Thr
                245                 250                 255

Ala Tyr Trp Ala Tyr Trp Gly Gln Gly Thr Leu Val Thr Val Ser Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335
```

-continued

```
Ile Thr Leu Tyr Cys Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Lys Arg
    370                 375                 380

Gly Arg Lys Lys Leu Leu Tyr Ile Phe Lys Gln Pro Phe Met Arg Pro
385                 390                 395                 400

Val Gln Thr Thr Gln Glu Glu Asp Gly Cys Ser Cys Arg Phe Pro Glu
                405                 410                 415

Glu Glu Glu Gly Gly Cys Glu Leu Arg Val Lys Phe Ser Arg Ser Ala
            420                 425                 430

Asp Ala Pro Ala Tyr Lys Gln Gly Gln Asn Gln Leu Tyr Asn Glu Leu
        435                 440                 445

Asn Leu Gly Arg Arg Glu Glu Tyr Asp Val Leu Asp Lys Arg Arg Gly
    450                 455                 460

Arg Asp Pro Glu Met Gly Gly Lys Pro Arg Arg Lys Asn Pro Gln Glu
465                 470                 475                 480

Gly Leu Tyr Asn Glu Leu Gln Lys Asp Lys Met Ala Glu Ala Tyr Ser
                485                 490                 495

Glu Ile Gly Met Lys Gly Glu Arg Arg Arg Gly Lys Gly His Asp Gly
            500                 505                 510

Leu Tyr Gln Gly Leu Ser Thr Ala Thr Lys Asp Thr Tyr Asp Ala Leu
        515                 520                 525

His Met Gln Ala Leu Pro Pro Arg
    530                 535
```

DESMOGLEIN 2-DIRECTED CHIMERIC ANTIGEN RECEPTOR (CAR) CONSTRUCTS AND METHODS OF USE

CROSS REFERENCE TO RELATED APPLICATIONS

This application is the U.S. national phase application filed under 35 U.S.C. § 371 claiming benefit to International Patent Application No. PCT/US21/61548, filed Dec. 2, 2021, which is entitled to priority under 35 U.S.C. § 119(e) to 63/120,356, filed Dec. 2, 2020, each of which is hereby incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "36F8658-205961-0037-00US_SequenceListing_ST25.txt"; created on May 26, 2023, and 26,275 bytes in size, is hereby incorporated by reference.

BACKGROUND OF THE INVENTION

Among the most powerful and successful new therapies to enter the cancer clinic is CAR-T cell therapy (Brudno and Kochenderfer, 2018, Nat Rev Clin Oncol, 15(1):31-46). In this approach, patient T cells are collected, genetically modified to express a chimeric antigen receptor (CAR), expanded to very large numbers, and administered to the patient. Remarkably, CAR-T cell therapy has been effective for ~75% of patients with refractory, progressive leukemia, resulting in three FDA-approved CAR-T cell therapies (Brudno and Kochenderfer, 2018, Nat Rev Clin Oncol, 15(1):31-46). However, this therapy has not been successful for solid cancers (lung, colorectal, pancreatic, breast, etc), reflecting the need for suitable antigen targets for each disease, as well as patient, tumor, and immune factors (Baybutt et al., 2019, Clin Pharmacol Ther, 105(1):71-78). Currently, CAR-T cell therapies typically target tissue-specific surface receptors expressed by the cells from which the cancer derived. In contrast, without being bound by theory, it is proposed that the tissue disorganization that is typical of solid cancers through changes in the junctions between cells (adherens junctions, tight junctions, desmosomes, etc) will reveal novel therapy targets on the surface of cancer, but not normal cells, permitting treatment of nearly all solid cancer types via a universal target. Moreover, while patient T cells have been the primary source for cellular therapies, donor-derived NK cells may be an "off-the-shelf" approach, eliminating the need for patient-derived material. The combination of a nearly universal target with a donor-derived source of cells may create a universal, "off-the-shelf" CAR-NK cell therapy that is safe, effective, mass-manufacturable, and inexpensive for the ~1 million people dying annually of cancer in the U.S.

There is thus a need in the art for compositions and methods for treating and preventing diseases and disorders, including cancer. The present invention addresses this unmet need in the art.

SUMMARY OF THE INVENTION

In one embodiment, the invention relates to an antibody or fragment thereof that specifically binds to Dsg2. In one embodiment, the antibody comprises at least one of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, a LC CDR3 sequence of SEQ ID NO:14, a HC CDR1 sequence of SEQ ID NO:18, a HC CDR2 sequence of SEQ ID NO:20, a HC CDR3 sequence of SEQ ID NO:22, a LC CDR1 sequence of SEQ ID NO:26, a LC CDR2 sequence of SEQ ID NO:28 and a LC CDR3 sequence of SEQ ID NO:30.

In one embodiment, the antibody or fragment thereof comprises an scFv antibody fragment.

In one embodiment, the antibody or fragment thereof comprises a variable heavy chain sequence comprising the CDR sequences of SEQ ID NO:2, SEQ ID NO:4 and SEQ ID NO:6. In one embodiment, the antibody or fragment thereof comprises a variable light chain sequence comprising the CDR sequences of SEQ ID NO:10, SEQ ID NO:12 and SEQ ID NO:14. In one embodiment, the antibody or fragment thereof comprises a variable heavy chain sequence comprising the CDR sequences of SEQ ID NO:18, SEQ ID NO:20 and SEQ ID NO:22. In one embodiment, the antibody or fragment thereof comprises a variable light chain sequence comprising the CDR sequences of SEQ ID NO:26, SEQ ID NO:28 and SEQ ID NO:30. In one embodiment, the antibody or fragment thereof comprises a variable heavy chain sequence selected from the group consisting of SEQ ID NO:8 and SEQ ID NO:24. In one embodiment, the antibody or fragment thereof comprises a variable light chain sequence selected from the group consisting of SEQ ID NO:16 and SEQ ID NO:32. In one embodiment, the antibody or fragment thereof comprises a sequence having at least 95% identity to a variable heavy chain sequence of SEQ ID NO:8 or SEQ ID NO:24. In one embodiment, the antibody or fragment thereof comprises a sequence having at least 95% identity to a variable light chain sequence of SEQ ID NO:16 or SEQ ID NO:32. In one embodiment, the antibody or fragment thereof comprises a fragment comprising at least 80% of the full-length sequence of SEQ ID NO:8 and SEQ ID NO:24. In one embodiment, the antibody or fragment thereof comprises a fragment comprising at least 80% of the full-length sequence of a variable light chain sequence of SEQ ID NO:16 or SEQ ID NO:32.

In one embodiment, the invention relates to a composition comprising a chimeric antigen receptor (CAR) molecule comprising a domain that specifically bind to Dsg2. a domain that specifically binds to Dsg2. In one embodiment, the domain that specifically binds to Dsg2 comprises an scFv antibody fragment. In one embodiment, the domain that specifically binds to Dsg2 comprises Dsg2, an anti-Dsg2 antibody or a fragment thereof.

In one embodiment, the CAR comprises a Dsg2 binding molecule comprising a variable heavy chain sequence comprising the CDR sequences of SEQ ID NO:2, SEQ ID NO:4 and SEQ ID NO:6. In one embodiment, the CAR comprises a Dsg2 binding molecule comprising a variable light chain sequence comprising the CDR sequences of SEQ ID NO:10, SEQ ID NO:12 and SEQ ID NO:14. In one embodiment, the CAR comprises a Dsg2 binding molecule comprising a variable heavy chain sequence comprising the CDR sequences of SEQ ID NO:18, SEQ ID NO:20 and SEQ ID NO:22. In one embodiment, the CAR comprises a Dsg2 binding molecule comprising a variable light chain sequence comprising the CDR sequences of SEQ ID NO:26, SEQ ID NO:28 and SEQ ID NO:30. In one embodiment, the CAR comprises a Dsg2 binding molecule comprising a variable heavy chain sequence selected from the group consisting of SEQ ID NO:8 and SEQ ID NO:24. In one embodiment, the CAR comprises a Dsg2 binding molecule comprising a variable light chain sequence selected from the group consisting of SEQ ID NO:16 and SEQ ID NO:32. In one embodiment, the CAR comprises a Dsg2 binding molecule comprising a sequence having at least 95% identity to a variable heavy chain sequence of SEQ ID NO:8 or SEQ ID NO:24. In one embodiment, the CAR comprises a Dsg2 binding molecule comprising a sequence having at least 95% identity to a variable light chain sequence of SEQ ID NO:16 or SEQ ID NO:32. In one embodiment, the CAR comprises a Dsg2 binding molecule comprising a fragment comprising at least 80% of the full-length sequence of SEQ ID NO:8 and SEQ ID NO:24. In one embodiment, the CAR comprises a Dsg2 binding molecule comprising a fragment comprising at least 80% of the full-length sequence of a variable light chain sequence of SEQ ID NO:16 or SEQ ID NO:32. In one embodiment, the CAR comprises a sequence as set forth in SEQ ID NO:34 or SEQ ID NO:36. In one embodiment, the CAR comprises a sequence having at least 95% identity to SEQ ID NO:34 or SEQ ID NO:36. In one embodiment, the CAR comprises a sequence a fragment comprising at least 80% of the full-length sequence of SEQ ID NO:34 or SEQ ID NO:36.

In one embodiment, the composition further comprises a pharmaceutically acceptable excipient, an adjuvant, or a combination thereof.

In one embodiment, the invention relates to a nucleic acid molecule encoding an antibody or fragment thereof that specifically binds to Dsg2. In one embodiment, the nucleic acid molecule encodes an antibody comprising at least one of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, a LC CDR3 sequence of SEQ ID NO:14, a HC CDR1 sequence of SEQ ID NO:18, a HC CDR2 sequence of SEQ ID NO:20, a HC CDR3 sequence of SEQ ID NO:22, a LC CDR1 sequence of SEQ ID NO:26, a LC CDR2 sequence of SEQ ID NO:28 and a LC CDR3 sequence of SEQ ID NO:30.

In one embodiment, the nucleic acid molecule encodes an antibody comprising a variable heavy chain sequence comprising the CDR sequences of SEQ ID NO:2, SEQ ID NO:4 and SEQ ID NO:6. In one embodiment, the nucleic acid molecule encodes an antibody comprising a variable light chain sequence comprising the CDR sequences of SEQ ID NO:10, SEQ ID NO:12 and SEQ ID NO:14. In one embodiment, the nucleic acid molecule encodes an antibody comprising a variable heavy chain sequence comprising the CDR sequences of SEQ ID NO:18, SEQ ID NO:20 and SEQ ID NO:22. In one embodiment, the nucleic acid molecule encodes an antibody comprising a variable light chain sequence comprising the CDR sequences of SEQ ID NO:26, SEQ ID NO:28 and SEQ ID NO:30. In one embodiment, the nucleic acid molecule encodes an antibody comprising a variable heavy chain sequence selected from the group consisting of SEQ ID NO:8 and SEQ ID NO:24. In one embodiment, the nucleic acid molecule encodes an antibody comprising a variable light chain sequence selected from the group consisting of SEQ ID NO:16 and SEQ ID NO:32. In one embodiment, the nucleic acid molecule encodes an antibody comprising a sequence having at least 95% identity to a variable heavy chain sequence of SEQ ID NO:8 or SEQ ID NO:24. In one embodiment, the nucleic acid molecule encodes an antibody comprising a sequence having at least 95% identity to a variable light chain sequence of SEQ ID NO:16 or SEQ ID NO:32. In one embodiment, the nucleic acid molecule encodes a fragment comprising at least 80% of the full-length sequence of SEQ ID NO:8, SEQ ID NO:24, SEQ ID NO:16 or SEQ ID NO:32.

In one embodiment, the nucleic acid encoding an antibody or fragment thereof that specifically binds to Dsg2 comprises at least one of: a nucleotide sequence of SEQ ID NO:1 encoding a HC CDR1; a nucleotide sequence of SEQ ID NO:3 encoding a HC CDR2; a nucleotide sequence of SEQ ID NO:5 encoding a HC CDR3; a nucleotide sequence of SEQ ID NO:9 encoding a LC CDR1; a nucleotide sequence of SEQ ID NO:11 encoding a LC CDR2; a nucleotide sequence of SEQ ID NO:13 encoding a LC CDR3; a nucleotide sequence of SEQ ID NO:17 encoding a HC CDR1; a nucleotide sequence of SEQ ID NO:19 encoding a HC CDR2; a nucleotide sequence of SEQ ID NO:21 encoding a HC CDR3; a nucleotide sequence of SEQ ID NO:25 encoding a LC CDR1; a nucleotide sequence of SEQ ID NO:27 encoding a LC CDR2; and a nucleotide sequence of SEQ ID NO:29 encoding a LC CDR3.

In one embodiment, the nucleic acid molecule encoding an antibody or fragment thereof that specifically binds to Dsg2 comprises a nucleotide sequence comprising the CDR sequences of SEQ ID NO:1, SEQ ID NO:3 and SEQ ID NO:5, encoding a variable heavy chain sequence. In one embodiment, the nucleic acid molecule encoding an antibody or fragment thereof that specifically binds to Dsg2 comprises a nucleotide sequence comprising the CDR sequences of SEQ ID NO:9, SEQ ID NO:11 and SEQ ID NO:13, encoding a variable light chain sequence. In one embodiment, the nucleic acid molecule encoding an antibody or fragment thereof that specifically binds to Dsg2 comprises a nucleotide sequence comprising the CDR sequences of SEQ ID NO:17, SEQ ID NO:19 and SEQ ID NO:21, encoding a variable heavy chain sequence. In one embodiment, the nucleic acid molecule encoding an antibody or fragment thereof that specifically binds to Dsg2 comprises a nucleotide sequence comprising the CDR sequences of SEQ ID NO:25, SEQ ID NO:27 and SEQ ID NO:29, encoding a variable heavy chain sequence. In one embodiment, the nucleic acid molecule encoding an antibody or fragment thereof that specifically binds to Dsg2 comprises a nucleotide sequence selected from the group consisting of SEQ ID NO:7 and SEQ ID NO:23, encoding a variable heavy chain sequence. In one embodiment, the nucleic acid molecule encoding an antibody or fragment thereof that specifically binds to Dsg2 comprises a nucleotide sequence selected from the group consisting of SEQ ID NO:15 and SEQ ID NO:31, encoding a variable light chain sequence. In one embodiment, the nucleic acid molecule encoding an antibody or fragment thereof that specifically binds to Dsg2 comprises a sequence having at least 95% identity to a nucleotide sequence selected from the group consisting of SEQ ID NO:7 and SEQ ID NO:23. In one embodiment, the nucleic acid molecule encoding an antibody or fragment thereof that specifically binds to Dsg2 comprises a sequence having at least 95% identity to a nucleotide sequence selected from the group consisting of SEQ ID NO:15 and SEQ ID NO:31. In one embodiment, the nucleic acid molecule encoding an antibody or fragment thereof that specifically binds to Dsg2 comprises a fragment comprising at least 80% of the full-length sequence of a nucleotide sequence selected from the group consisting of SEQ ID NO:7 and SEQ ID NO:23. In one embodiment, the nucleic acid molecule encoding an antibody or fragment thereof that specifically binds to Dsg2 comprises a fragment comprising at least 80% of the full-length sequence of a nucleotide sequence selected from the group consisting of SEQ ID NO:15 and SEQ ID NO:31.

In one embodiment, the nucleic acid molecule encoding an antibody or fragment thereof that specifically binds to Dsg2 encodes a CAR molecule comprising an scFv antibody fragment.

In one embodiment, the nucleic acid molecule encoding the CAR comprises a nucleotide sequence comprising the CDR sequences of SEQ ID NO:1, SEQ ID NO:3 and SEQ ID NO:5, encoding a variable heavy chain sequence. In one embodiment, the nucleic acid molecule encoding the CAR comprises a nucleotide sequence comprising the CDR sequences of SEQ ID NO:9, SEQ ID NO:11 and SEQ ID NO:13, encoding a variable light chain sequence. In one embodiment, the nucleic acid molecule encoding the CAR comprises a nucleotide sequence comprising the CDR sequences of SEQ ID NO:17, SEQ ID NO:19 and SEQ ID NO:21, encoding a variable heavy chain sequence. In one embodiment, the nucleic acid molecule encoding the CAR comprises a nucleotide sequence comprising the CDR sequences of SEQ ID NO:25, SEQ ID NO:27 and SEQ ID NO:29, encoding a variable heavy chain sequence. In one embodiment, the nucleic acid molecule encoding the CAR comprises a nucleotide sequence selected from the group consisting of SEQ ID NO:7 and SEQ ID NO:23, encoding a variable heavy chain sequence. In one embodiment, the nucleic acid molecule encoding the CAR comprises a nucleotide sequence selected from the group consisting of SEQ ID NO:15 and SEQ ID NO:31, encoding a variable light chain sequence. In one embodiment, the nucleic acid molecule encoding the CAR comprises a sequence having at least 95% identity to a nucleotide sequence selected from the group consisting of SEQ ID NO:7 and SEQ ID NO:23. In one embodiment, the nucleic acid molecule encoding the CAR comprises a sequence having at least 95% identity to a nucleotide sequence selected from the group consisting of SEQ ID NO:15 and SEQ ID NO:31. In one embodiment, the nucleic acid molecule encoding the CAR comprises a fragment comprising at least 80% of the full-length sequence of a nucleotide sequence selected from the group consisting of SEQ ID NO:7 and SEQ ID NO:23. In one embodiment, the nucleic acid molecule encoding the CAR comprises a fragment comprising at least 80% of the full-length sequence of a nucleotide sequence selected from the group consisting of SEQ ID NO:15 and SEQ ID NO:31. In one embodiment, the nucleic acid molecule encoding the CAR comprises a nucleotide sequence selected from the group consisting of SEQ ID NO:33 and SEQ ID NO:35. In one embodiment, the nucleic acid molecule encoding the CAR comprises a sequence having at least 95% identity to a nucleotide sequence selected from the group consisting of SEQ ID NO:33 and SEQ ID NO:35. In one embodiment, the nucleic acid molecule encoding the CAR comprises a fragment comprising at least 80% of the full-length sequence of a nucleotide sequence selected from the group consisting of SEQ ID NO:33 and SEQ ID NO:35.

In one embodiment, the nucleic acid molecule comprises an expression vector. In one embodiment, the nucleic acid molecule is incorporated into a viral particle.

In one embodiment, the invention relates to a composition comprising a nucleic acid molecule encoding an antibody or fragment thereof that specifically binds to Dsg2 or a CAR molecule comprising an antibody or fragment thereof that specifically binds to Dsg2.

In one embodiment, the composition comprises a pharmaceutically acceptable excipient, an adjuvant, or a combination thereof.

In one embodiment, the invention relates to an isolated cell expressing a nucleic acid molecule encoding an antibody or fragment thereof that specifically binds to Dsg2 or a CAR molecule comprising an antibody or fragment thereof that specifically binds to Dsg2.

In one embodiment, the cell is an immune cell. In one embodiment, the immune cell is a T helper cell, cytotoxic T cell, memory T cell, effector T cell, Th1 cell, Th2 cell, Th9 cell, Th17 cell, Th22 cell, Tfh (follicular helper) cell, T regulatory cell, natural killer T cell, mucosal associated invariant T cell (MATT), γδ T cell, TCR-transgenic T cell, a T-cell redirected for universal cytokine-mediated killing (TRUCK), Tumor infiltrating T cell (TIL), or CAR-T cell. In one embodiment, the immune cell is a natural killer (NK) cell.

In one embodiment, the invention relates to a method of treating or preventing a disease or disorder in a subject in need thereof, the method comprising administering a composition comprising an antibody or fragment thereof that specifically binds to a Dsg2. In one embodiment, the invention relates to a method of treating or preventing a disease or disorder in a subject in need thereof, the method comprising administering a composition comprising a nucleic acid molecule encoding an antibody or fragment thereof that specifically binds to a Dsg2. In one embodiment, the invention relates to a method of treating or preventing a disease or disorder in a subject in need thereof, the method comprising administering an isolated cell comprising a nucleic acid molecule encoding an antibody or fragment thereof that specifically binds to a Dsg2.

In one embodiment, the disease or disorder is a cancer, or a disease or disorder associated with cancer.

In one embodiment, the cancer is adrenocortical carcinoma (ACC); bladder urothelial carcinoma (BLCA); breast invasive carcinoma (BRCA); cervical squamous cell carcinoma and endocervical adenocarcinoma (CESC); cholangio carcinoma cholangiocarcinoma (CHOL); colon adenocarcinoma (COAD); lymphoid neoplasm diffuse large B-cell lymphoma (DLBC); esophageal carcinoma (ESCA); glioblastoma multiforme (GBM); head and neck squamous cell carcinoma (HNSC); kidney chromophobe (KICH); kidney renal clear cell carcinoma (KIRC); kidney renal papillary cell carcinoma (KIRP); acute myeloid leukemia (LAML); brain lower grade glioma (LGG); liver hepatocellular carcinoma (LIHC); lung adenocarcinoma (LUAD); lung squamous cell carcinoma (LUSC); mesothelioma (MESO); multiple myeloma (MM); ovarian serous cystadenocarcinoma (OV); pancreatic adenocarcinoma (PAAD); pheochromocytoma and paraganglioma (PCPG); prostate adenocarcinoma (PRAD); rectum adenocarcinoma (READ); sarcoma (SARC); skin cutaneous melanoma (SKCM); stomach adenocarcinoma (STAD); testicular germ cell tumors (TGCT); thyroid carcinoma (THCA); thymoma (THYM); uterine corpus endometrial carcinoma (UCEC); uterine carcinosarcoma (UCS); or uveal Melanoma (UVM).

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2A depicts the fraction of patients with various cancers whose tumors demonstrate medium or high Dsg2 protein expression (from the Human Protein Atlas). FIG. 2B depicts representative immunohistochemistry of prostate, pancreatic, colorectal, and lung cancers stained for Dsg2 showing abundant expression throughout the cancer (from the Human Protein Atlas). FIG. 2C depicts upregulation in representative cancers (prostate, pancreatic, colorectal, and lung) by mRNA quantification (compiled by GEPIA2 using TCGA and GTEx project data). FIG. 2D and FIG. 2E depict the 5-year survival probability of pancreatic and lung cancer patients, respectively, by Dsg2 expression (compiled by GEPIA2 using TCGA and GTEx project data).

FIG. 3A depicts data demonstrating that xenograft tumors were established in SCID mice using A431 cSCC cells expressing –GFP or –Dsg2/GFP. Tumor volumes were calculated using the formula: $V=0.5(L*W2)$. Data expressed as average ±SEM. Two-way repeated measures ANOVA. *$P<0.05$. FIGS. 3B and 3C depicts data demonstrating that xenograft tumors were established using A431 cSCC cells. After 1 week, mice were treated twice weekly with 5 mg/kg of mAB 6D8 (FIG. 3B) or mAB 10D2 (FIG. 3C).

FIG. 5A depicts a schematic diagram of the Dsg2 domains. P, Pro-region; EC, Extracellular Domain; TM, Transmembrane; IA, Intracellular Anchoring, ICS, Intracellular Cadherin Segment; LD, Linker Domain; RUD, Repeat Unit Domain; TD, Terminal Domain. 10D2 recognizes EC1 while 6D8 recognizes EC4. For FIG. 5B and FIG. 5C, A431 SCC was immunoblotted (FIG. 5B) or immunostained (FIG. 5C) with mAbs 6D8 and 10D2.

FIG. 10A depicts no PMA/ionomycin negative control, nonspecific protein (BSA) stimulation control, recombinant huma Dsg2 protein, anti-penta-HIS antibody (CAR construct-specific positive control), PMA/ionomycin (antigen/CAR-independent positive control). FIG. 10B depicts human A431 cSCC cell line variants: A431 parental with GFP, A431 with palmitoylation mutant of Dsg2, A431 with Dsg2 overexpression, A431 Dsg2 CRISPR/Cas9 knockout, (DLD-1) human colorectal adenocarcinoma cell line, non-specific PMA/ionomycin positive control.

Figures 14A, 14B, 14C:
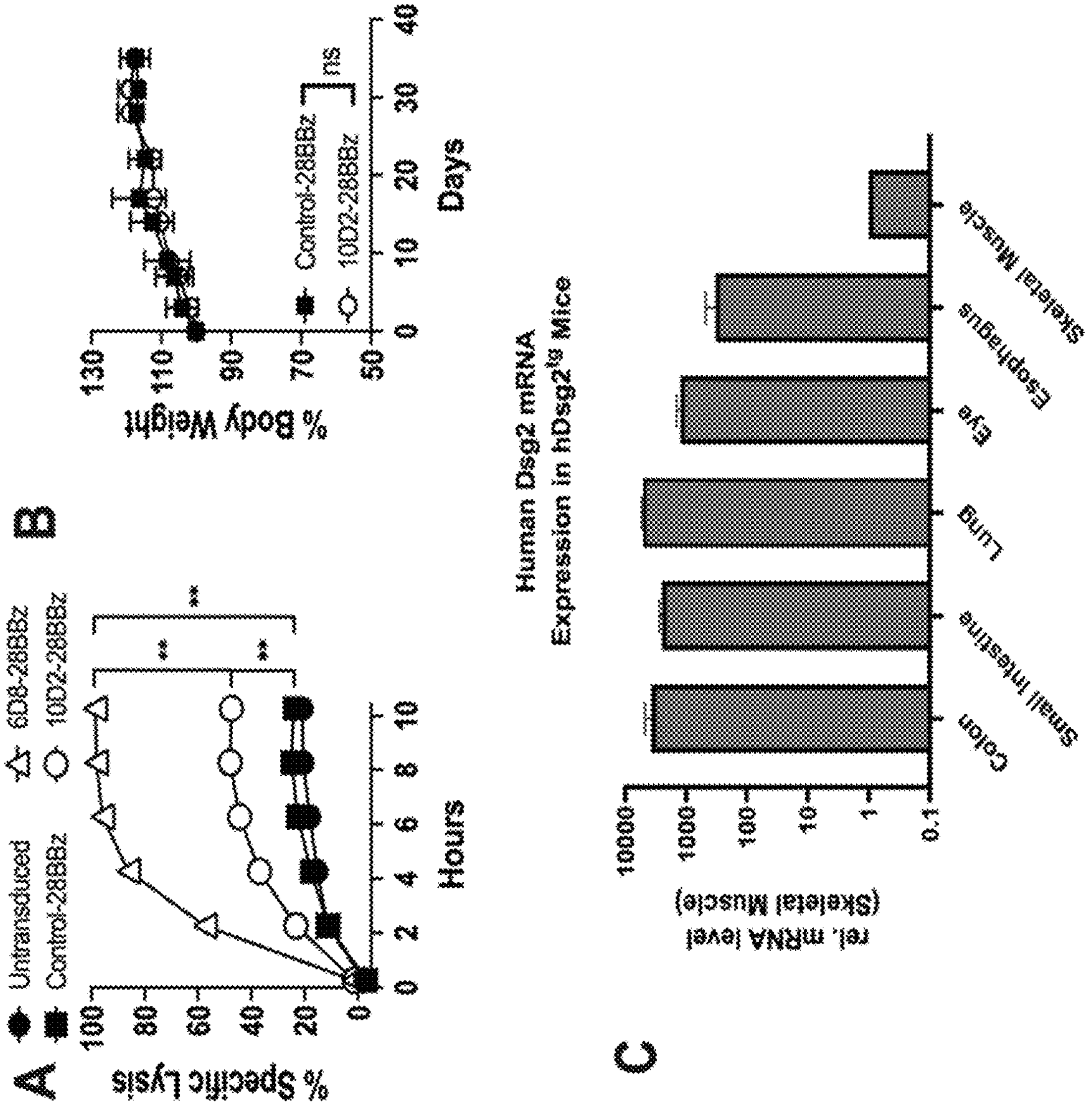

FIG. 14A depicts exemplary experiments demonstrating CAR-T cell killing of A431 SCC cells by Dsg2 CAR-T cells produced with 6D8 and 10D2 scFvs. Untransduced (no CAR) and 1D3 CAR-transduced T cells are negative controls.

FIG. 14B depicts exemplary experiments demonstrating safety of 10D2 Dsg2 CAR-T cells in mice. Body weight analysis demonstrates no change in body weight of mice receiving Dsg2 CAR-T cells produced from the 10D2 scFv.

Figure 8:
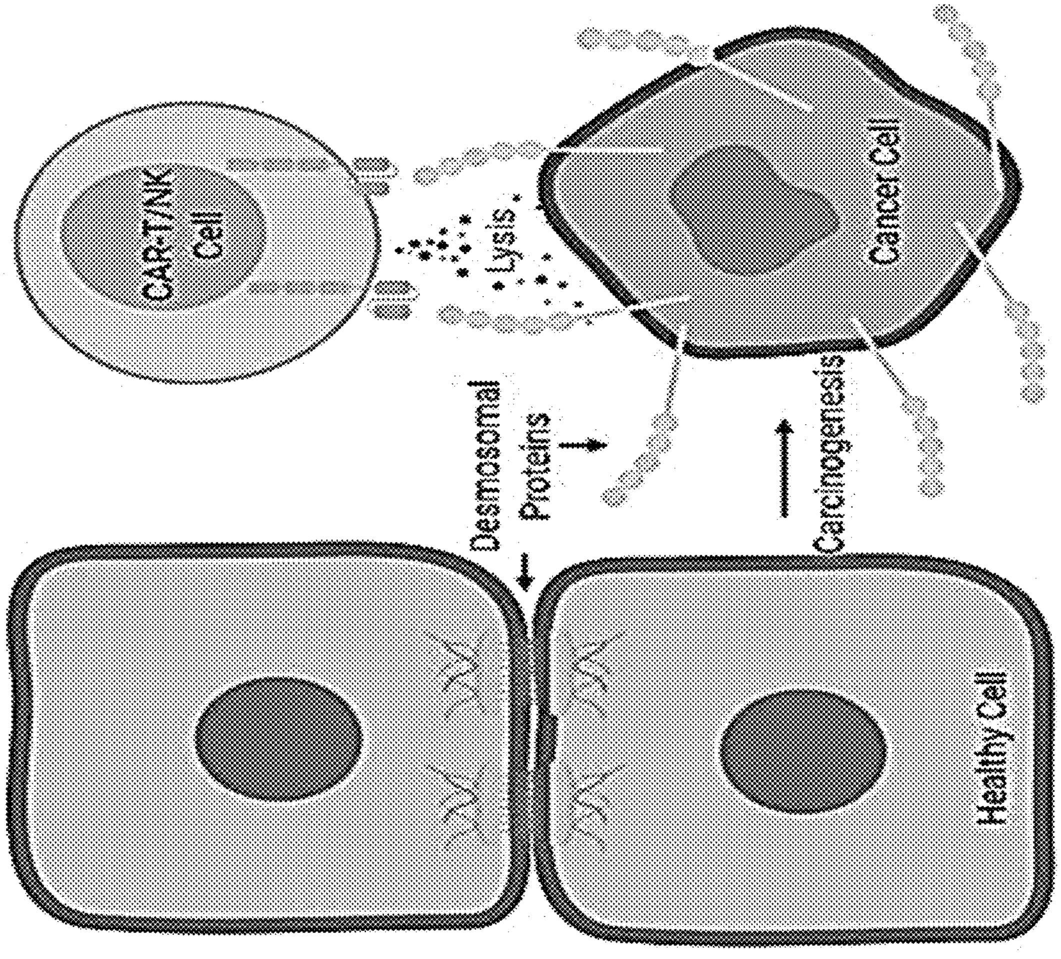
FIG. 8 depicts results from exemplary experiments demonstrating a "Window of opportunity" for Dsg2-targeting. Based on preliminary data, the hypothesis is that in normal cells, Dsg2 is localized to the desmosomal complex and is not accessible to CAR-T or CAR-NK cells. In contrast, tumor cells express high levels of non-desmosome-associated Dsg2 which is targetable by CAR-T/NK cells.
Figures 14D, 14E:
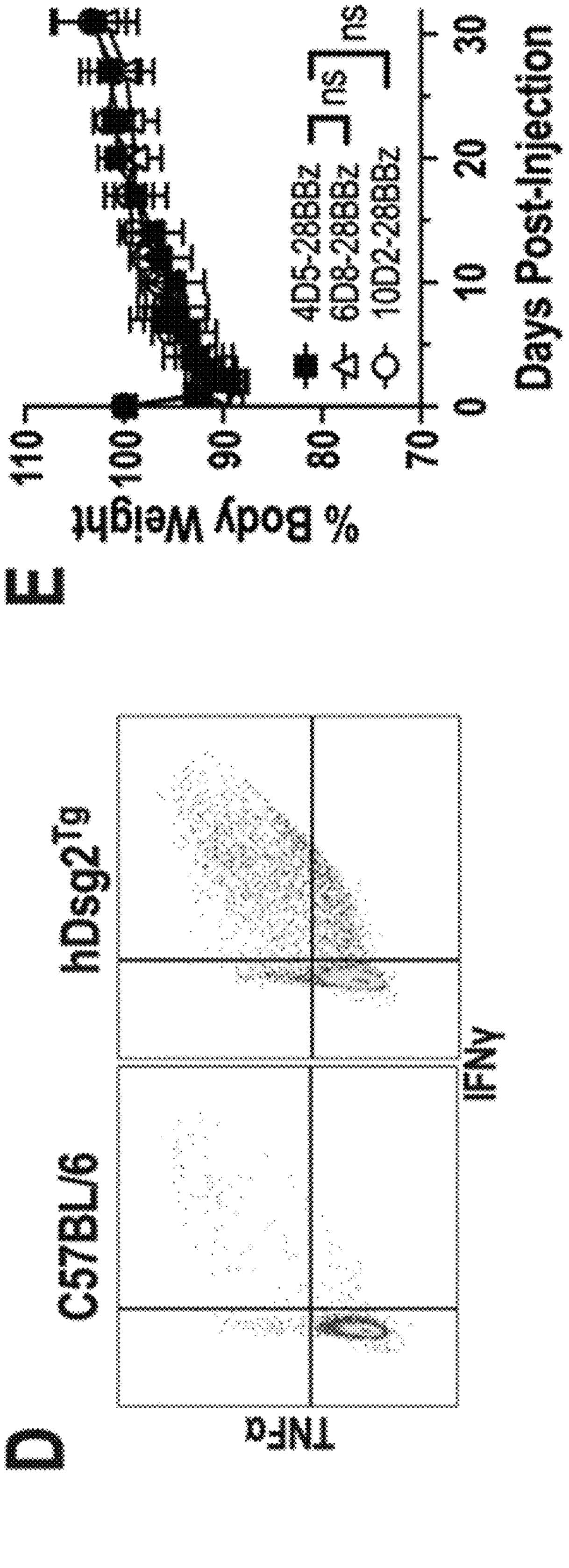

FIG. 14C through 14E depict exemplary experiments validating the mouse model expressing human Dsg2 transgene (hDsg2 T g mice) and safety of CAR-T cells in those mice. hDsg2 T g mice express Dsg2 in most tissues, mimicking humans (selected tissues shown in FIG. 14C). Moreover, keratinocytes isolated from hDsg2 T g mice activate Dsg2 CAR-T cells in a dish (FIG. 14D) reflecting the disruption of desmosomes (FIG. 8). Despite the robust expression of hDsg2 in tissues (FIG. 14C), 10D8 and 6D8 CAR-T cells administered to hDsg2 T g mice produced no toxicity (FIG. 14E).

Figure 15A:
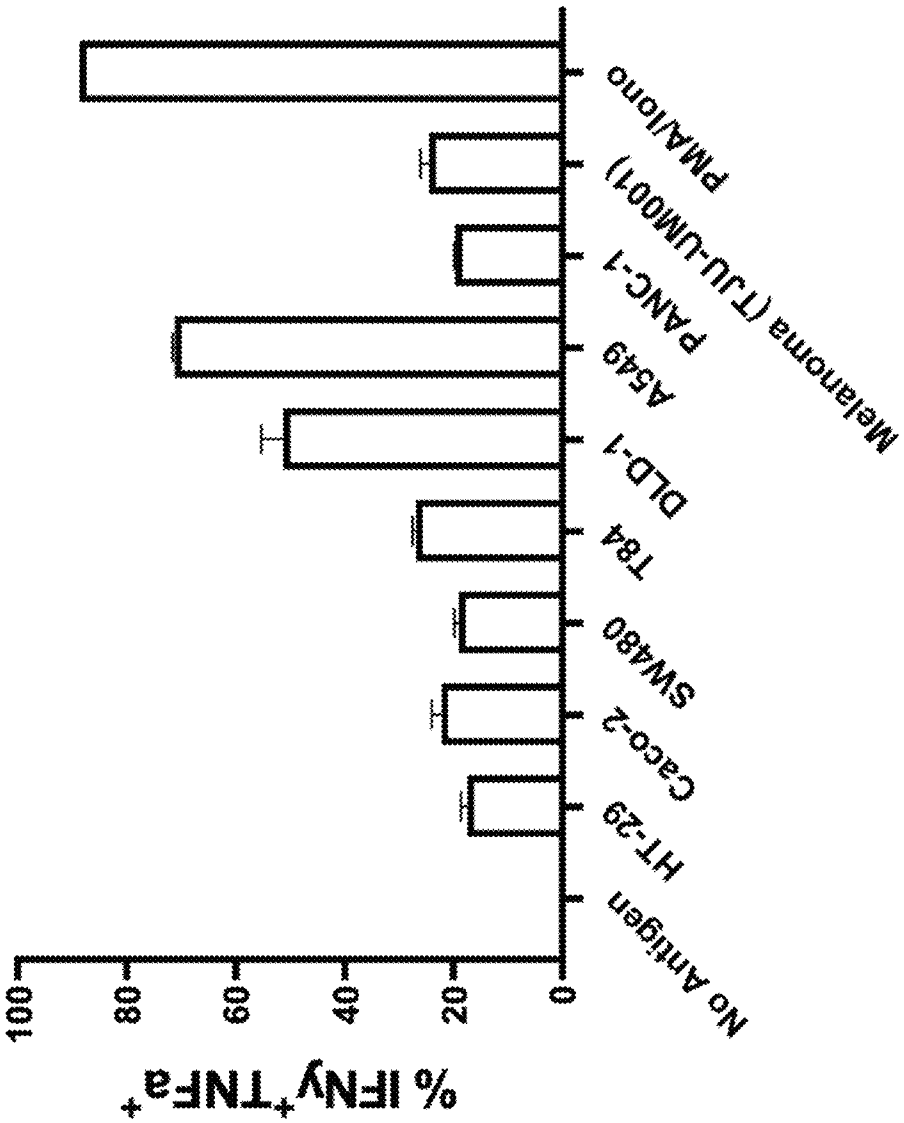
Figure 15B:
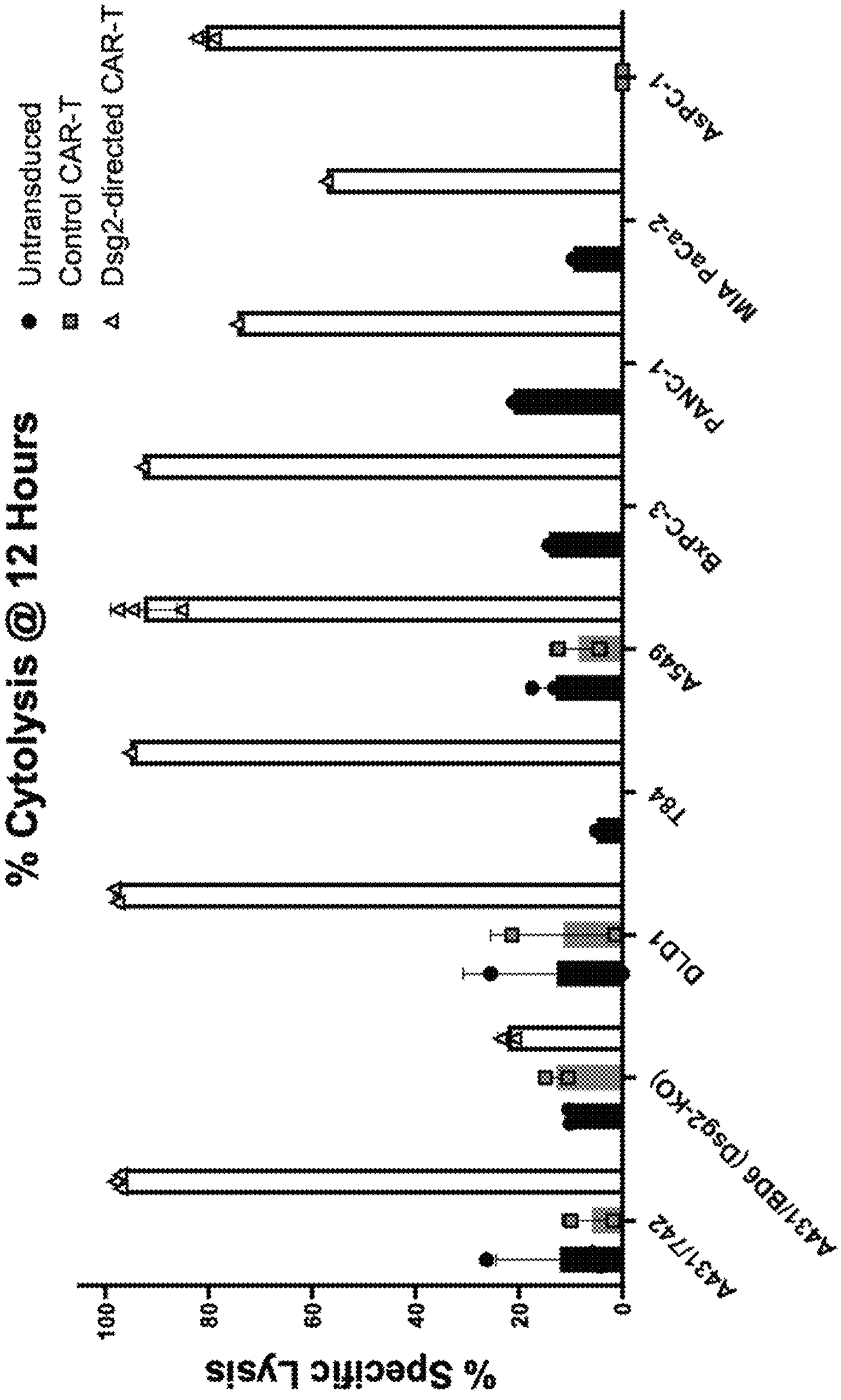

FIG. 15A and FIG. 15B depict results of exemplary experiments demonstrating in vitro CAR-T cell efficacy against a variety of solid cancer types. Various human cancer types, including squamous cell carcinoma (A431), colorectal (HT-29, Caco-2, SW480, T84, and DLD-1), lung (A549), pancreatic (PANC-1), and melanoma (TJU-UM001) cancer were incubated with 6D8 Dsg2 CAR-T cells and effector cytokine (IFNγ and TNFα) production was quantified by flow cytometry (FIG. 15A). "No antigen" and "PMA/IONO" served as negative and positive controls, respectively. Various human cancer types, including squamous cell carcinoma (A431), colorectal (DLD-1 and T84), lung (A549), and pancreatic (BxPC-3, PANC-1, MIA PaCa-2, and AsPC-1) cancer were incubated with 6D8 Dsg2 CAR-T cells and their lysis was quantified by RTCA (FIG. 15B). Dsg2 knockout A431 were a negative control. All lines tested resulted in effector cytokine production (FIG. 15A) and lysis (FIG. 15B), except those cells in which Dsg2 was deleted with CRISPR-Cas9 (Dsg2-KO).

Figure 16:
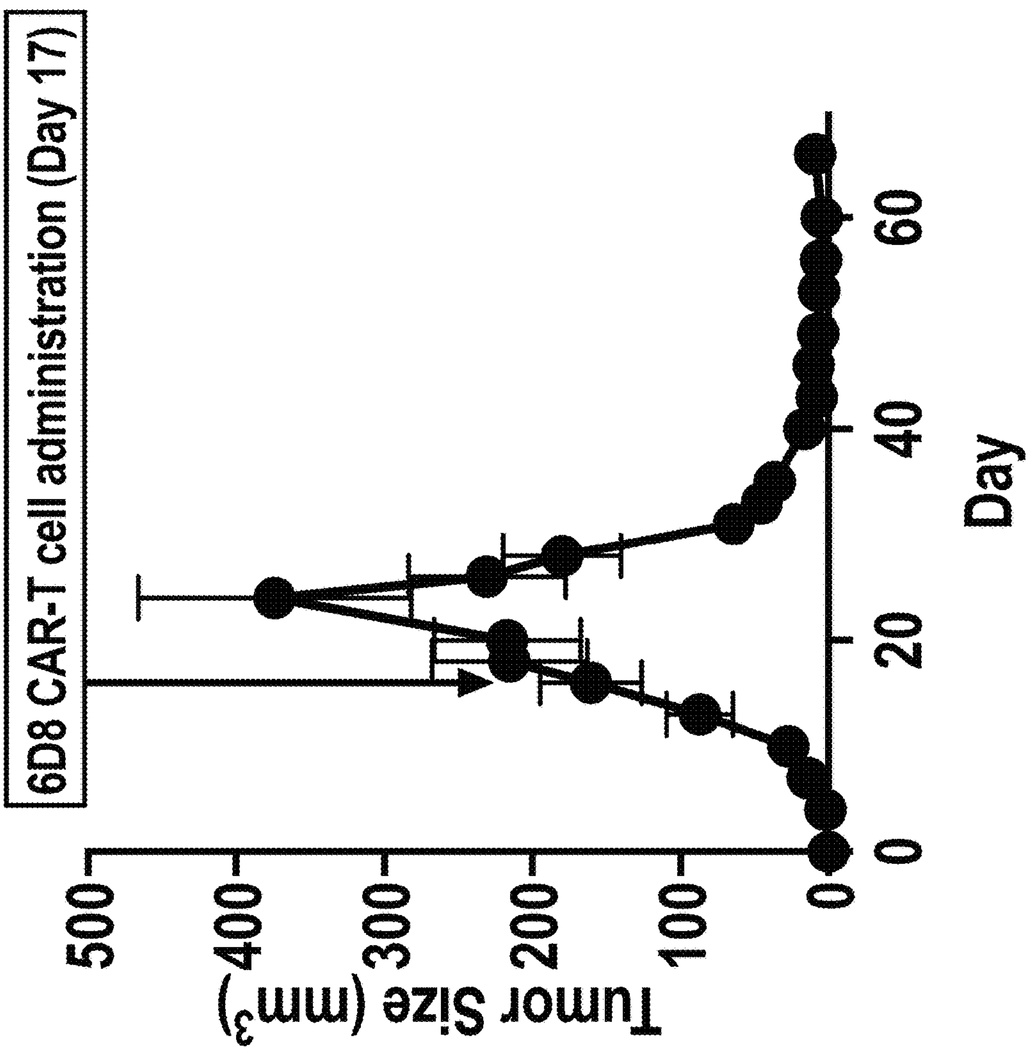

FIG. 16 depicts the results of exemplary experiments demonstrating in vivo CAR-T cell efficacy in treating DLD-1 colorectal tumors. In vivo tumor size measurements demonstrating rapid and complete elimination of DLD-1 tumors by 6D8 Dsg2 CAR-T cells administered on day 17 of tumor growth (FIG. 16).

DETAILED DESCRIPTION

The present invention relates to compositions comprising Dsg2 binding molecules, such as antibodies, fragments thereof, variants thereof, and to nucleic acid molecules encoding the same, and methods of use for diagnosing or treating diseases and disorders in a subject in need thereof.

In some embodiments, the present invention relates to chimeric antigen receptor (CAR) molecules comprising the Dsg2 binding molecules, fragments thereof, variants thereof; or a nucleic acid molecule encoding the same.

In some embodiments, the present invention relates to immune cells expressing CAR molecules comprising the Dsg2 binding molecules, fragments thereof, or variants thereof.

In some embodiments, the present invention relates to methods of treating a disease or disorder in a subject in need thereof, comprising administering to the subject a Dsg2 binding molecule, fragment thereof, variant thereof, a nucleic acid molecule encoding the same, a CAR molecule comprising a Dsg2 binding molecule, fragment thereof, variant thereof, or a nucleic acid molecule encoding the same, or an immune cell expressing a CAR molecule comprising a Dsg2 binding molecule, fragment thereof, or variant thereof.

In one embodiment, the disease or disorder is cancer. In one embodiment, the cancer is a solid tumor. In one embodiment, the cancer is selected from the group consisting of adrenocortical carcinoma (ACC); bladder urothelial carcinoma (BLCA); breast invasive carcinoma (BRCA); cervical squamous cell carcinoma and endocervical adenocarcinoma (CESC); cholangiocarcinoma (CHOL); colon adenocarcinoma (COAD); lymphoid neoplasm diffuse large B-cell lymphoma (DLBC); esophageal carcinoma (ESCA); glioblastoma multiforme (GBM); head and neck squamous cell carcinoma (HNSC); kidney chromophobe (KICH); kidney renal clear cell carcinoma (KIRC); kidney renal papillary cell carcinoma (KIRP); acute myeloid leukemia (LAML); brain lower grade glioma (LGG); liver hepatocellular carcinoma (LIHC); lung adenocarcinoma (LUAD); lung squamous cell carcinoma (LUSC); mesothelioma (MESO); multiple myeloma (MM); ovarian serous cystadenocarcinoma (OV); pancreatic adenocarcinoma (PAAD); pheochromocytoma and paraganglioma (PCPG); prostate adenocarcinoma (PRAD); rectum adenocarcinoma (READ); sarcoma (SARC); skin cutaneous melanoma (SKCM); stomach adenocarcinoma (STAD); testicular germ cell tumors (TGCT); thyroid carcinoma (THCA); thymoma (THYM); uterine corpus endometrial carcinoma (UCEC); uterine carcinosarcoma (UCS); and uveal melanoma (UVM).

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody, which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The term should also be construed to mean an antibody, which has been generated by the synthesis of an RNA molecule encoding the antibody. The RNA molecule expresses an antibody protein, or an amino acid sequence specifying the antibody, wherein the RNA has been obtained by transcribing DNA (synthetic or cloned) or other technology, which is available and well known in the art.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequences or a partial nucleotide sequence encoding a protein that elicits an adaptive immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "adjuvant" as used herein is defined as any molecule to enhance an antigen-specific adaptive immune response.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Immunogen" refers to any substance introduced into the body in order to generate an immune response. That substance can a physical molecule, such as a protein, or can be encoded by a vector, such as DNA, mRNA, or a virus.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells (APCs). Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, macrophage infiltration, and the like.

"Immune cell," as the term is used herein, means any cell involved in the mounting of an immune response. Such cells include, but are not limited to, T cells, B cells, NK cells, antigen-presenting cells (e.g., dendritic cells and macrophages), monocytes, neutrophils, eosinophils, basophils, and the like.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject.

The terms "patient," "subject," "individual," and the like are used interchangeably herein, and refer to any animal, or cells thereof whether in vitro or in situ, amenable to the methods described herein. In some non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. Cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, diminution, remission, or eradication of at least one sign or symptom of a disease or disorder state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based in part on the development of compositions for binding to Dsg2, which is highly expressed in cancerous cells. In one embodiment, the present invention provides a composition for treating or preventing cancer comprising a Dsg2 binding molecule of the invention. In some embodiments, the composition is an immunogenic composition (e.g., vaccine) that induces an immune response. In one embodiment, the composition is a therapeutic agent directed to the disease or disorder. For example, in one embodiment, the composition is an antibody or antibody fragment that specifically binds to Dsg2.

In one embodiment, the compositions and methods of the present invention may be used to treat or prevent a solid cancer, including, but not limited to, adrenocortical carcinoma (ACC); bladder urothelial carcinoma (BLCA); breast invasive carcinoma (BRCA); cervical squamous cell carcinoma and endocervical adenocarcinoma (CESC); cholangiocarcinoma (CHOL); colon adenocarcinoma (COAD); lymphoid neoplasm diffuse large B-cell lymphoma (DLBC); esophageal carcinoma (ESCA); glioblastoma multiforme (GBM); head and neck squamous cell carcinoma (HNSC); kidney chromophobe (KICH); kidney renal clear cell carcinoma (KIRC); kidney renal papillary cell carcinoma (KIRP); acute myeloid leukemia (LAML); brain lower grade glioma (LGG); liver hepatocellular carcinoma (LIHC); lung adenocarcinoma (LUAD); lung squamous cell carcinoma (LUSC); mesothelioma (MESO); multiple myeloma (MM); ovarian serous cystadenocarcinoma (OV); pancreatic adenocarcinoma (PAAD); pheochromocytoma and paraganglioma (PCPG); prostate adenocarcinoma (PRAD); rectum adenocarcinoma (READ); sarcoma (SARC); skin cutaneous melanoma (SKCM); stomach adenocarcinoma (STAD); testicular germ cell tumors (TGCT); thyroid carcinoma (THCA); thymoma (THYM); uterine corpus endometrial carcinoma (UCEC); uterine carcinosarcoma (UCS); and uveal Melanoma (UVM).

Compositions

One aspect of this invention relates to an agent characterized by its ability to bind to Dsg2 or an epitope thereof. Non-limiting examples of an agent able to bind to Dsg2, or Dsg2 binding molecule, include an antibody, an aptamer, a molecular probe, peptide, peptidomimetic, small molecule, and conjugates thereof. In one embodiment, the Dsg2 binding molecule comprises an anti-Dsg2 nanobody that specifically binds to Dsg2. In one embodiment, the Dsg2 binding molecule comprises a Dsg2 interacting protein, or fragment thereof. Dsg2 forms homodimers, therefore, in one embodiment, the Dsg2 binding molecule comprises Dsg2 or a fragment thereof, which dimerizes with another Dsg2 molecule.

In one embodiment, the Dsg2 binding molecule is a polyclonal antibody. In another embodiment, the Dsg2 binding molecule is a monoclonal antibody. In some embodiments, the Dsg2 binding molecule is a chimeric antibody. In some embodiments, the Dsg2 binding molecule is a humanized antibody. In some embodiments, the Dsg2 binding molecule comprises an antibody fragment. In some embodiments, the Dsg2 binding molecule comprises a scFv antibody fragment.

In some embodiments, the Dsg2 binding molecule is an intact monoclonal or polyclonal antibody, or immunologically portion or active fragment thereof. Thus, in various embodiments, the Dsg2 binding molecule of invention is a polyclonal antibody, monoclonal antibody, intracellular antibody ("intrabody"), Fv, Fab, Fab', F(ab)2 and F(ab')2, single chain antibody (scFv), heavy chain antibody (e.g., such as a camelid antibody), synthetic antibody, chimeric antibody, or humanized antibodies (see, for example, Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426). Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

In one embodiment, the invention relates to compositions comprising at least one Dsg2 antibody, or fragment thereof. In one embodiment, the anti-Dsg2 antibody, or fragment thereof, comprises 1, 2, 3, 4, 5, or all 6 of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, and a LC CDR3 sequence of SEQ ID NO:14. In one embodiment, the anti-Dsg2 antibody, or fragment thereof, comprises 1, 2, 3, 4, 5, or all 6 of: a heavy chain (HC) CDR1 sequence of SEQ ID NO:18, a HC CDR2 sequence of SEQ ID NO:20, a HC CDR3 sequence of SEQ ID NO:22, a light chain (LC) CDR1 sequence of SEQ ID NO:26, a LC CDR2 sequence of SEQ ID NO:28, and a LC CDR3 sequence of SEQ ID NO:30.

In one embodiment, the anti-Dsg2 antibody, or fragment thereof comprises a heavy chain variable region having a sequence as set forth in SEQ ID NO:8, or a fragment or variant thereof. In one embodiment, the anti-Dsg2 antibody, or fragment thereof comprises a light chain variable region having a sequence as set forth in SEQ ID NO:16, or a fragment or variant thereof. In one embodiment, the anti-Dsg2 antibody, or fragment thereof comprises a heavy chain variable region sequence of SEQ ID NO:8, or a fragment or variant thereof, and a light chain variable region sequence of SEQ ID NO:16, or a fragment or variant thereof.

In one embodiment, the anti-Dsg2 antibody, or fragment thereof comprises a heavy chain variable region having a sequence as set forth in SEQ ID NO:24, or a fragment or variant thereof. In one embodiment, the anti-Dsg2 antibody, or fragment thereof comprises a light chain variable region having a sequence as set forth in SEQ ID NO:32, or a fragment or variant thereof. In one embodiment, the anti-Dsg2 antibody, or fragment thereof comprises a heavy chain variable region sequence of SEQ ID NO:24, or a fragment or variant thereof, and a light chain variable region sequence of SEQ ID NO:32, or a fragment or variant thereof.

In some embodiments, a variant of an amino acid sequence as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared to a defined amino acid sequence. In some embodiments, a variant of an amino acid sequence as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over the full length of an amino acid sequence of SEQ ID NO:8, SEQ ID NO:16, SEQ ID NO:24, or SEQ ID NO:32.

In some embodiments, a fragment of an amino acid sequence as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length sequence of a defined amino acid sequence. In some embodiments, a fragment of an amino acid sequence as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length sequence SEQ ID NO:8, SEQ ID NO:16, SEQ ID NO:24, or SEQ ID NO:32.

As used herein, the term “antibody” or “immunoglobulin” refers to proteins (including glycoproteins) of the immunoglobulin (Ig) superfamily of proteins. An antibody or immunoglobulin (Ig) molecule may be tetrameric, comprising two identical light chain polypeptides and two identical heavy chain polypeptides. The two heavy chains are linked together by disulfide bonds, and each heavy chain is linked to a light chain by a disulfide bond. Each full-length Ig molecule contains at least two binding sites for a specific target or antigen.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, NY). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic affinity cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefore. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, NY).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid molecules encoding the Dsg2 binding molecule described herein may be cloned and sequenced using technology which is available in the art, and is described, for example, in Wright et al. (1992, Critical Rev. Immunol. 12:125-168), and the references cited therein. Further, the antibody of the invention may be “humanized” using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with Dsg2. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers (H2L2) formed of two dimers associated through at least one disulfide bridge.

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In one embodiment, the present invention provides a composition comprising an isolated nucleic acid encoding a Dsg2 binding molecule of the invention, or a biologically functional fragment thereof.

In one embodiment, the nucleic acid molecule encoding the anti-Dsg2 antibody, or fragment thereof, encodes 1, 2, 3, 4, 5, or all 6 of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, and a LC CDR3 sequence of SEQ ID NO:14. In one embodiment, the nucleic acid molecule encoding the anti-Dsg2 antibody, or fragment thereof, comprises 1, 2, 3, 4, 5, or all 6 of: a heavy chain (HC) CDR1 encoding sequence of SEQ ID NO:1, a HC CDR2 encoding sequence of SEQ ID NO:3, a HC CDR3 encoding sequence of SEQ ID NO:5, a light chain (LC) CDR1 encoding sequence of SEQ ID NO:9, a LC CDR2 encoding sequence of SEQ ID NO:11, and a LC CDR3 encoding sequence of SEQ ID NO:13.

In one embodiment, the nucleic acid molecule encoding the anti-Dsg2 antibody, or fragment thereof, encodes 1, 2, 3, 4, 5, or all 6 of: a heavy chain (HC) CDR1 sequence of SEQ ID NO:18, a HC CDR2 sequence of SEQ ID NO:20, a HC CDR3 sequence of SEQ ID NO:22, a light chain (LC) CDR1 sequence of SEQ ID NO:26, a LC CDR2 sequence of SEQ ID NO:28, and a LC CDR3 sequence of SEQ ID NO:30. In one embodiment, the nucleic acid molecule encoding the anti-Dsg2 antibody, or fragment thereof, comprises 1, 2, 3, 4, 5, or all 6 of: a heavy chain (HC) CDR1 encoding sequence of SEQ ID NO:17, a HC CDR2 encoding sequence of SEQ ID NO:19, a HC CDR3 encoding sequence of SEQ ID NO:21, a light chain (LC) CDR1 encoding sequence of SEQ ID NO:25, a LC CDR2 encoding sequence of SEQ ID NO:27, and a LC CDR3 encoding sequence of SEQ ID NO:29.

In one embodiment, the nucleic acid molecule encoding the anti-Dsg2 antibody, or fragment thereof, encodes a heavy chain variable region having a sequence as set forth in SEQ ID NO:8, or a fragment or variant thereof. In one embodiment, the nucleic acid molecule encoding the anti-Dsg2 antibody, or fragment thereof, encodes a light chain variable region having a sequence as set forth in SEQ ID NO:16, or a fragment or variant thereof. In one embodiment, the nucleic acid molecule encoding the anti-Dsg2 antibody, or fragment thereof, encodes a heavy chain variable region sequence of SEQ ID NO:8, or a fragment or variant thereof, and a light chain variable region sequence of SEQ ID NO:16, or a fragment or variant thereof.

In one embodiment, the nucleic acid molecule encoding the anti-Dsg2 antibody, or fragment thereof, comprises a nucleotide sequence as set forth in SEQ ID NO:7, or a fragment or variant thereof, encoding a heavy chain variable region. In one embodiment, the nucleic acid molecule encoding the anti-Dsg2 antibody, or fragment thereof, comprises a nucleotide sequence as set forth in SEQ ID NO:15, or a fragment or variant thereof, encoding light chain variable region. In one embodiment, the nucleic acid molecule encoding the anti-Dsg2 antibody, or fragment thereof, comprises a nucleotide sequence as set forth in SEQ ID NO:7, or a fragment or variant thereof, encoding a heavy chain variable region, and nucleotide sequence as set forth in SEQ ID NO:15, or a fragment or variant thereof, encoding light chain variable region.

In one embodiment, the nucleic acid molecule encoding the anti-Dsg2 antibody, or fragment thereof, encodes a heavy chain variable region having a sequence as set forth in SEQ ID NO:24, or a fragment or variant thereof. In one embodiment, the nucleic acid molecule encoding the anti-Dsg2 antibody, or fragment thereof, encodes a light chain variable region having a sequence as set forth in SEQ ID NO:32, or a fragment or variant thereof. In one embodiment, the nucleic acid molecule encoding the anti-Dsg2 antibody, or fragment thereof, encodes a heavy chain variable region sequence of SEQ ID NO:24, or a fragment or variant thereof, and a light chain variable region sequence of SEQ ID NO:32, or a fragment or variant thereof.

In one embodiment, the nucleic acid molecule encoding the anti-Dsg2 antibody, or fragment thereof, comprises a nucleotide sequence as set forth in SEQ ID NO:23, or a fragment or variant thereof, encoding a heavy chain variable region. In one embodiment, the nucleic acid molecule encoding the anti-Dsg2 antibody, or fragment thereof, comprises a nucleotide sequence as set forth in SEQ ID NO:31, or a fragment or variant thereof, encoding light chain variable region. In one embodiment, the nucleic acid molecule encoding the anti-Dsg2 antibody, or fragment thereof, comprises a nucleotide sequence as set forth in SEQ ID NO:23, or a fragment or variant thereof, encoding a heavy chain variable region, and nucleotide sequence as set forth in SEQ ID NO:31, or a fragment or variant thereof, encoding light chain variable region.

In some embodiments, a variant of a nucleotide sequence as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared to a defined nucleotide sequence. In some embodiments, a variant of a nucleotide sequence as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over the full length of a nucleotide sequence of SEQ ID NO:7, SEQ ID NO:15, SEQ ID NO:23, or SEQ ID NO:31.

In some embodiments, a fragment of a nucleotide sequence as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length sequence of a defined nucleotide sequence. In some embodiments, a fragment of a nucleotide sequence as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length nucleotide sequence of SEQ ID NO:7, SEQ ID NO:15, SEQ ID NO:23, or SEQ ID NO:31.

The isolated nucleic acid sequence encoding the antigenic protein or peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding the antigenic protein or peptide, or functional fragment thereof. In one embodiment, the composition comprises an isolated RNA molecule encoding the antigenic protein or peptide, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In some backbone-modified ribonucleotides the phosphoester group connecting to adjacent ribonucleotides is replaced by a modified group, e.g., of phosphothioate group. In some sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some embodiments, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example, as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, for example, different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In some embodiments, the expression of natural or synthetic nucleic acids encoding a Dsg2 binding molecule is typically achieved by operably linking a nucleic acid encoding the antigenic protein or peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a Dsg2 binding molecule, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). In one embodiment, the method of introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising a Dsg2 binding molecule, or a nucleic acid molecule encoding a Dsg2 binding molecule. Exemplary delivery vehicles include, but are not limited to, microspheres, microparticles, nanoparticles, polymersomes, liposomes, and micelles. For example, in certain embodiments, the delivery vehicle is loaded with a Dsg2 binding molecule, or a nucleic acid molecule encoding a Dsg2 binding molecule. In certain embodiments, the delivery vehicle provides for controlled release, delayed release, or continual release of its loaded cargo. In certain embodiments, the delivery vehicle comprises a targeting moiety that targets the delivery vehicle to a treatment site.

Immunotherapeutic Compositions

In some embodiments, the present invention relates to immunotherapy and specifically to targeted cell therapies based on genetically engineering immune cells to express a transgene under desired conditions. In some embodiments, the transgene encodes a Dsg2 binding molecule, or a fragment thereof. Described herein is a method for generating immune cells for immunotherapy by targeting the integration of a therapeutic transgene into the genome of an immune cell such that the transgene is placed under control of an endogenous promoter. It will be understood that reference to a transgene (in the singular) as described herein applies also to one or more transgenes (in the plural) unless context indicates otherwise. The invention provides a strategy for immune cell therapy that utilizes genome editing to place one or several therapeutic transgenes under the control of one or more endogenous promoters to provide controlled spatio-temporal expression in therapeutic immune cells. The invention provides for an immune cell to be engineered to express a therapeutic transgene, or a variety of therapeutic transgenes, where expression of the transgene can be made dependent on the location of the immune cell (e.g., expression of a transgene only in proximity to a tumor), or at defined time points (e.g., before or after engaging a tumor cell) by use of endogenous promoters that provide for expression accordingly. The cells and methods of the invention can thus be used to increase the efficacy and safety of therapeutic immune cells.

In one embodiment, the immune cell of the invention is a T cell, B cell, NK cell, antigen-presenting cell (e.g., dendritic cell or macrophage), monocyte, neutrophil, eosinophil, or basophil.

In some embodiments, the invention relates to placing a therapeutic transgene under control of an endogenous promoter to achieve a desired transgene expression profile in the immune cell. An endogenous promoter is selected so as to regulate the expression characteristics of the transgene, for example, the timing of transgene expression and/or the level of transgene expression. Regulating expression of the transgene by placing it under control of an endogenous promoter eliminates the need for administering small molecule drugs to induce expression of a transgene, immunogenic components, and viral vectors encoding internal promoters and transgenes. By utilizing endogenous promoters, the immune cells are engineered to autonomously regulate expression of transgenes such that transgene expression, for example, where and when transgene expression is activated, preferably occurs in a defined program that relies on the coordinated endogenous response of the immune cell to environmental cues (e.g., proximity to a target antigen, cytokine, and/or costimulatory ligand). Thus, in a specific embodiment, the immune cell is engineered such that an endogenous promoter is used that responds to micro-environmental cues, resulting in spatially and temporally predictable transgene expression governed by the endogenous promoter.

In a specific embodiment, the therapeutic transgene encodes a therapeutic protein. In another specific embodiment, the therapeutic transgene encodes a therapeutic RNA.

Immune Cells

In one embodiment, the invention provides an immune cell comprising a Dsg2 binding molecule of the invention. In one embodiment, the invention provides an immune cell (e.g., a T cell), comprising a recombinant nucleic acid sequence encoding a chimeric antigen receptor (CAR). In one embodiment, the recombinant cells can be used to enhance or provide an immune response against a Dsg2-expressing cell. In some embodiments, the cells are derived from a human (are of human origin prior to being made recombinant) (and human-derived cells are particularly preferred for administration to a human in the methods of treatment of the invention).

In some embodiments, T cells useful as immune cells of the invention can be CD4+ or CD8+ and can include, but are not limited to, T helper cells (CD4+), cytotoxic T cells (also referred to as cytotoxic T lymphocytes, CTL; CD8+ T cells), and memory T cells, including central memory T cells (TCM), stem memory T cells (TSCM), stem-cell-like memory T cells (or stem-like memory T cells), and effector memory T cells, for example, $T_{EM}$ cells and $T_{EMRA}$ (CD45RA+) cells, effector T cells, Th1 cells, Th2 cells, Th9 cells, Th17 cells, Th22 cells, Tfh (follicular helper) cells, T regulatory cells, natural killer T cells, mucosal associated invariant T cells (MATT), and γδ T cells. Major T cell subtypes include $T_N$ (naive), $T_{SCM}$ (stem cell memory), $T_{CM}$ (central memory), $T_{TM}$ (Transitional Memory), $T_{EM}$ (Effector memory), and $T_{TE}$ (Terminal Effector), TCR-transgenic T cells, T-cells redirected for universal cytokine-mediated killing (TRUCK), Tumor infiltrating T cells (TIL), CAR-T cells or any T cell that can be used for treating a disease or disorder.

In one embodiment, the T cells of the invention are immunostimulatory cells, i.e., cells that mediate an immune response. Exemplary T cells that are immunostimulatory include, but are not limited to, T helper cells (CD4+), cytotoxic T cells (also referred to as cytotoxic T lymphocytes, CTL; CD8+ T cells), and memory T cells, including central memory T cells (TCM), stem memory T cells (TSCM), stem-cell-like memory T cells (or stem-like memory T cells), and effector memory T cells, for example, TEM cells and TEMRA (CD45RA+) cells, effector T cells, Th1 cells, Th2 cells, Th9 cells, Th17 cells, Th22 cells, Tfh (follicular helper) cells, natural killer T cells, mucosal associated invariant T cells (MATT), and γδ T cells.

Immune cells can optionally be generated from embryonic stem cells or induced pluripotent stem cells (iPSCs). In some embodiments, precursor cells of immune cells that can be used, which recombinantly express a Dsg2 binding molecule (e.g. a CAR) of the invention, are, by way of example, hematopoietic stem and/or progenitor cells. Hematopoietic stem and/or progenitor cells can be derived from bone marrow, umbilical cord blood, adult peripheral blood after cytokine mobilization, and the like, by methods known in the art, and then are genetically engineered to recombinantly express a Dsg2 binding molecule (e.g. a CAR) of the invention. In some embodiments, precursor cells are those that can differentiate into the lymphoid lineage, for example, hematopoietic stem cells or progenitor cells of the lymphoid lineage that can differentiate into the desired immune cell types. In one embodiment, an iPSC can be utilized as a cell for expression of a Dsg2 binding molecule (e.g. a CAR) of the invention.

Immune cells can be isolated by methods well known in the art, including commercially available isolation methods. Sources for the immune cells include, but are not limited to, peripheral blood, umbilical cord blood, bone marrow, or other sources of hematopoietic cells. Various techniques can be employed to separate the cells to isolate or enrich for desired immune cells, such as T cells. For instance, negative selection methods can be used to remove cells that are not the desired immune cells. Additionally, positive selection methods can be used to isolate or enrich for desired T cells, or a combination of positive and negative selection methods can be employed. Monoclonal antibodies (MAbs) are particularly useful for identifying markers associated with particular cell lineages and/or stages of differentiation for both positive and negative selections. If a particular type of T cell is to be isolated, various cell surface markers or combinations of markers, including but not limited to, CD3, CD4, CD8, CD34 (for hematopoietic stem and progenitor cells) and the like, can be used to separate the cells, as is well known in the art.

Procedures for separation of cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique.

The immune cells can be autologous or non-autologous to the subject to which they are administered in the methods of treatment of the invention. Autologous cells are isolated from the subject to which the engineered immune cells are to be administered. In one embodiment, autologous cells are isolated from the subject to which the engineered cells recombinantly expressing a CAR are to be administered. Optionally, the cells can be obtained by leukapheresis, where leukocytes are selectively removed from withdrawn blood, made recombinant, and then re-transfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. For both autologous and and non-autologous cells, the cells can optionally be cryopreserved until ready to be used for genetic manipulation and/or administration to a subject using methods well known in the art.

Various methods for isolating immune cells that can be used for recombinant expression of a CAR have been described previously, and can be used, including but not limited to, using peripheral donor lymphocytes (Sadelain et al., Nat. Rev. Cancer 3:35-45 (2003); Morgan et al., Science 314:126-129 (2006), using lymphocyte cultures derived from tumor infiltrating lymphocytes (TILs) in tumor biopsies (Panelli et al., J Immunol. 164:495-504 (2000); Panelli et al., J Immunol. 164:4382-4392 (2000)), and using selectively in vitro-expanded antigen-specific peripheral blood leukocytes employing artificial antigen-presenting cells (AAPCs) or dendritic cells (Dupont et al., Cancer Res. 65:5417-5427 (2005); Papanicolaou et al., Blood 102:2498-2505 (2003)). In the case of using stem cells, the cells can be isolated by methods well known in the art (see, for example, Klug et al., Hematopoietic Stem Cell Protocols, Humana Press, New Jersey (2002); Freshney et al., Culture of Human Stem Cells, John Wiley & Sons (2007)).

In one embodiment, isolated immune cells are genetically engineered ex vivo for recombinant expression of a Dsg2 binding molecule of the invention. In one embodiment, isolated immune cells are genetically engineered ex vivo for recombinant expression of a CAR. The cells can be genetically engineered for recombinant expression by methods well known in the art.

The immune cells can be subjected to conditions that favor maintenance or expansion of the cells. The cells can be expanded prior to or after ex vivo genetic engineering.

Expansion of the cells is particularly useful to increase the number of cells for administration to a subject. Such methods for expansion of immune cells, such as T cells, are well known in the art. Furthermore, the cells can be cryopreserved after isolation and/or genetic engineering, and/or expansion of genetically engineered cells. Methods for cyropreserving cells are well known in the art.

Recombinant Cells

In some embodiments the invention provides immune cells recombinantly expressing a Dsg2 binding molecule of the invention under control of an endogenous promoter. In one embodiment, a nucleic acid encoding the Dsg2 binding molecule (e.g., CAR) of the invention is introduced into the immune cell. Traditionally, such methods have utilized a suitable expression vector, in which case the immune cells are transduced with a transgene, for example, a nucleic acid encoding a CAR. In one embodiment, a t Dsg2 binding molecule (e.g., CAR) of the invention is cloned into a targeting construct, which provides for targeted integration of the transgene at a site within the genome. For example, a polynucleotide encoding a CAR of the invention can be cloned into a suitable targeting construct, or a suitable vector such as a retroviral vector, and introduced into the immune cell using well known molecular biology techniques.

Any suitable targeting construct suitable for expression in an immune cell of the invention (e.g., a human T cell) can be employed. In a particular embodiment, the targeting construct is compatible for use with a homologous recombination system suitable for targeted integration of the nucleic acid sequence (transgene) at a site within the genome of the cell. Exemplary homologous recombination systems are well known in the art and include, but are not limited to, technologies utilizing a nuclease, for example, transcription activator-like effector nucleases (TALENs), Zinc-finger nucleases (ZFNs), clustered regularly interspaced short palindromic repeats (CRISPRs) systems such as and CRISPR associated protein 9 (Cas9) and Cpf1, and/or Meganuclease or a Mega-Tal (fusion of a Tal domain and a Meganuclease) and the like, which provide for homologous recombination. Such methods are well known in the art and commercially available. Other CRISPR based systems include pyrogen and *Aureus*. Such methods can be used to carry out or promote homologous recombination.

Vectors and Targeting Constructs

Viral vectors that can be used for the methods of the invention include, but are not limited to, retroviral, adenoviral, lentiviral, and adeno-associated viral vectors, vaccinia virus, bovine papilloma virus derived vectors, and herpes virus vectors, such as Epstein-Barr Virus (see, for example, Miller, Hum. Gene Ther. 1(1):5-14 (1990); Friedman, Science 244:1275-1281 (1989); Eglitis et al., BioTechniques 6:608-614 (1988); Tolstoshev et al., Current Opin. Biotechnol. 1:55-61 (1990); Sharp, Lancet 337:1277-1278 (1991); Cornetta et al., Prog. Nucleic Acid Res. Mol. Biol. 36:311-322 (1989); Anderson, Science 226:401-409 (1984); Moen, Blood Cells 17:407-416 (1991); Miller et al., Biotechnology 7:980-990 (1989); Le Gal La Salle et al., Science 259:988-990 (1993); and Johnson, Chest 107:77S-83S (1995); Rosenberg et al., N. Engl. J. Med. 323:370 (1990); Anderson et al., U.S. Pat. No. 5,399,346; Scholler et al., Sci. Transl. Med. 4:132-153 (2012; Parente-Pereira et al., J. Biol. Methods 1(2):e7 (1-9)(2014); Lamers et al., Blood 117(1):72-82 (2011); Reviere et al., Proc. Natl. Acad. Sci. USA 92:6733-6737 (1995); Wang et al., Gene Therapy 15:1454-1459 (2008)).

In some embodiments, the vectors are recombinant Adeno-Associated Virus (rAAV), recombinant non-integrating lentivirus (rNILV), recombinant non-integrating gamma-retrovirus (rNIgRV), single-stranded DNA (linear or circular), and the like.

In methods of the present invention that employ an endogenous promoter for controlling the expression of a transgene that is integrated within a site in the genome of a cell, the targeting construct preferably is promoter-less.

In some embodiments, a vector that employs a suitable promoter for expression of a Dsg2 binding molecule (e.g., a CAR) of the invention in an immune cell can be utilized. The promoter can be an inducible promoter or a constitutive promoter.

In some embodiments, the constructs of the invention can be designed to include a P2A sequence directly upstream of the nucleic acid sequences encoding the transgene. In one embodiment, the targeting construct can optionally be designed to include a P2A sequence directly upstream of the nucleic acid sequences encoding a CAR. P2A is a self-cleaving peptide sequence, which can be used for bicistronic or multicistronic expression of protein sequences (see Szymczak et al., Expert Opin. Biol. Therapy 5(5):627-638 (2005)). If desired, the construct can optionally be designed to include a reporter, for example, a reporter protein that provides for identification of transduced cells. Exemplary reporter proteins include, but are not limited to, fluorescent proteins, such as mCherry, green fluorescent protein (GFP), blue fluorescent protein, for example, EBFP, EBFP2, Azurite, and mKalamal, cyan fluorescent protein, for example, ECFP, Cerulean, and CyPet, and yellow fluorescent protein, for example, YFP, Citrine, Venus, and YPet.

In some embodiments, the construct comprises a polyadenylation (poly A) sequence 3' of the transgene. For example, in one embodiment, the construct comprises a polyadenylation (poly A) sequence 3' of the nucleic acid sequences encoding a CAR.

Assays can be used to determine the transduction efficiency of a transgene, preferably encoding a CAR, using routine molecular biology techniques. Gene transfer efficiency can be monitored by fluorescence activated cell sorting (FACS) analysis to quantify the fraction of transduced immune cells, and/or by quantitative PCR. Using a well-established cocultivation system (Gade et al., Cancer Res. 65:9080-9088 (2005); Gong et al., Neoplasia 1:123-127 (1999); Latouche et al., Nat. Biotechnol. 18:405-409 (2000)) it can be determined whether fibroblast AAPCs expressing cancer antigen (vs. controls) direct cytokine release from transduced immune cells expressing a CAR (cell supernatant LUMINEX (Austin Tex.) assay for IL-2, IL-4, IL-10, IFN-γ, TNF-α, and GM-CSF), immune cell proliferation (by carboxyfluorescein succinimidyl ester (CFSE) labeling), and immune cell survival (by Annexin V staining). Immune cells expressing a CAR can be exposed to repeated stimulation by target antigen positive cells, and it can be determined whether immune cell proliferation and cytokine response remain similar or diminished with repeated stimulation. In one embodiment, immune cells expressing a CAR can be exposed to repeated stimulation by cancer antigen positive target cells, and it can be determined whether immune cell proliferation and cytokine response remain similar or diminished with repeated stimulation. Cytotoxicity assays with multiple E:T ratios can be conducted using chromium-release assays.

In some embodiments, the invention relates to expressing a therapeutic transgene in an immune cell by integrating the transgene at a site within the genome of the immune cell such that the transgene is placed under the control of an endogenous promoter of the immune cell. By utilizing an endogenous promoter, immune cells are engineered to express a therapeutic transgene, or a variety of therapeutic transgenes under the control of different endogenous promoters. In a specific embodiment, expression of the transgene is dependent on the microenvironment of the immune cell. For example, expression of a therapeutic transgene can be made dependent on the location of the immune cell (e.g., expression of a transgene only in proximity to a tumor) by using an endogenous promoter that is induced when the immune cell is at a particular location (e.g., when the immune cell is at the location of a tumor and is activated by binding to tumor antigen, thereby inducing the endogenous promoter), or can be at defined time points (e.g., by using an endogenous promoter that is induced at a defined time point, e.g. by activation of the immune cell upon encountering a tumor cell). The promoter is selected based on, for example, how soon it is activated or inhibited after encounter of the immune cell with an antigen, how strongly it is expressed, and for how long. The promoter is selected to accommodate the pharmacology for the transgene whose expression it regulates (e.g., some transgenes are more effective at low levels, other transgenes are more effective at high levels of expression, and the like). It will be understood that the description in this disclosure with respect to use of an endogenous promoter (singular) controlling the expression of a transgene in an immune cell will apply equally to the use of more than one endogenous promoter, each controlling the expression of a transgene (that can be the same or different from the other transgenes), in the immune cell, unless context indicates otherwise. One skilled in the art can readily select appropriate endogenous promoters to provide desired expression and/or regulation of one or more transgenes to enhance the effectiveness of a immune cell for use in immune cell therapy.

The endogenous immune cell promoters can be constitutive or inducible. In a specific embodiment, the endogenous promoter is specific for a subset of immune cells. In the case where more than one transgene is expressed in an immune cell, the transgenes (which may be different from each other) can be placed under control of a combination of constitutive and inducible promoters, respectively, of which one or more can be, for example, specific for a subset of immune cells.

In one embodiment, the endogenous immune cell promoter is constitutive. In another embodiment, the endogenous immune cell promoter is inducible. In a specific embodiment, the endogenous immune cell promoter is active in a subset of immune cells. In one embodiment, two or more transgenes are integrated into the genome of the immune cell, such that expression of each transgene is under the control of a different endogenous promoter of the immune cell. In a specific embodiment, two transgenes are thus integrated. In a particular embodiment, the expression of each of two transgenes is under the control of different endogenous promoters that are constitutive. In another particular embodiment, the expression of each of two transgenes is under the control of different endogenous promoters that are inducible. In another particular embodiment, the expression of a first transgene is under control of a constitutive endogenous promoter and expression of a second transgene is under control of an inducible endogenous promoter. In another particular embodiment, three transgenes are integrated into the genome of the immune cell, such that expression of each transgene is under the control of a different endogenous promoter of the immune cell, where expression of a first transgene is under control of a constitutive endogenous promoter and expression of second and third transgenes is under control of two different inducible, endogenous promoters, respectively. It is understood that, depending on the transgene to be expressed in the immune cell, a promoter can be selected to provide an appropriate expression level, time of expression, expression when the immune cell is in a particular microenvironment, and so forth. For example, expression of transgene 1 can be under control of a constitutive promoter, expression of transgene 2 can be under control of an inducible promoter that is activated shortly after contact with an antigen recognized by the immune cell, and expression of transgene 3 can be under control of a different inducible promoter that is activated at a later time or at a different level than for transgene 2. In this particular example, transgene 1 is expressed constitutively, and transgenes 2 and 3 are under control of inducible promoters with distinct characteristics.

Engineering of immune cells of the invention to express a transgene from an endogenous immune cell promoter provides for autonomous regulation of transgene expression by the immune cell. Thus, the microenvironment of the immune cell can be used to coordinate the expression of multiple transgenes to provide optimized activity of the transgenic immune cell, particularly when at least one gene is under control of an inducible promoter. For example, immune cell therapy can be accompanied by administration of an immune cell stimulatory cytokine (see Sadelain et al., Cancer Disc. 3:388-398 (2013)). In one embodiment, the immune cells of the invention can be engineered to co-express a CAR and a second transgene, such as an immune cell activating cytokine. For example, a CAR can be placed under control of a constitutive promoter, and a second transgene such as an immune cell activating cytokine (e.g., interleukin 12 (IL12)) can be placed under control of an inducible promoter such that activation of the inducible promoter controlling the second transgene occurs when the immune cell is in proximity to an antigen recognized by the CAR such as on a tumor, for example, when the immune cell engages a target tumor antigen by binding to the CAR. In this example, such a construct obviates the need for systemic or localized administration of an immune cell activating cytokine, which can result in toxicity. In addition, in the case where the immune cell is engineered to express a immune cell activation cytokine under control of an inducible promoter that can be regulated by administration of a drug, such a construct obviates the need to administer the drug. In such a case, instead of needing to administer a drug to induce expression of a transgene, regulation of transgene expression is under control of an endogenous promoter, which provides for expression of the transgene. Instead, the immune cell itself, upon engagement with a target antigen, activates expression of an immune cell activating cytokine, providing localized expression of the cytokine, and therefore spatio-temporal regulation of expression of transgenes to optimize the effectiveness of the immune cells to be used for immunotherapy.

In another example, an immune cell expressing a CAR can sometimes exhibit toxicities. To reduce such toxicity, in a specific embodiment, a transgene encoding a CAR can therefore be placed under control of an inducible promoter such that the promoter is not induced, and expression of the CAR does not occur, until the immune cell is engaged with a target recognized by the CAR, such as a target tumor. In yet another embodiment, an immune cell can be engineered to have higher selectivity for a particular target. For example, in some cases a target antigen on a tumor may not be expressed on the tumor only. Therefore, targeting of an immune cell to the target antigen could result in an immune response against non-target cells or tissues that express the same antigen. Accordingly, in one embodiment, an immune cell of the invention is engineered to recognize two antigens on a target tumor, which provides higher selectivity for the target tumor. For example, the immune cell can be engineered to express two CARs specific for two different tumor antigens. In this case, selective binding of the immune cell to a target bearing two target antigens can be coupled with a third transgene under control of an inducible endogenous promoter, such as an immune cell activating cytokine as described above, thereby stimulating activation of the immune cell with the cytokine only upon selective engagement with the target. A person skilled in the art will readily understand that selection of suitable therapeutic transgenes to be expressed under the control of suitable endogenous immune cell promoters, either constitutive, specific for a subtype of immune cells, inducible, or a combination thereof, can be used to generate autonomously regulated expression of transgenes to provide more effective immune cell therapy. In one embodiment, instead of using a fully competent CAR targeting one antigen, two sub-optimal CAR targeting two different antigens need to be engaged for a full antitumor response. If healthy tissues express one or the other antigen, the healthy tissue will not fully engage a CAR immune cell response. If the tumor expresses the two antigens, it will then trigger a complete CAR immune cell activity.

In some embodiments, the transgenic immune cells of the invention comprise both constitutive and inducible promoters, since an immune cell can be engineered to specifically respond to a particular molecular cue to produce new therapeutic molecules at a chosen location and time. For example, a transgene encoding an antigen-specific cell-surface receptor (e.g., a Dsg2 binding molecule of the invention) can be expressed from a constitutive promoter and will only signal upon interaction with that particular antigen. Then, this interaction induces the activation of a specific promoter that controls the expression of a therapeutic molecule. The therapeutic benefit of this particular engineered immune cell depends on the function of both constitutive and inducible promoters. For example, in such a case, the transgene would be expressed upon CAR activation and specifically be expressed in the tumor.

In one embodiment, the invention relates to expressing 3 transgenes, or more. For example, transgene 1 can be constitutive, and 2 or more additional transgene can come in shortly after contact with antigen. In a particular embodiment, transgene 1 encodes a CAR specific for Dsg2. After binding to Dsg2, one or more additional transgene is expressed. In one embodiment, the one or more additional transgene encodes another CAR specific for an antigen also expressed on tumor cells or on other cells within the tumor microenvironment. This example is a form of "combinatorial targeting" using temporal/sequential expression of different CARs by the same immune cell. In another particular embodiment, transgene 1 encodes a CAR specific for Dsg2; transgene 2 encodes a cytokine, and transgene 3 encodes another cytokine or a costimulatory ligand or an scFv, for example, recognizing an antigen on the same cells (e.g., tumor cells) that express antigen A or cells in the same microenvironment. This is an example of sequential gene activation designed to increase immune cell potency and safety by confining gene expression to a microenvironment such as the tumor microenvironment.

In one embodiment, the inducible promoter is induced by activation of the immune cell. In one embodiment, the inducible promoter is induced by binding of a chimeric antigen receptor (CAR) or a chimeric co-stimulatory receptor (CCR) expressed by the immune cell to its respective binding partner, for example, upon interaction with its corresponding antigen. Both CARs and CCRs contain intracellular signaling domains. In the case of a CAR, the intracellular signaling domain activates an immune cell, and optionally contains a co-stimulatory domain (in the case of second and third generation CARs) (see Sadelain et al., Cancer Discov. 3(4):388-398 (2013)). In the case of a CCR, it contains a co-stimulatory signal but does not have an immune cell activation signal (Sadelain et al., supra, 2013). Binding of a corresponding antigen to a CAR or CCR results in activation of the immune cell signaling domain and/or the co-stimulatory domain. The activation of these signaling domains results in propagation of a signal to the nucleus and activation of certain endogenous promoters in the immune cell. Intracellular signaling domains of a CAR or CCR include, but are not limited to, the intracellular domains of CD28, 4-1BB, CD27, ICOS, CD3, and the like, as well as other intracellular signaling domains disclosed herein. Signaling can also occur with mutated (e.g, mutated ITAMs), truncated or fused versions of these domains.

In another embodiment, the inducible promoter is induced by binding of the T cell receptor (TCR), CD28, CD27, 4-1BB, and the like, expressed by the immune cell to its respective binding partner. These molecules contain intracellular signaling domains. Upon activation, the signaling domain results in propagation of a signal to the nucleus and activation of certain endogenous promoters in the immune cell. In another embodiment, the inducible promoter is induced by binding of an iCAR (CAR with inhibitory intracellular domain such as PD1, CTLA4) or truncated CAR (no intracellular domain). In one embodiment, the iCAR functions as a 'break' for the immune cells activation upon target encounter through the signaling of CTLA4 or PD1 intracellular domains. Thus promoters that are regulated by PD1 or CTLA4 can be used to express a transgene upon iCAR encounter with the antigen.

In another embodiment, the inducible promoter is induced by binding of a ligand to an inhibitory receptor expressed on the immune cell. Exemplary inhibitory receptors include, but are not limited to, the receptors programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), tumor necrosis factor (TNF)-related apoptosis-inducing ligand (TRAIL, receptors 1 and 2), Fas, T-cell immunoreceptor with Ig and ITIM domains (TIGIT), and 2B4 (CD244). The corresponding ligands for these inhibitory receptors include, for example, PD-L1 (for PD-1); PD-L2 (for PD-1); CD80, CD86 (for CTLA-4); HVEM (for BTLA); Galectin-9, HMGB1 (for TIM-3); MHC II (for LAG-3); TRAIL (for TRAIL receptor 1 and TRAIL receptor 2); Fas ligand (FasL) (for Fas), and the like (see Chen et al., Nat. Rev. Immunol. 13(4):227-242 (2013); Tollefson et al., J. Virol. 75:8875-8887 (2001); Waring et al., Immunol. Cell Biol. 77:312-317 (1999)).

In another embodiment, the inducible promoter is induced by binding of a cytokine to a cytokine receptor expressed by the immune cell. In one embodiment, the cytokine is an immunostimulatory cytokine selected from the group consisting of interleukin 2 (IL2), interleukin 7 (IL7), interleukin 15 (IL15), and interleukin 21 (IL21).

In another embodiment, the inducible promoter is induced by a metabolite. In a particular embodiment, the metabolite is selected from the group consisting of pyruvate, glutamine, beta-hydroxybutyrate, lactate, and serine. These metabolites are generated or taken up during immune cell activation, which translates into a metabolic change in the immune cell.

In another embodiment, the inducible promoter is induced by a metabolic change. This refers to the metabolic state of the cells. For example, when naive T cells rely on oxidative phosphorylation to generate energy, and when they became activated and differentiate into effector T cell, they switch to glycolysis to generate energy. Hypoxia and low-pH also induce metabolic changes (Chang et al., Nat. Immunol 17:364-368 (2016); McNamee et al., Immunol. Res. 55: 58-70 (2013)).

In another embodiment, the inducible promoter is induced by an ion, such as a particular ion concentration. In one embodiment, the ion is potassium or calcium. Exemplary promoters induced by an ion include, but are not limited to the promoters of, IL2, TNFalpha, and IFNgamma, which are activated in a NFAT-dependent manner. NFAT is activated by increased levels of intracellular calcium.

Therapeutic Transgenes

The invention relates to compositions for expressing a therapeutic transgene in an immune cell. A therapeutic transgene is a nucleotide (e.g., DNA or a modified form thereof) sequence encoding a therapeutic protein or therapeutic nucleic acid. The therapeutic protein or therapeutic nucleic acid when expressed by the immune cell has use in treating a disease or disorder. The therapeutic protein can be an RNA, a peptide or polypeptide.

It is understood that a transgene can encode, for example, a cDNA, a gene, miRNA or lncRNA, or the like. Additionally, the transgene can be a polycistronic message, i.e., arrayed cDNAs or arrayed miRNAs. One exemplary polycistronic transgene is the TCR chains. Polycistronic messages can be engineered in the immune cells to express multiple transgenes under control of the same endogenous promoter. Thus, by knocking 3 bicistronic transgenes at 3 selected loci, one could express 6 gene products in an engineered immune cell. Thus, a number of transgenes can be expressed in an immune cell (1, 2, 3, 4, 5, 6 and so forth, as desired), each under control of separate endogenous promoters, or with some transgenes (i.e., polycistronic transgenes) under the control of the same endogenous promoter. The multiple transgenes can be placed independently under the control of a constitutive promoter or inducible. Thus, a combination of constitutive and/or inducible promoters can be used in an immune cell to express multiple transgenes in the same cell.

In one embodiment, the transgene is polycistronic, e.g., bicistronic. In one embodiment, the transgene is polycistronic and encodes more than one therapeutic protein or therapeutic RNA, where expression of both are under the control of the same endogenous promoter of the immune cell. In a specific embodiment, the transgene is bicistronic and encodes two therapeutic proteins (for example, scFvs), wherein the expression of the scFvs are both under the control of the same endogenous promoter of the immune cell.

Chimeric Antigen Receptors (CARs)

In one embodiment, the Dsg2 binding molecule of the invention comprises a chimeric antigen receptor (CAR). In some embodiments, the CAR comprises an antigen binding domain that binds to Dsg2.

In various embodiments, the CAR can be any CAR molecule including, but not limited to, a "first generation," "second generation," "third generation," "fourth generation" or "fifth generation" CAR (see, for example, Sadelain et al., Cancer Discov. 3(4):388-398 (2013); Jensen et al., Immunol. Rev. 257:127-133 (2014); Sharpe et al., Dis. Model Mech. 8(4):337-350 (2015); Brentjens et al., Clin. Cancer Res. 13:5426-5435 (2007); Gade et al., Cancer Res. 65:9080-9088 (2005); Maher et al., Nat. Biotechnol. 20:70-75 (2002); Kershaw et al., J. Immunol. 173:2143-2150 (2004); Sadelain et al., Curr. Opin. Immunol. (2009); Hollyman et al., J. Immunother. 32:169-180 (2009)).

"First generation" CARs for use in the invention comprise a Dsg2 binding domain, for example, a single-chain variable fragment (scFv), fused to a transmembrane domain, which is fused to a cytoplasmic/intracellular domain of a T cell receptor chain. "First generation" CARs typically have the intracellular domain from the CD3-chain, which is the primary transmitter of signals from endogenous T cell receptors (TCRs). "First generation" CARs can provide de novo antigen recognition and cause activation of both CD4+ and CD8+ T cells through their CD3ζ chain signaling domain in a single fusion molecule, independent of HLA-mediated antigen presentation.

"Second-generation" CARs for use in the invention comprise a Dsg2 binding domain, for example, a single-chain variable fragment (scFv), fused to an intracellular signaling domain capable of activating T cells and a co-stimulatory domain designed to augment T cell potency and persistence (Sadelain et al., Cancer Discov. 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory molecules, for example, CD28, 4-1BB, ICOS, OX40, and the like, in the cytoplasmic tail of the CAR to provide additional signals to the cell.

"Second generation" CARs provide both co-stimulation, for example, by CD28 or 4-1BB domains, and activation, for example, by a CD3ζ signaling domain. Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL) (Davila et al., Oncoimmunol. 1(9):1577-1583 (2012)).

"Third generation" CARs provide multiple co-stimulation, for example, by comprising both CD28 and 4-1BB domains, and activation, for example, by comprising a CD3ζ activation domain.

"Fourth generation" CARs provide co-stimulation, for example, by CD28 or 4-1BB domains, and activation, for example, by a CD3ζ signaling domain in addition to a constitutive or inducible chemokine component.

"Fifth generation" CARs provide co-stimulation, for example, by CD28 or 4-1BB domains, and activation, for example, by a CD3ζ signaling domain, a constitutive or inducible chemokine component, and an intracellular domain of a cytokine receptor, for example, IL-2Rβ.

In various embodiments, the CAR can be included in a multivalent CAR system, for example, a DualCAR or "TandemCAR" system. Multivalent CAR systems include systems or cells comprising multiple CARs and systems or cells comprising bivalent/bispecific CARs targeting more than one antigen.

In the embodiments disclosed herein, the CARs generally comprise a Dsg2 antigen binding domain, a transmembrane domain and an intracellular domain, as described above. In a particular non-limiting embodiment, the Dsg2-binding domain is an scFv.

As disclosed herein, the methods of the invention involve administering cells that have been engineered to express a CAR. The extracellular antigen-binding domain of a CAR is usually derived from a monoclonal antibody (mAb) or from receptors or their ligands.

A CAR directed to a Dsg2 can be generated using well known methods for designing a CAR, including those as described herein. A CAR, whether a first, second, third, fourth or fifth generation CAR, can be readily designed by fusing an antigen binding domain, or Dsg2 binding molecule, such as a Dsg2-scFv antibody, to an immune cell signaling domain, such as a T cell receptor cytoplasmic/intracellular domain. As described above, the CAR generally has the structure of a cell surface receptor, with the antigen binding activity, such as an scFv, as at least a portion of the extracellular domain, fused to a transmembrane domain, which is fused to an intracellular domain that has cell signaling activity in a T cell. The CAR can include co-stimulatory molecules, as described herein. One skilled in the art can readily select appropriate transmembrane domains, as described herein and known in the art, and intracellular domains to provide the desired signaling capability in the T cell.

In one embodiment, the antigen binding domain, or Dsg2 binding molecule, of the CAR of the invention comprises an antibody or fragment thereof. The antibody can be expressed as an immunoglobulin, for example, an IgG, or as a Bi-specific T-cell engager (BiTE), a diabody, a duel affinity re-targeting antibody (DART), a Fab, a F(ab'), a single chain variable fragment (scFv), a nanobody, a bi-specific antibody, or the like.

In some embodiments, the antigen binding domain, or Dsg2 binding molecule, can be an scFv or a Fab, or any suitable antigen binding fragment of an antibody (see Sadelain et al., Cancer Discov. 3:38-398 (2013)). Many antibodies or antigen binding domains derived from antibodies that bind to an antigen, such as a cancer antigen, are known in the art. Alternatively, such antibodies or antigen binding domains can be produced by routine methods. Methods of generating an antibody are well known in the art, including methods of producing a monoclonal antibody or screening a library to obtain an antigen binding polypeptide, including screening a library of human Fabs (Winter and Harris, Immunol. Today 14:243-246 (1993); Ward et al., Nature 341:544-546 (1989); Harlow and Lane, Antibodies: A Laboratory Manual, Cold Spring Harbor Laboratory Press (1988); Hilyard et al., Protein Engineering: A practical approach (IRL Press 1992); Borrabeck, Antibody Engineering, 2nd ed. (Oxford University Press 1995); Huse et al., Science 246:1275-1281 (1989)). For the CAR, the antigen binding domain derived from an antibody can be human, humanized, chimeric, CDR-grafted, and the like, as desired. For example, if a mouse monoclonal antibody is a source antibody for generating the antigen binding domain of a CAR, such an antibody can be humanized by grafting CDRs of the mouse antibody onto a human framework (see Borrabeck, supra, 1995), which can be beneficial for administering the CAR to a human subject. In a preferred embodiment, the antigen binding domain is an scFv. The generation of scFvs is well known in the art (see, for example, Huston, et al., Proc. Nat. Acad. Sci. USA 85:5879-5883 (1988); Ahmad et al., Clin. Dev. Immunol. 2012: ID980250 (2012); U.S. Pat. Nos. 5,091,513, 5,132,405 and 4,956,778; and U.S. Patent Publication Nos. 20050196754 and 20050196754)).

Well known methods can be used for generating and screening for an antibody that binds to Dsg2, as disclosed herein, including the generation of an scFv that binds to Dsg2, which is particularly useful in a CAR.

In one embodiment, the invention relates to compositions comprising Dsg2-directed CAR molecule, or fragment thereof. In one embodiment, the Dsg2-directed CAR molecule, or fragment thereof, comprises 1, 2, 3, 4, 5, or all 6 of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, and a LC CDR3 sequence of SEQ ID NO:14. In one embodiment, the Dsg2-directed CAR molecule, or fragment thereof, comprises 1, 2, 3, 4, 5, or all 6 of: a heavy chain (HC) CDR1 sequence of SEQ ID NO:18, a HC CDR2 sequence of SEQ ID NO:20, a HC CDR3 sequence of SEQ ID NO:22, a light chain (LC) CDR1 sequence of SEQ ID NO:26, a LC CDR2 sequence of SEQ ID NO:28, and a LC CDR3 sequence of SEQ ID NO:30.

In one embodiment, the Dsg2-directed CAR molecule, or fragment thereof comprises a heavy chain variable region having a sequence as set forth in SEQ ID NO:8, or a fragment or variant thereof. In one embodiment, the Dsg2-directed CAR molecule, or fragment thereof comprises a light chain variable region having a sequence as set forth in SEQ ID NO:16, or a fragment or variant thereof. In one embodiment, the Dsg2-directed CAR molecule, or fragment thereof comprises a heavy chain variable region sequence of SEQ ID NO:8, or a fragment or variant thereof, and a light chain variable region sequence of SEQ ID NO:16, or a fragment or variant thereof.

In one embodiment, the Dsg2-directed CAR molecule, or fragment thereof comprises a heavy chain variable region having a sequence as set forth in SEQ ID NO:24, or a fragment or variant thereof. In one embodiment, the Dsg2-directed CAR molecule, or fragment thereof comprises a light chain variable region having a sequence as set forth in SEQ ID NO:32, or a fragment or variant thereof. In one embodiment, the Dsg2-directed CAR molecule, or fragment thereof comprises a heavy chain variable region sequence of SEQ ID NO:24, or a fragment or variant thereof, and a light chain variable region sequence of SEQ ID NO:32, or a fragment or variant thereof.

In one embodiment, the invention relates to a nucleic acid molecule encoding a Dsg2-directed CAR molecule, or fragment thereof. In one embodiment, the nucleic acid molecule encoding the Dsg2-directed CAR molecule, or fragment thereof, encodes 1, 2, 3, 4, 5, or all 6 of: a heavy chain (HC) CDR1 sequence of SEQ ID NO:2, a HC CDR2 sequence of SEQ ID NO:4, a HC CDR3 sequence of SEQ ID NO:6, a light chain (LC) CDR1 sequence of SEQ ID NO:10, a LC CDR2 sequence of SEQ ID NO:12, and a LC CDR3 sequence of SEQ ID NO:14. In one embodiment, the nucleic acid molecule encoding the Dsg2-directed CAR molecule, or fragment thereof, comprises 1, 2, 3, 4, 5, or all 6 of: a heavy chain (HC) CDR1 encoding sequence of SEQ ID NO:1, a HC CDR2 encoding sequence of SEQ ID NO:3, a HC CDR3 encoding sequence of SEQ ID NO:5, a light chain (LC) CDR1 encoding sequence of SEQ ID NO:9, a LC CDR2 encoding sequence of SEQ ID NO:11, and a LC CDR3 encoding sequence of SEQ ID NO:13.

In one embodiment, the nucleic acid molecule encoding the Dsg2-directed CAR molecule, or fragment thereof, encodes 1, 2, 3, 4, 5, or all 6 of: a heavy chain (HC) CDR1 sequence of SEQ ID NO:18, a HC CDR2 sequence of SEQ ID NO:20, a HC CDR3 sequence of SEQ ID NO:22, a light chain (LC) CDR1 sequence of SEQ ID NO:26, a LC CDR2 sequence of SEQ ID NO:28, and a LC CDR3 sequence of SEQ ID NO:30. In one embodiment, the nucleic acid molecule encoding the Dsg2-directed CAR molecule, or fragment thereof, comprises 1, 2, 3, 4, 5, or all 6 of: a heavy chain (HC) CDR1 encoding sequence of SEQ ID NO:17, a HC CDR2 encoding sequence of SEQ ID NO:19, a HC CDR3 encoding sequence of SEQ ID NO:21, a light chain (LC) CDR1 encoding sequence of SEQ ID NO:25, a LC CDR2 encoding sequence of SEQ ID NO:27, and a LC CDR3 encoding sequence of SEQ ID NO:29.

As described above, a CAR also contains a signaling domain that functions in the immune cell expressing the CAR. Such a signaling domain can be, for example, derived from CD3ζ or Fc receptor γ (see Sadelain et al., Cancer Discov. 3:288-298 (2013). In general, the signaling domain will induce persistence, trafficking and/or effector functions in the transduced immune cells, or precursor cells thereof (Sharpe et al., Dis. Model Mech. 8:337-350 (2015); Finney et al., J. Immunol. 161:2791-2797 (1998); Krause et al., J. Exp. Med. 188:619-626 (1998)). In the case of CD3ζ or Fc receptor γ, the signaling domain corresponds to the intracellular domain of the respective polypeptides, or a fragment of the intracellular domain that is sufficient for signaling. Exemplary signaling domains are described below in more detail.

In one embodiment, the CAR molecule comprises a sequence as set forth in SEQ ID NO:34, or a fragment or variant thereof. In one embodiment, the CAR molecule comprises a sequence as set forth in SEQ ID NO:36, or a fragment or variant thereof.

In some embodiments, a variant of the CAR molecule as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over the full length of the amino acid sequence of SEQ ID NO:34 or SEQ ID NO:36.

In some embodiments, a fragment of the CAR molecule as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length amino acid sequence of SEQ ID NO:34 or SEQ ID NO:36.

In one embodiment, the nucleic acid molecule encoding the CAR molecule encodes a sequence as set forth in SEQ ID NO:34, or a fragment or variant thereof. In one embodiment, the nucleic acid molecule encoding the CAR molecule encodes a sequence as set forth in SEQ ID NO:36, or a fragment or variant thereof.

In one embodiment, the nucleic acid molecule encoding the CAR molecule comprises a nucleotide sequence as set forth in SEQ ID NO:33, or a fragment or variant thereof. In one embodiment, the nucleic acid molecule encoding the CAR molecule comprises a nucleotide sequence as set forth in SEQ ID NO:35, or a fragment or variant thereof.

In some embodiments, a variant of a nucleotide sequence encoding the CAR molecule as described herein comprises at least about 60% identity, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over the full length of a nucleotide sequence of SEQ ID NO:33 or SEQ ID NO:35.

In some embodiments, a fragment of a nucleotide sequence encoding the CAR molecule as described herein comprises at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the full length nucleotide sequence of SEQ ID NO:33 or SEQ ID NO:35.

CD3ζ

In a non-limiting embodiment, a CAR can comprise a signaling domain derived from a CD3ζ polypeptide, for example, a signaling domain derived from the intracellular domain of CD3ζ, which can activate or stimulate an immune cell. CD3ζ comprises 3 Immune-receptor-Tyrosine-based-Activation-Motifs (ITAMs), and transmits an activation signal to the cell, for example, a cell of the lymphoid lineage, such as a T cell, after antigen is bound. It is understood that a "CD3ζ nucleic acid molecule" refers to a polynucleotide encoding a CD3ζ polypeptide.

In certain non-limiting embodiments, an intracellular domain of a CAR can further comprise at least one co-stimulatory signaling domain. Such a co-stimulatory signaling domain can provide increased activation of an immune cell. A co-stimulatory signaling domain can be derived from a CD28 polypeptide, a 4-1BB polypeptide, an OX40 polypeptide, an ICOS polypeptide, a DAP10 polypeptide, a 2B4 polypeptide, and the like. In some embodiments, the intracellular domain of a CAR can comprise a co-stimulatory signaling region that comprises two co-stimulatory molecules, such as CD28 and 4-1BB, or CD28 and OX40, or other combinations of co-stimulatory ligands, as disclosed herein.

Signal Peptide

In some embodiments, the antigen binding domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, in some embodiments, a polypeptide such as a CAR is expressed at the cell surface as a mature protein lacking the signal peptide, whereas the precursor form of the polypeptide includes the signal peptide. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. Any suitable signal peptide, as are well known in the art, can be applied to a CAR to provide cell surface expression in an immune cell (see Gierasch Biochem. 28:923-930 (1989); von Heijne, J. Mol. Biol. 184 (1):99-105 (1985)). Exemplary signal peptides can be derived from cell surface proteins naturally expressed in an immune cell, including any of the signal peptides of the polypeptides disclosed herein. Thus, any suitable signal peptide can be utilized to direct a CAR to be expressed at the cell surface of an immune cell.

Linker

In certain non-limiting embodiments, an antigen-binding domain of a CAR can comprise a linker sequence or peptide linker connecting the heavy chain variable region and light chain variable region of the antigen-binding domain. In certain non-limiting embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the CH2CH3 (constant) region of an immunoglobulin, and/or portions of CD3 (cluster of differentiation 3) or some other sequence suitable as a spacer.

In some embodiments, the transmembrane domain of a CAR comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the immune cell. In one embodiment, a CAR can have a transmembrane domain derived from CD8, CD28, CD3, CD4, 4-1BB, OX40, ICOS, CTLA-4, PD-1, LAG-3, 2B4, BTLA, or other polypeptides expressed in the immune cell having a transmembrane domain, including others as disclosed herein or that are well known in the art. Optionally, the transmembrane domain can be derived from a polypeptide that is not naturally expressed in the immune cell, so long as the transmembrane domain can function in transducing signal from antigen bound to the CAR to the intracellular signaling and/or co-stimulatory domains. It is understood that the portion of the polypeptide that comprises a transmembrane domain of the polypeptide can include additional sequences from the polypeptide, for example, additional sequences adjacent on the N-terminal or C-terminal end of the transmembrane domain, or other regions of the polypeptide, as desired.

It is understood that domains of the polypeptides described herein can be used in a cancer antigen CAR, as useful to provide a desired function such as a signal peptide, antigen binding domain, transmembrane domain, intracellular signaling domain and/or co-stimulatory domain. For example, a domain can be selected such as a signal peptide, a transmembrane domain, an intracellular signaling domain, or other domain, as desired, to provide a particular function to a CAR of the invention. Possible desirable functions can include, but are not limited to, providing a signal peptide and/or transmembrane domain.

Chimeric Co-Stimulatory Receptors (CCRs)

In some embodiments, the invention provides a chimeric co-stimulatory receptor (CCR). Chimeric co-stimulatory receptors (CCRs) are chimeric receptors that, similar to a CAR, comprise an antigen-binding extracellular domain, a transmembrane domain and an intracellular signaling domain (Sadelain et al., Cancer Discov. 3(4):388-398 (2013)). CCRs do not have a T cell activation domain, but do comprise a co-stimulatory domain, such as one of the co-stimulatory domains described above for a CAR, for example, CD28, 4-1BB, OX40, ICOS, DAP10, 2B4, CD70, or the like. CCRs can be used in conjunction with a T cell receptor or a CAR to enhance T cell reactivity against dual-antigen expressing T cells (Sadelain et al., supra, 2013). CCRs can also be used to enhance selective tumor targeting (Sadelain et al., supra, 2013). A CCR is an antigen-specific co-stimulatory receptor, which mimics the effects 4-1BB, OX40, ICOS or CD70 (depending on the co-stimulatory domain of the CCR) upon binding to its binding partner, i.e., a target antigen.

Dominant Negative iCAR

In one embodiment, the Dsg2 binding molecule of the invention comprises a dominant negative molecule which stimulates or sustains activation of a T cell of the invention. Exemplary dominant negative molecules include, but are not limited to, an inhibitory chimeric antigen receptor (iCAR), a secretable soluble cytokine receptor (e.g., for TGFBeta, IL10), a secretable soluble T-cell inhibitory receptor (e.g., derived from PD1, CTLA4, LAG3, or TIM-3), and the like. In some embodiments iCARs are cell-surface receptors composed of a Dsg2 binding molecule (e.g., Dsg2-scFv) fused to an intracellular signaling domain derived from inhibitory T-cell receptors (such as PD1, CTL4). Engineered T cells are inhibited upon interaction with a target cell.

Genetic Circuits

In one embodiment, the Dsg2 binding molecule, CAR or CCR of the invention is integrated into a genetic circuit. A genetic circuit is a set of gene expression units that are functionally connected.

In one embodiment a genetic circuit comprises constitutive transcription unit that expresses a cell-surface ligand-specific synthetic transcription factor (TF) where upon ligand binding the TF moiety is released and translocates to the nucleus. Then, the TF binds its cognate DNA sequence in the nucleus, which activates gene expression. In one embodiment, the cell-surface ligand-specific synthetic transcription factor (TF) is specific for binding to Dsg2.

Examples of genetic circuits which can incorporate a Dsg2 binding molecule, CAR or CCR of the invention include, but are not limited to, SynNotch circuits, NFAT circuits, and HIFlalpha circuits.

In another embodiment, the Dsg2 binding molecule, CAR or CCR of the invention is integrated into a logic-gated system. Logic-gated CAR systems that can comprise a Dsg2 binding molecule, CAR or CCR of the invention are described in International patent application publication WO2015075469A1, which is incorporated herein by reference in its entirety.

Fusion Molecules

In one embodiment, the Dsg2 binding molecule is conjugated to other proteins, nucleic acid molecules, or small molecules, to prepare fusion molecules. This may be accomplished, for example, by the synthesis of N-terminal or C-terminal fusion proteins provided that the resulting fusion protein retains the functionality of binding to Dsg2 as described herein. N-terminal or C-terminal fusion proteins comprising a peptide or protein of the invention, conjugated with at least one other molecule, may be prepared by fusing, through recombinant techniques, the N-terminal or C-terminal end of the peptide or protein, and the sequence of a selected protein or selectable marker with a desired biological function. The resultant fusion proteins contain the peptide of the invention fused to the selected protein or marker protein as described herein.

The present invention further encompasses fusion proteins in which the protein of the invention or fragments thereof, are recombinantly fused or chemically conjugated (including both covalent and non-covalent conjugations) to heterologous proteins (i.e., an unrelated protein or portion thereof, e.g., at least 10, at least 20, at least 30, at least 40, at least 50, at least 60, at least 70, at least 80, at least 90 or at least 100 amino acids of the polypeptide) to generate fusion proteins. The fusion does not necessarily need to be direct but may occur through linker sequences.

Therefore, in some embodiments the invention includes fusion molecules comprising a Dsg2 binding molecule of the invention fused to one or more therapeutic molecule. In one embodiment, the fusion molecule of the invention is an antibody-drug conjugate comprising a Dsg2 binding molecule of the invention. In one embodiment, the therapeutic molecule comprises an agent for the treatment of cancer.

Methods of Use

In some embodiments, the Dsg2 binding molecules (e.g., antibodies, etc.) of the present invention, exhibit a high capacity to detect and bind Dsg2 in a complex mixture of salts, compounds and other polypeptides. The skilled artisan will understand that the Dsg2 binding molecules (e.g., antibodies, etc.) described herein are useful in procedures and methods that include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an Ouchterlony immunodiffusion assay, reverse phase protein microarray, a rocket immunoelectrophoresis assay, an immunohistostaining assay, an immunoprecipitation assay, a complement fixation assay, FACS, a protein chip assay, separation and purification processes, and affinity chromatography (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In some embodiments, the invention relates to methods of administering a Dsg2 binding molecule of the invention, or a nucleic acid molecule encoding a Dsg2 binding molecule of the invention to a subject. In one embodiment the Dsg2 binding molecule of the invention is administered to a subject to diagnose or treat cancer.

The following are non-limiting examples of cancers that can be diagnosed or treated by the disclosed methods and compositions: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, Burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytoma/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, Ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, Hodgkin's lymphoma, hypopharyngeal cancer, hypothalamic and visual pathway glioma, hypothalamic tumor, intraocular (eye) cancer, intraocular melanoma, islet cell tumors, Kaposi sarcoma, kidney (renal cell) cancer, Langerhans cell cancer, Langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, Merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-Hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, Sézary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, Waldenstrom macroglobulinemia, and Wilms tumor.

The invention also relates to methods of treating a subject with immunotherapy, wherein the subject is in need of such therapy. In some embodiments the immunotherapy promotes an immune response. In some embodiments, the subject being treated may have cancer or pre-cancer, and administration of the recombinant immune cells of the invention is to treat the cancer or prevent progression of the cancer. The immune cells may be targeted to the cancer by virtue of recombinantly expressing a Dsg2 binding molecule (e.g., a CAR or antibody). In some embodiments the CAR binds to Dsg2 expressed on a tumor cell and administration of the recombinant immune cells of the invention treats the cancer. In one embodiment, the recombinant immune cell is a T cell. The T cell can be CD8+, CD4+, a TSCM, a TCM, effector memory T cell, effector T cell, Th1 cell, Th2 cell, Th9 cell, Th17 cell, Th22 cell, Tfh (follicular helper) cell, or other T cell as disclosed herein.

It is understood that a method of treating cancer can include any effect that ameliorates a sign or symptom associated with cancer. Such signs or symptoms include, but are not limited to, reducing the number of cancer cells, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers. Thus, administration of the cells of the invention can reduce the number of tumor cells, reduce tumor size, and/or eradicate the tumor in the subject. The tumor can be a blood cancer or a solid tumor. The methods of the invention can also provide for increased or lengthened survival of a subject having cancer. Additionally, methods of the invention can provide for an increased immune response in the subject, for example, an increased immune response against the cancer.

In some embodiments, a pharmaceutical composition comprising a cell of the invention is administered to a subject to elicit an immune response. In one embodiment, the cells of the invention are administered to a subject, such as a human subject, to induce an immune response against Dsg2.

In some embodiments, the cancer can involve a solid tumor. Cancers to be treated using the cells of the invention comprise cancers typically responsive to immunotherapy. Exemplary types of cancers include, but are not limited to, adrenocortical carcinoma (ACC); bladder urothelial carcinoma (BLCA); breast invasive carcinoma (BRCA); cervical squamous cell carcinoma and endocervical adenocarcinoma (CESC); cholangiocarcinoma (CHOL); colon adenocarcinoma (COAD); lymphoid neoplasm diffuse large B-cell lymphoma (DLBC); esophageal carcinoma (ESCA); glioblastoma multiforme (GBM); head and neck squamous cell carcinoma (HNSC); kidney chromophobe (KICH); kidney renal clear cell carcinoma (KIRC); kidney renal papillary cell carcinoma (KIRP); acute myeloid leukemia (LAML); brain lower grade glioma (LGG); liver hepatocellular carcinoma (LIHC); lung adenocarcinoma (LUAD); lung squamous cell carcinoma (LUSC); mesothelioma (MESO); multiple myeloma (MM); ovarian serous cystadenocarcinoma (OV); pancreatic adenocarcinoma (PAAD); pheochromocytoma and paraganglioma (PCPG); prostate adenocarcinoma (PRAD); rectum adenocarcinoma (READ); sarcoma (SARC); skin cutaneous melanoma (SKCM); stomach adenocarcinoma (STAD); testicular germ cell tumors (TGCT); thyroid carcinoma (THCA); thymoma (THYM); uterine corpus endometrial carcinoma (UCEC); uterine carcinosarcoma (UCS); and uveal Melanoma (UVM).

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically taken into account when determining an appropriate dosage to achieve an effective amount. These factors include age, sex and weight of the subject, the condition being treated, the severity of the condition and the form and effective concentration of the cells of the invention being administered.

The cells of the invention are generally administered as a dose based on cells per kilogram (cells/kg) of body weight. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$, depending on the mode and location of administration. In general, in the case of systemic administration, a higher dose is used than in regional administration, where the immune cells of the invention are administered in the region, an organ or a tumor. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$ to $1\times10^8$, $7\times10^4$ to $1\times10^8$, $8\times10^4$ to $1\times10^8$, $9\times10^4$ to $1\times10^8$, $1\times10^5$ to $1\times10^8$, and the like. Such dose ranges can be particularly useful for regional administration. In a particular embodiment, cells are provided in a dose of $1\times10^5$ to $5\times10^6$, in particular $1\times10^5$ to $3\times10^6$ or $3\times10^5$ to $3\times10^6$ cells/kg for regional administration, for example, intrapleural administration. The dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

The cells of the invention can be administered by any methods known in the art, including, but not limited to, pleural administration, intravenous administration, subcutaneous administration, intranodal administration, intratumoral administration, intrathecal administration, intrapleural administration, intraperitoneal administration, intracranial administration, and direct administration to the thymus. In one embodiment, the cells of the invention can be delivered regionally to an organ, a tumor or site of an autoimmune disease or site of an infectious disease using well known methods, including but not limited to, hepatic or aortic pump; limb, lung or liver perfusion; in the portal vein; through a venous shunt; in a cavity or in a vein that is nearby a tumor, and the like. In another embodiment, the cells of the invention can be administered systemically. In still another embodiment, the cells are administered regionally at the site of a desired therapy, for example, at the site of a tumor. In the case of a tumor, the cells can also be administered intratumorally, for example, by direct injection of the cells at the site of a tumor and/or into the tumor vasculature. One skilled in the art can select a suitable mode of administration based on the type of target tissue or target region and/or location of a target tissue or target region to be treated. The cells can be introduced by injection or catheter. Optionally, expansion and/or differentiation agents can be administered to the subject prior to, during or after administration of cells to increase production of the cells of the invention in vivo.

In some embodiments, proliferation of the cells of the invention is done ex vivo, prior to administration to a subject, or in vivo after administration to a subject (see Kaiser et al., Cancer Gene Therapy 22:72-78 (2015)).

The methods of the invention can further comprise adjuvant therapy in combination with, either prior to, during, or after treatment with the cells of the invention. Thus, the cell therapy methods of the invention can be used with other standard care and/or therapies that are compatible with administration of the cells of the invention.

Pharmaceutical Compositions

In some embodiments, the invention provides pharmaceutical compositions comprising the Dsg2 binding molecule, CAR or cells of the invention. In one embodiment, the pharmaceutical composition comprises an effective amount of a Dsg2 binding molecule, CAR or cells of the invention and a pharmaceutically acceptable carrier. The pharmaceutical compositions of the invention can be conveniently provided in sterile liquid preparations, for example, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating a composition of the invention in a suitable amount of the appropriate solvent with various amounts of the other ingredients, as desired. Such compositions can include a pharmaceutically acceptable carrier, diluent, or excipient such as sterile water, physiological saline, glucose, dextrose, or the like, that are suitable for use with a cell composition and for administration to a subject such as a human. Suitable buffers for providing a cell composition are well known in the art. Any vehicle, diluent, or additive used is compatible with preserving the integrity and viability of the cells of the invention.

In some embodiments, the compositions are isotonic, that is, they have the same osmotic pressure as blood. The desired isotonicity of the cell compositions of the invention can be accomplished using sodium chloride, or other pharmaceutically acceptable agents such as dextrose, boric acid, sodium tartrate, or other inorganic or organic solutes. Sodium chloride is preferred particularly for buffers containing sodium ions. One particularly useful buffer is saline, for example, normal saline. Those skilled in the art will recognize that the components of the compositions should be selected to be chemically inert and will not affect the viability or efficacy of the cells of the invention and will be compatible for administration to a subject, such as a human. The skilled artisan can readily determine the amount of cells and optional additives, vehicles, and/or carrier in compositions to be administered in methods of the invention.

The compositions of the invention can be administered in any physiologically acceptable vehicle. Suitable doses for administration are described herein.

A cell population comprising cells of the invention can comprise a purified population of cells. Those skilled in the art can readily determine the percentage of cells in a cell population using various well-known methods, as described herein. The ranges of purity in cell populations comprising genetically modified cells of the invention can be from about 25% to about 50%, from about 30% to about 50%, from about 30% to about 40%, from about 40% to 50%, from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. It is understood that such a population can be generated efficiently with the methods of the invention, as disclosed herein, or optionally enriched for the genetically modified cells expressing a Dsg2 binding molecule, as disclosed herein. In one embodiment the Dsg2 binding molecule comprises a CAR.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In one embodiment, such powders comprise particles wherein at least 98% of the particles by weight have a diameter greater than 0.5 nanometers and at least 95% of the particles by number have a diameter less than 7 nanometers. In one embodiment, at least 95% of the particles by weight have a diameter greater than 1 nanometer and at least 90% of the particles by number have a diameter less than 6 nanometers. In some instances, dry powder compositions include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some instances having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In one embodiment, the droplets provided by this route of administration have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. In one embodiment, such powdered, aerosolized, or aerosolized formulations, when dispersed, have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, PA), which is incorporated herein by reference.

Kits

The invention also provides kits comprising a composition of the invention. In one embodiment, the kit comprises in one or more containers: one or more vectors for generating a genetically engineered immune cell of the invention. In one embodiment, the vector comprises a CAR. In one embodiment, the kits can be used to generate genetically engineered immune cells from autologous cells derived from a subject or from non-autologous cells to be administered to a compatible subject. In another embodiment, the kits can comprise cells of the invention for autologous or non-autologous administration to a subject. In specific embodiments, the kit comprises the immune cells of the invention in one or more containers.

Cancer Therapy

The compositions of the invention can be used to prevent, abate, minimize, control, and/or lessen cancer in humans and animals. The compositions of the invention can also be used to slow the rate of primary tumor growth. The compositions of the invention when administered to a subject in need of treatment can be used to stop the spread of cancer cells. As such, an effective amount of a Dsg2 binding molecule of the invention, a nucleic acid molecule encoding Dsg2 binding molecule of the invention of the invention, or a cell modified to express a Dsg2 binding molecule of the invention can be administered as part of a combination therapy with one or more drugs or other pharmaceutical agents. When used as part of the combination therapy, the decrease in metastasis and reduction in primary tumor growth afforded by the compositions of the invention allows for a more effective and efficient use of any pharmaceutical or drug therapy being used to treat the patient. In addition, control of metastasis by the compositions of the invention affords the subject a greater ability to concentrate the disease in one location.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Therefore, in one embodiment, the composition of the invention comprises a combination of a Dsg2 binding molecule of the invention, a nucleic acid molecule encoding Dsg2 binding molecule of the invention of the invention, or a cell modified to express a Dsg2 binding molecule of the invention and one or more additional therapeutic agent. In some embodiments, the therapeutic agent comprises a peptide, nucleic acid molecule, small molecule, antibody, or the like. In some embodiments, the additional therapeutic agent is for the treatment cancer.

In one embodiment, the therapeutic agent comprises a checkpoint inhibitor. In some embodiments, the combination of antigen and immune checkpoint antibody induces the immune system more efficiently than an immunogenic composition comprising the antigen alone. This more efficient immune response provides increased efficacy in the treatment and/or prevention of cancer. In one embodiment, the checkpoint inhibitor inhibits at least one of PD-1, PDL-1 CTLA-4, LAG-3, TIM-3, TIGIT and CEACAM1. Exemplary checkpoint inhibitors that can be used in the compositions and methods of the invention include, but are not limited to, ipilimumab, nivolumab, pembrolizumab, pidilizumab, atezolizumab, BMS-986016, BMS-936559, MPDL3280A, MDX1105-01, MEDI4736, TSR-022, CM-24 and MK-3475.

In one embodiment, the additional therapeutic agent comprises a therapeutic antibody or antibody fragment. The therapeutic antibody or antibody fragment includes any antibody known in the art which binds to a tumor cell, induces the killing of the tumor cell, or prevents tumor cell proliferation or metastasis. In one embodiment, the therapeutic agent comprises an antibody-drug conjugate.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compounds of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples are not to be construed as limiting in any way the remainder of the disclosure.

Example 1: Dsg2-Directed CAR-T Cell Therapy for Solid Cancers

The desmosomal cadherin, desmoglein 2 (Dsg2) is an important regulator of signaling pathways involved in cell proliferation and migration in various cell populations (Kant et al. 2015; Eshkind et al., 2002, Eur J Cell Biol. 81: 592-598). Also, Dsg2 is upregulated in nearly all solid cancers and expression correlates with poor prognosis (Kamekura et al., 2013, Oncogene. 33(36): 4531-4536; Brennan, Hu et al., 2007, J Cell Sci. 120(5): 758-771; Brennan-Crispi et al., 2015, Oncotarget. 6(11): 6(11):8593-8605; Brennan-Crispi et al., 2019, J Invest Dermatol. 139(2):

300-307; Tan et al. 2016, Oncotarget. 7(29): 46492-46508), making it a novel candidate for targeted therapy. The expression of Dsg2 in many tissues and its vital role in various tissues suggest that it would not be a viable immunotherapy target reflecting the high risk of autoimmune toxicity. However, without being bound by theory, it was hypothesized that, in the context of Dsg2 overexpression and dysregulation by cancers and sequestration of Dsg2 in desmosomes in normal cells, a "window of opportunity" exists for specific cancer cell elimination with Dsg2-targeted CAR-T or CAR-NK cell therapy without collateral toxicity in normal tissues. Indeed, the data presented herein suggest that nearly all solid cancer types can be targeted and eliminated by Dsg2 CAR-T cells with no toxicity in mouse models, demonstrating that Dsg2-targeted CAR-T/CAR-NK cell therapy is a potentially universal, "off-the-shelf" cellular therapy for cancer.

This work has focused on the cadherin desmoglein 2 (Dsg2), an important regulator of signaling pathways involved in cell proliferation and migration in various stem cell populations. Dsg2 is upregulated in 10 of the 13 most common cancers and its expression correlates with poor prognosis, making Dsg2 a novel candidate for targeted therapy in a spectrum of human cancers.

It has been demonstrated that human SCC xenografts can be targeted by Dsg2-specific monoclonal antibody treatment. This work demonstrates that aberrant cell surface presentation of Dsg2 provides an opportunistic therapeutic target for CAR-T cell immunotherapy. Dsg2-specific hybridomas are used to obtain huma Dsg2-specific antibody sequences and generate huma Dsg2-specific CARs and CAR-T cells. The work presented herein demonstrates their effectiveness in killing cSCC and HNSCC cells in vitro and abolishing patients' tumor xenografts in vivo.

Desmosomes are adhesive junctions abundantly expressed in tissues that experience mechanical stress such as the skin and heart (Kowalczyk and Green, 2013, Prog Mol Biol Transl Sci. 116: 95-118). They provide tensile strength by linking the transmembrane adhesive components to the intermediate cytoskeletal keratin filaments. The extracellular domains of the cadherins (desmogleins and desmocollins) mediate cell-cell adhesion while the intracellular cytoplasmic domains bind the armadillo (plakoglobin and plakophilin) signaling proteins and recruit the plakin (desmoplakin and periplakin) family of linker proteins. In humans, disruption of desmosomal function underlies several autoimmune, infectious, and heritable disorders affecting diverse tissues including the skin, nail, hair, and heart (Najor, 2018, Annu Rev Pathol. 13: 51-70). There are 4 distinct desmoglein genes (Dsg 1-4) and while Dsg1, 3 and 4 are restricted mainly to stratified epithelia, such as the skin and oral mucosa, Dsg2 is also found in simple epithelia and the heart. Mutations in the huma Dsg2 gene underlie some arrythmogenic right ventricular cardiomyopathies that often result in sudden death (Lombardi and Marian, 2010, Curr Opin Cardiol. 25: 222-228). Dsg2 also serves as a receptor for adenoviruses that are involved in respiratory and urinary tract infections and is associated with Alzheimer's disease (Wang, Li et al. 2011, Nat Med. 17(1): 96-104). Interestingly, in human pluripotent stem cells Dsg2 has been shown to be critical for self-renewal, embryonic body and teratoma formation, and mediates the epithelial-to-mesenchymal transition through a β-catenin/Slug pathway (Park, Son et al., 2018, Stem Cell Reports. 11(1): 115-127). In mice, ablation of the Dsg2 gene results in loss of the trophectoderm layer in the blastocysts and embryonic lethality and $Dsg2^{-/-}$ embryonic stem cells are not viable in culture suggesting that Dsg2 plays a critical role in cell growth and survival (Eshkind, Tian et al., 2002, Eur J Cell Biol. 81: 592-598.)

Dsg2 is highly expressed in malignant epithelial cell lines and in the two most common skin cancers, basal cell carcinomas (BCCs) and SCCs (Biedermann, Vogelsang et al., 2005, J Pathol. 207(2): 199-206; Brennan and Mahoney, 2009, Cell Adh Migr. 3(2): 148-154). Furthermore, Dsg2 promotes vasculogenic mimicry to increase tumor blood supply and is associated with poor prognosis in malignant melanoma (Tan, Mintoff et al., 2016, Oncotarget. 7(29): 46492-46508). Overexpression of Dsg2 also occurs in prostate and colon cancers, suggesting a role for Dsg2 in oncogenesis in a variety of epithelial-derived tissues (Barber, Castillo-Martin et al., 2014, PLoS One. 9(6): e98786). Knockdown of Dsg2 in colonic epithelial carcinoma cells decreases proliferation and suppresses xenograft tumor growth in mice (Kamekura, Kolegraff et al., 2013, Oncogene. 33(36): 4531-4536). Furthermore, forced expression of Dsg2 in the epidermis of transgenic mice promotes epidermal hyperplasia and increases susceptibility to tumor development (Brennan, Hu et al., 2007, J Cell Sci. 120(5): 758-771; Brennan, Peltonen et al., 2012, Oncogene. 31(13): 1636-1648; Overmiller, McGuinn et al., 2016, Oncotarget, 7(25): 37536-37555). Through Stat3, Dsg2 upregulates Glil and Ptchl, target genes of the Hh signaling pathway, and compound $Dsg2/Ptcl^{+/lacZ}$ mice have accelerated development of BCCs and SCCs and tumorigenesis in response to chemical carcinogens (Brennan-Crispi et al. 2015, Oncotarget. 6(11): 6(11):8593-8605; Brennan-Crispi et al., 2019, J Invest Dermatol. 139(2): 300-307).

Figure 1:
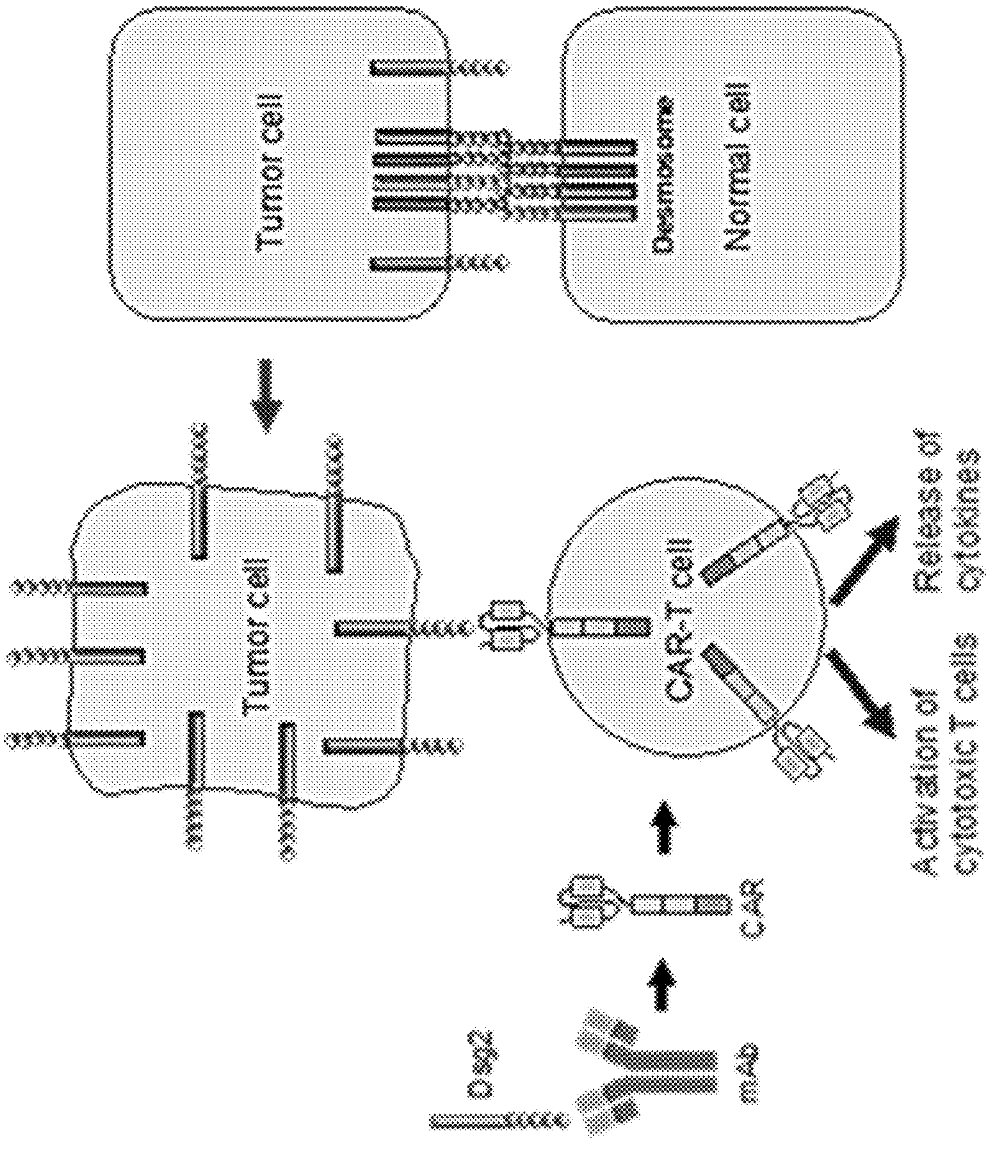
FIG. 1 is a schematic diagram of strategy and rationale for using Dsg2-specific CAR-T cells in adoptive T cell immunotherapy. T cells are engineered to express chimeras of Dsg2-binding and T-cell activating domains (CARs). In normal cells, Dsg2 is localized to the desmosomal complex and is not accessible to CAR-T cells. Tumor cells express high levels of desmosome-free Dsg2, targetable by CAR-T cells.

It was examined whether Dsg2 overexpression by SCCs and the sequestration of Dsg2 in desmosomes in normal cells may create a "window of opportunity" for specific elimination of SCCs by Dsg2-specific CAR-T cell therapy without collateral toxicity in normal tissues (FIG. 1).

Dsg2 is Upregulated in HNSCCs.

Figures 2A, 2B, 2C:
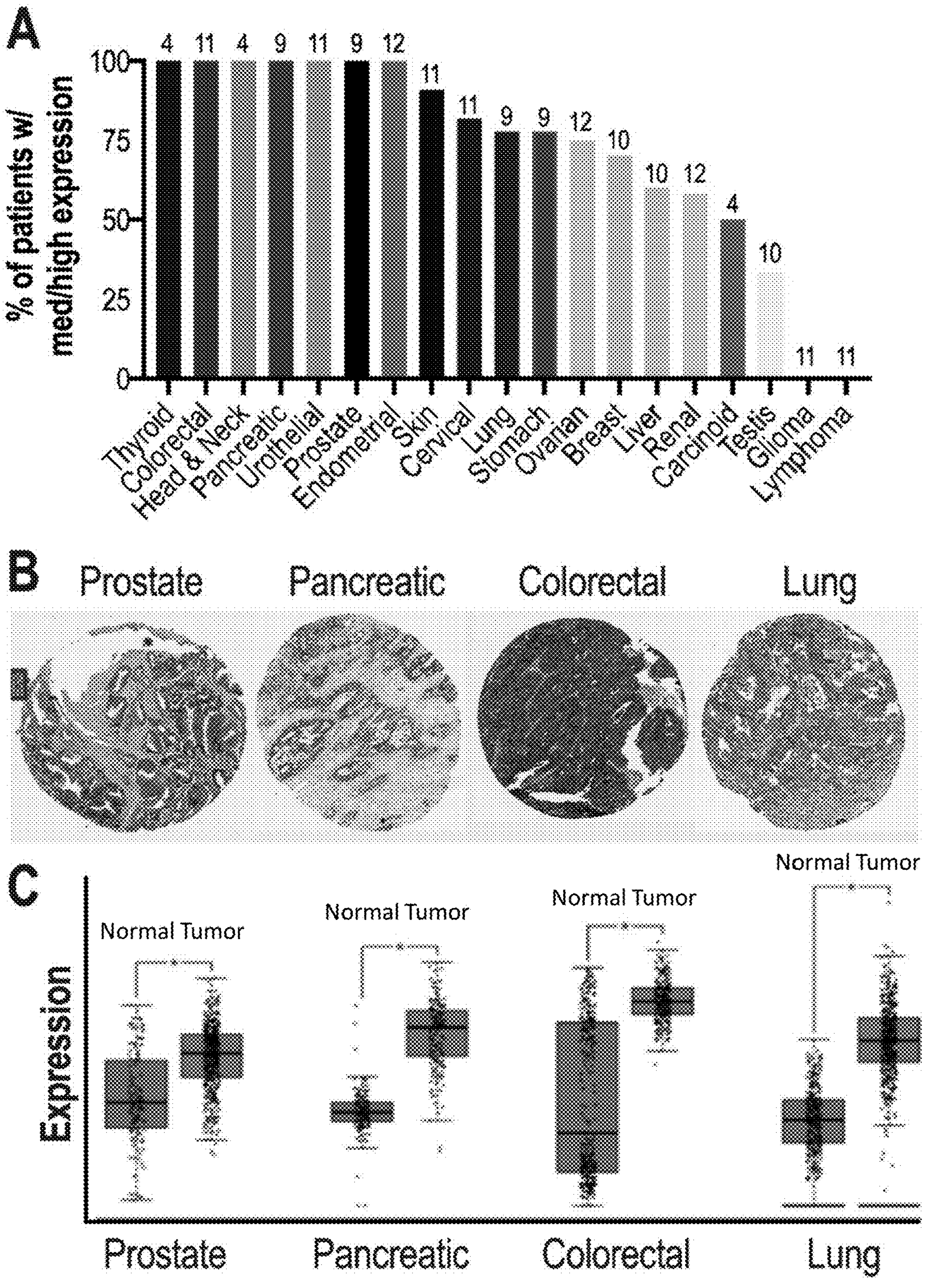
FIG. 2A through FIG. 2E depict exemplary experimental results demonstrating that Dsg2 is overexpressed in most solid cancers and correlates with poor prognosis.
Figure 2D:
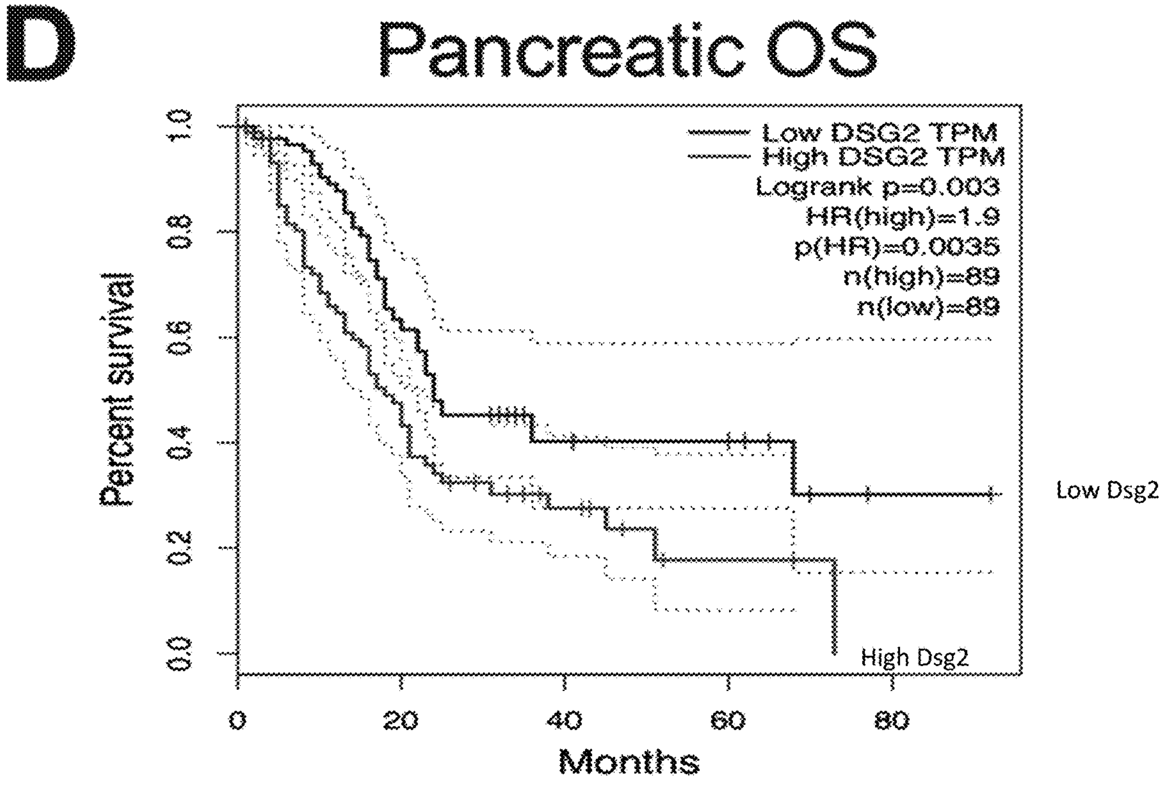
Figure 2E:
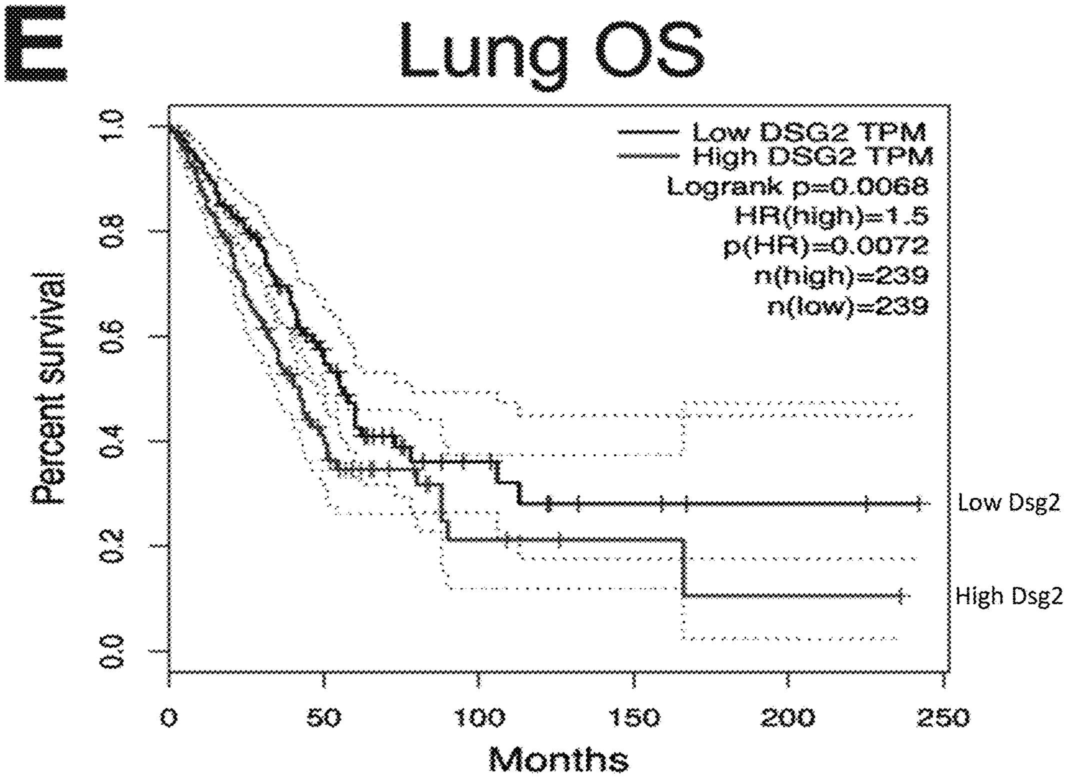

Dsg2 was not detected in any of the normal oral mucosa (n=12), while 15 of the 16 HNSCCs were positive for Dsg2 (FIG. 2A). This is similar to previous results obtained using cSCC tissue arrays (Wahl 2002, Hybrid Hybridomics. 21(1): 37-44; Biedermann, Vogelsang et al., 2005, J Pathol. 207(2): 199-206; Brennan and Mahoney, 2009, Cell Adh Migr. 3(2): 148-154). In silico analysis correlates Dsg2 expression with poor overall survival probability in HNSCCs (proteinatlas.org) (FIG. 2B). These findings suggest Dsg2 could serve as an excellent target for therapy in high-risk cSCCs and HNSCCs and this method could be applied to other high Dsg2 expressing cancers including lung, prostate and colon.

Dsg2 in Tumor Growth

Figures 3A, 3B, 3C:
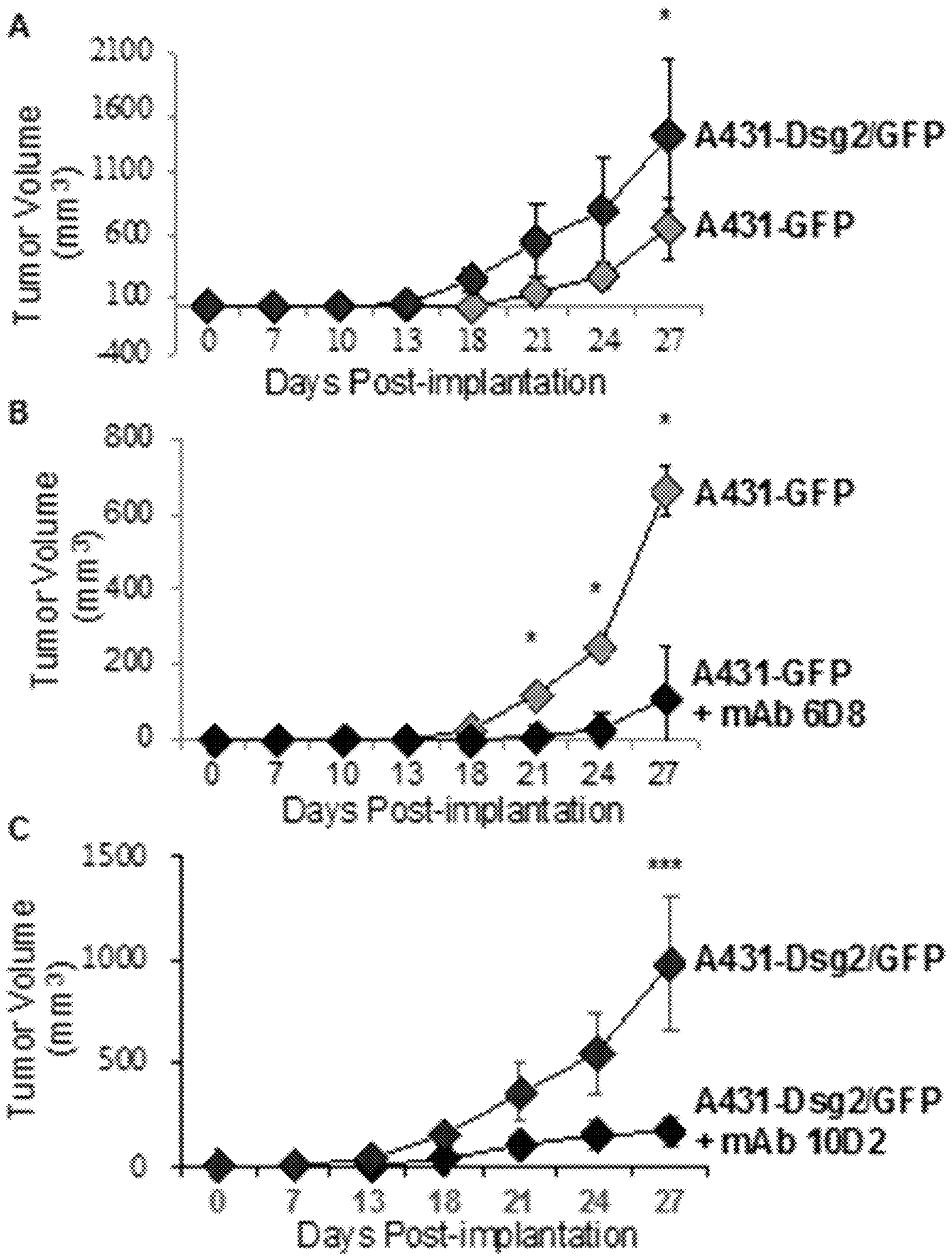
FIG. 3A through FIG. 3C depict exemplary experimental results demonstrating that Dsg2 mAB blocks tumor development.

To further assess the role of Dsg2 in tumor growth, A431 cSCC cells stably expressing exogenous GFP or Dsg2/GFP were generated using the retroviral expression vector LZRS-ms-neo (Brennan, Hu et al., 2007, J Cell Sci. 120(5): 758-771; Brennan, Peltonen et al., 2012, Oncogene. 31(13): 1636-1648; Overmiller, McGuinn et al. 2016, Oncotarget. 7(25): 37536-37555). Cells ($1\times10^6$) were implanted into immunocompromised SCID mice, and tumor volume was measured up to 27 days post-implantation. cSCC-GFP tumors reached an average volume of 662 $mm^3$ while the cSCC-Dsg2/GFP line achieved a significantly larger volume of 1428 $mm^3$ at the experiment's conclusion (FIG. 3A). These results demonstrate that Dsg2 is pro-tumorigenic in a xenograft model of malignancy. To further assess Dsg2 in SCC tumor xenograft growth and progression, the mAb 6D8 was used, which targets an epitope on the fourth extracellular domain of Dsg2 and promotes Dsg2 internalization (Biedermann, Vogelsang et al., 2005, J Pathol. 207(2):

199-206; Brennan and Mahoney, 2009, Cell Adh Migr. 3(2): 148-154). Purified mAb 6D8 was delivered intraperitoneally twice weekly (5 mg/kg) for 20 days. Tumors derived from treated mice were significantly smaller (133 $mm^3$) than the untreated mice (756 $mm^3$) (FIG. 3B). Similar results were found with mAb 10D2 (FIG. 3C). Analyzing the number of Ki67+ cancer cells, mAb 6D8-treated xenografts had significantly fewer cells that were actively dividing in the healthy layers of the xenograft. The mAb 6D8-treated tumors also expressed significantly less Dsg2, EGFR, and c-Src than PBS-treated tumors.

Dsg2 as a Therapeutic Means to Inhibit SCC Tumor Development

Figure 4:
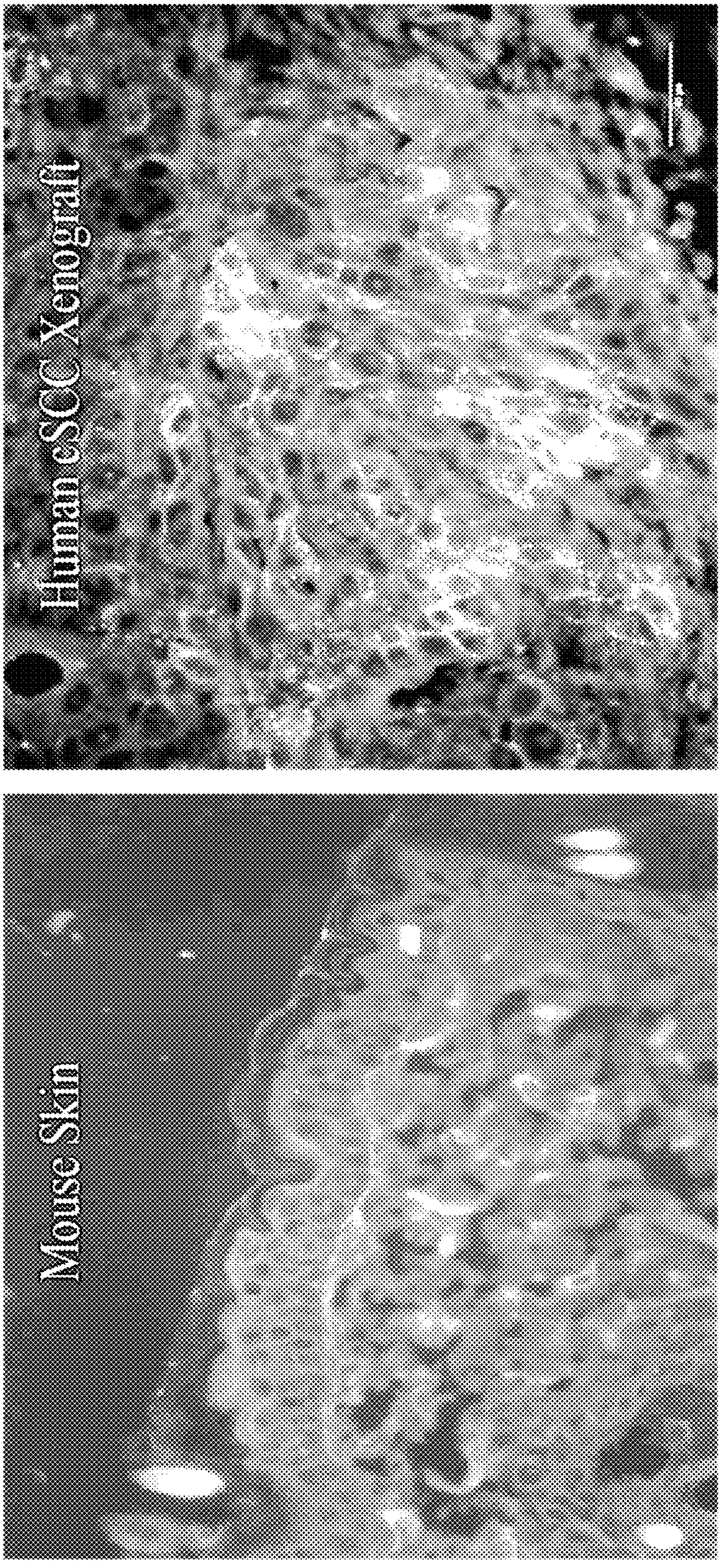
FIG. 4 depicts representative images depicting that tumor xenografts from primary human SCC cells express Dsg2. SCID Balb/c mice were injected subcutaneously in the flank with 1-4×$10^6$ primary human SCC tumor cells. Xenograft tumors were excised and immunostained for Dsg2 in the mouse epidermis (left) and tumor mass (right). Little to no expression of Dsg2 was detected in the skin.
Figures 5A, 5B, 5C:
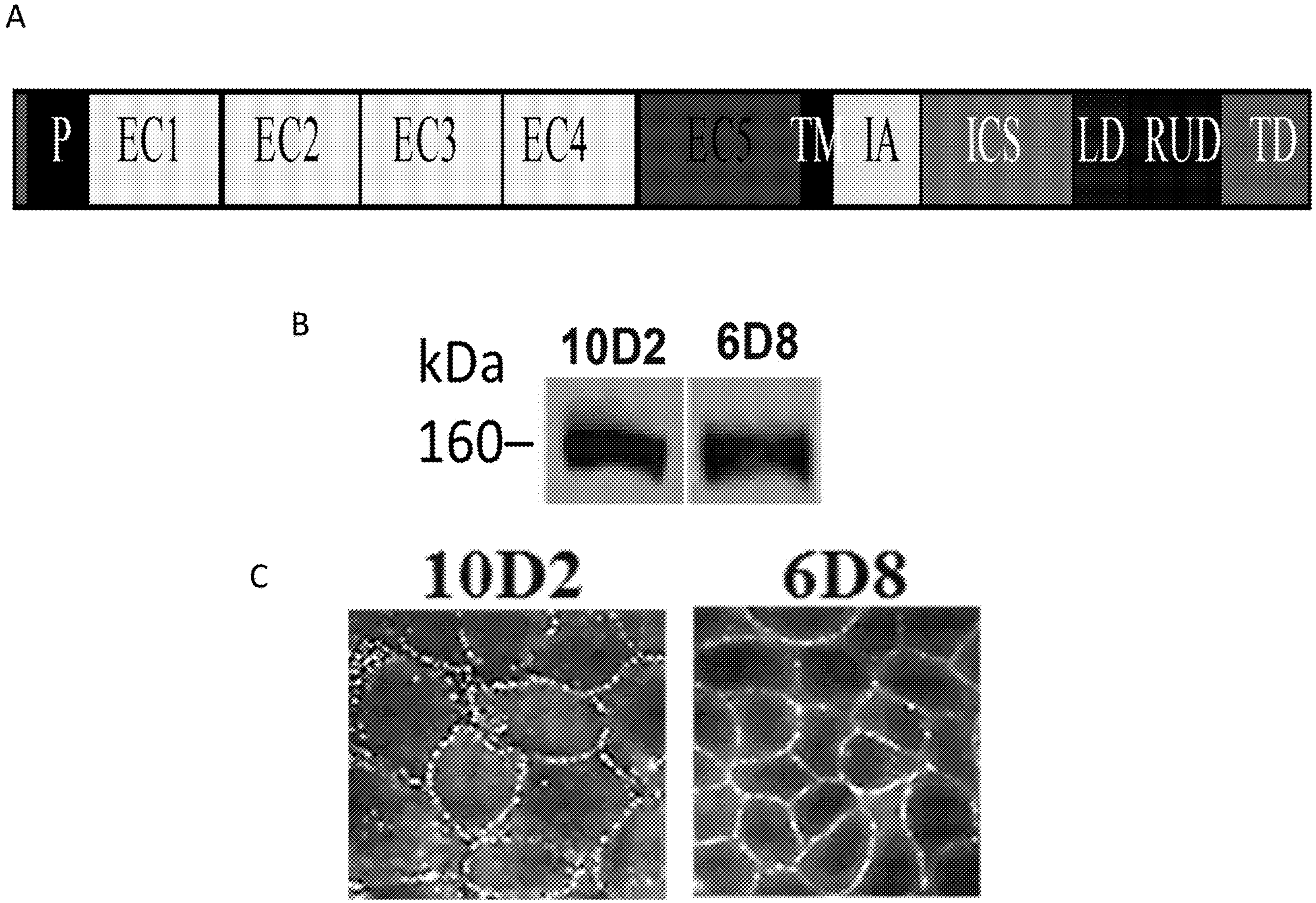
FIG. 5A through FIG. 5C depict results from exemplary experiments demonstrating Dsg2-specific monoclonal antibodies (mAbs.)
Figure 6:
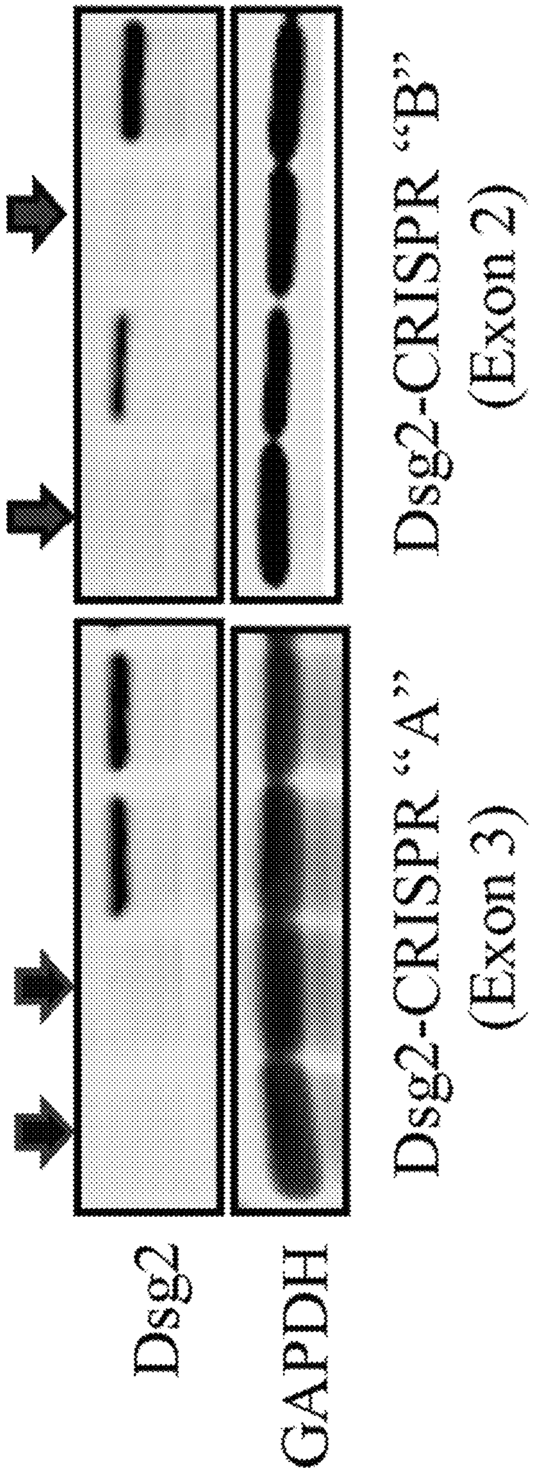
FIG. 6 depicts results from exemplary experiments demonstrating individual clones of four CRISPR/Cas9 constructs to knockout Dsg2 (n=20).

Xenografts were generated using primary human cSCC cells. Immunostaining of the tumors showed high levels of Dsg2 (FIG. 4). Targeted mAb therapies generally induce cancer cell death, impede angiogenesis into the growing tumor, and inhibit growth of the cancer cells. As a major concern of a Dsg2-directed mAb would be off-target effects in various Dsg2-expressing organs, mAb binding and histopathology of various tissues was assessed in a cohort of mice treated long-term with mAbs 6D8 and 10D2 alone at 5 mg/kg (~100 μg) every other day for up to 4 weeks (Sewell, Chapman et al. 2017, MAbs. 9: 742-755). These mice, like PBS-treated controls, had normal tissue histology of the colon, heart, skin, and oral mucosa following extended mAb treatment, and direct application of anti-mouse secondary Ab did not detect bound mAb 6D8 or 10D2 in these tissues. None of the mAb-treated mice were lost to treatment, nor did they have any observable treatment-related side effects. This suggests that Dsg2 is sequestered within desmosomal complexes in normal cells, preventing binding by Dsg2 mAbs and off-target toxicity. These results demonstrate the efficacy and tolerability of anti-Dsg2 therapies for SCC treatment, including Dsg2 mAbs and immunotherapies such as Dsg2-directed CAR-T cells.

Characterizing mAb Specific for Huma Dsg2

Data in FIG. 3B shows that mAb 6D8 was extremely effective at reducing xenograft tumor growth using cSCC A431. Experiments are designed to demonstrate the effectiveness of mAb 6D8 on abrogating UM-SCC1 xenograft tumors particularly in the NOD.Cg-Rag1tm1MomIl2rgtm1Wj1/SzJ (NRG) mice, which permit xenograft and CAR-T cell transfer. Briefly, a week after inoculation, tumors reach ~40 $mm^3$, at which time mice are treated with purified mAb 6D8 or an irrelevant mAb (IgG2b; Sigma) by i.p. injection (5 mg/kg each mAb) every other day for up to 4 weeks. IgG2b doesn't recognize any human proteins and serves as an isotype control. Control tumors reach approximately 600 $mm^3$. Tumors are measured by Vernier calipers, and tumor volumes are scored as $(\text{length}\times\text{width})^2\times 0.5$ (in $mm^3$). Data is expressed as mean tumor volume ±SE for each treatment group (n>5 for each group). The tumors are harvested and analyzed for expression of Dsg2 in addition to other oncogenic markers such as EGFR. These experiments establish the feasibility of targeting Dsg2 using mAb 6D8.

Generation of CARs

Third generation, codon-optimized CARs are used containing the BiP (GRP-78) signal peptide, a scFv, CD8a hinge region, CD28 transmembrane and intracellular domains, and 4-1BB (CD137) and CD3 (intracellular domains in the pLVX-IRES-ZsGreen1 (Clontech) lentiviral vector (Magee et al. 2016, Oncoimmunology 5: e1227897; Magee, Abraham et al. 2018, Cancer Immunol Res. 6: 509-516). $V_L$ and $V_H$ variable regions are cloned from the mAb 6D8 and mAb 10D2 hybridoma by RT-PCR using degenerate primers and linked with a glycine-serine linker $(G_4S)_4$ by overlap extension PCR (Kochenderfer et al., 2009, J Immunother. 32: 689-702; Magee et al. 2016, Oncoimmunology 5: e1227897).

Functional Testing of Dsg2 CAR-T Cells (In Vitro)

Figures 10A, 10B:
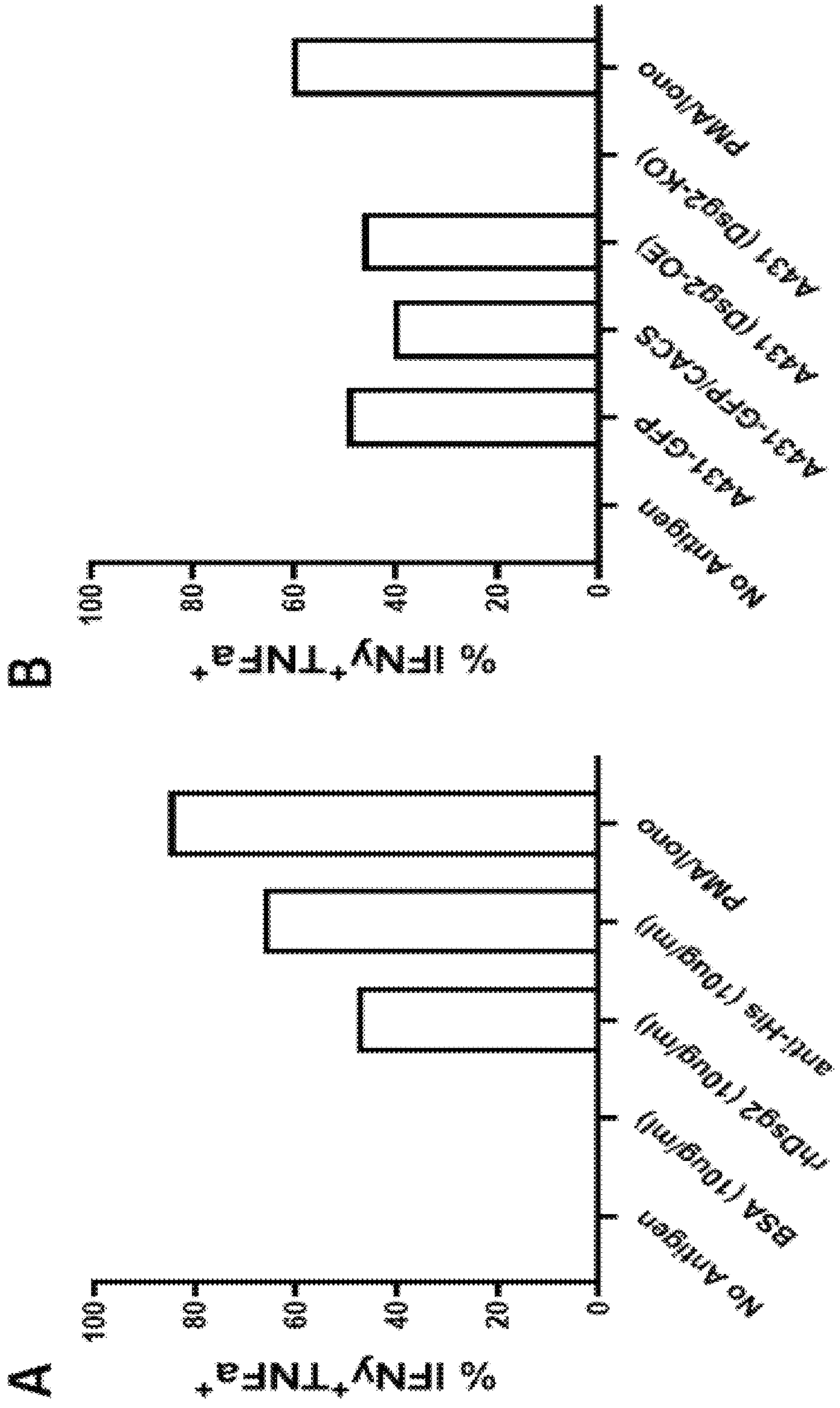
FIG. 10A and FIG. 10B depict results from exemplary experiments demonstrating Intracellular cytokine staining of antigen-stimulated Dsg2-specific CAR-T cells. Percentage of live CD8+, GFP+ T cells double-positive for IFNγ and TNFα cytokines (markers of antigen detection and T-cell activation).
Figures 11A, 11B:
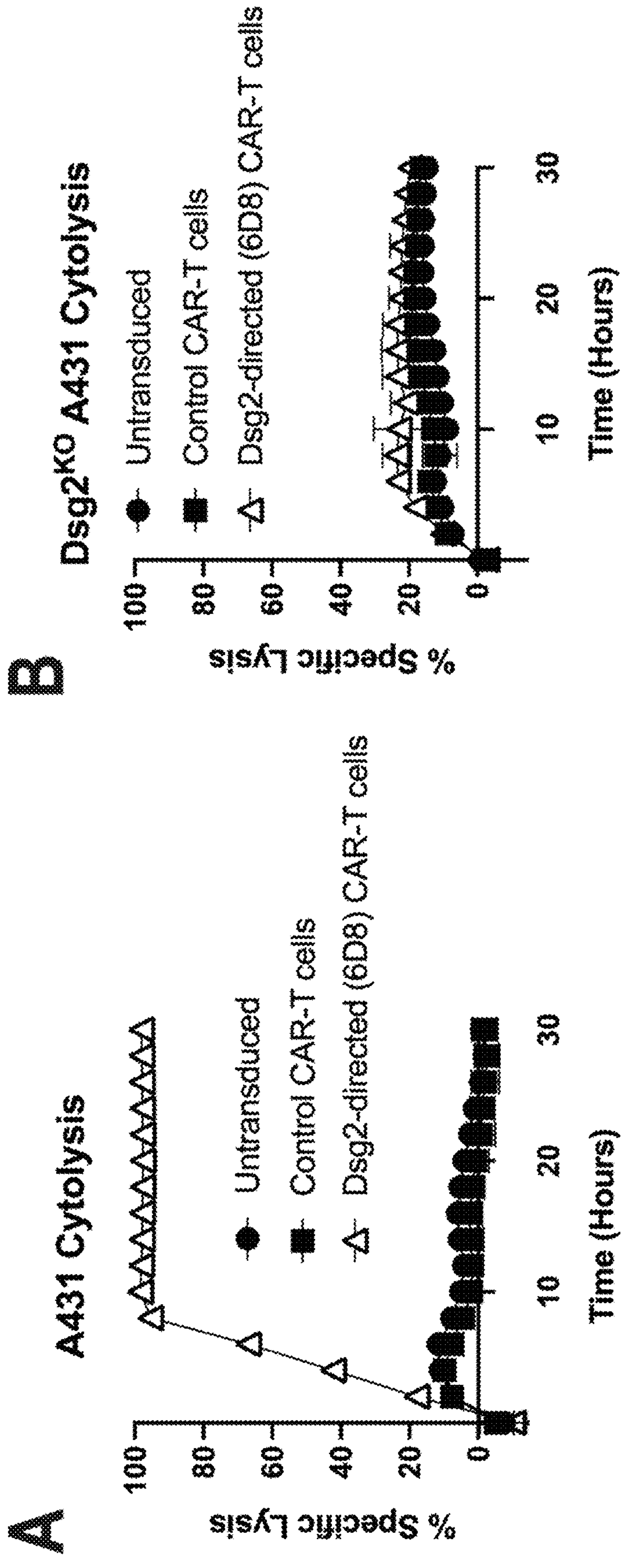
FIG. 11A and FIG. 11B depict results from exemplary experiments demonstrating CAR-T cell killing of SCC cell lines expressing surface Dsg2, but not in Dsg2-knockout SCC cells. xCELLigence real-time cell analysis (RTCA) demonstrating Dsg2-specific CAR-T cell cytotoxicity in A431 SCC parental cells (FIG. 11A), but not in A431 Dsg2 CRISPR/Cas9 knockout cells (FIG. 11B).

Target-recognition, cytokine production, and cytolysis by Dsg2-directed 6D8-28BBz CAR-T cells were examined in vitro (FIG. 10 and FIG. 11). 6D8 CAR-T cells produced TNFα and IFNγ following huma Dsg2 stimulation and positive control (anti-His; PMA/Iono) stimulation, but not in the absence of stimulation (FIG. 10A). Moreover, Dsg2-expressing A431 SCC cells, but not CRISPR-Cas9-mediated Dsg2-knockout A431 cells induced cytokine production (FIG. 10B) and were lysed (FIG. 11) by 6D8 CAR-T cells. Control CAR-T cells produced no cytokines in the presence of cells and did not lyse A431 cells (FIG. 11).

Testing of Dsg2 CAR-T Cells in Cell-Line-Derived Xenografts (CDX)

Figure 12A:
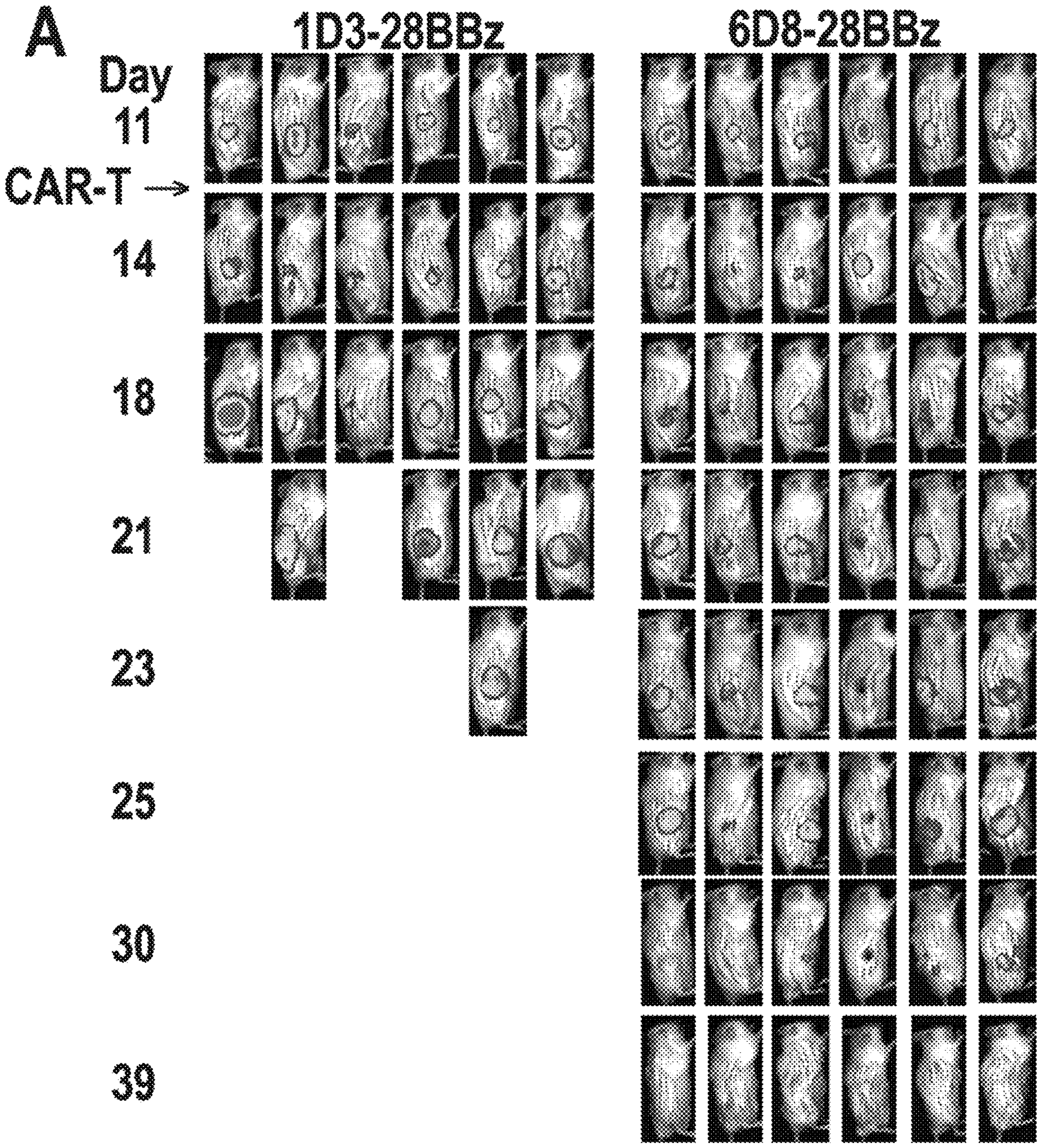
FIG. 12A through FIG. 12C depict results of exemplary experiments demonstrating in vivo CAR-T cell efficacy in treating A431 cSCC tumors. In vivo bioluminescence images (FIG. 12A) and tumor size measurements (FIG. 12B) demonstrating control-treated tumor progression and Dsg2 CAR-T-treated tumor regression. Survival analyses demonstrate rapid and complete mortality in control-treated animals and nearly 100% cure of Dsg2 CAR-T-treated animals (FIG. 12C).
Figures 12B, 12C:
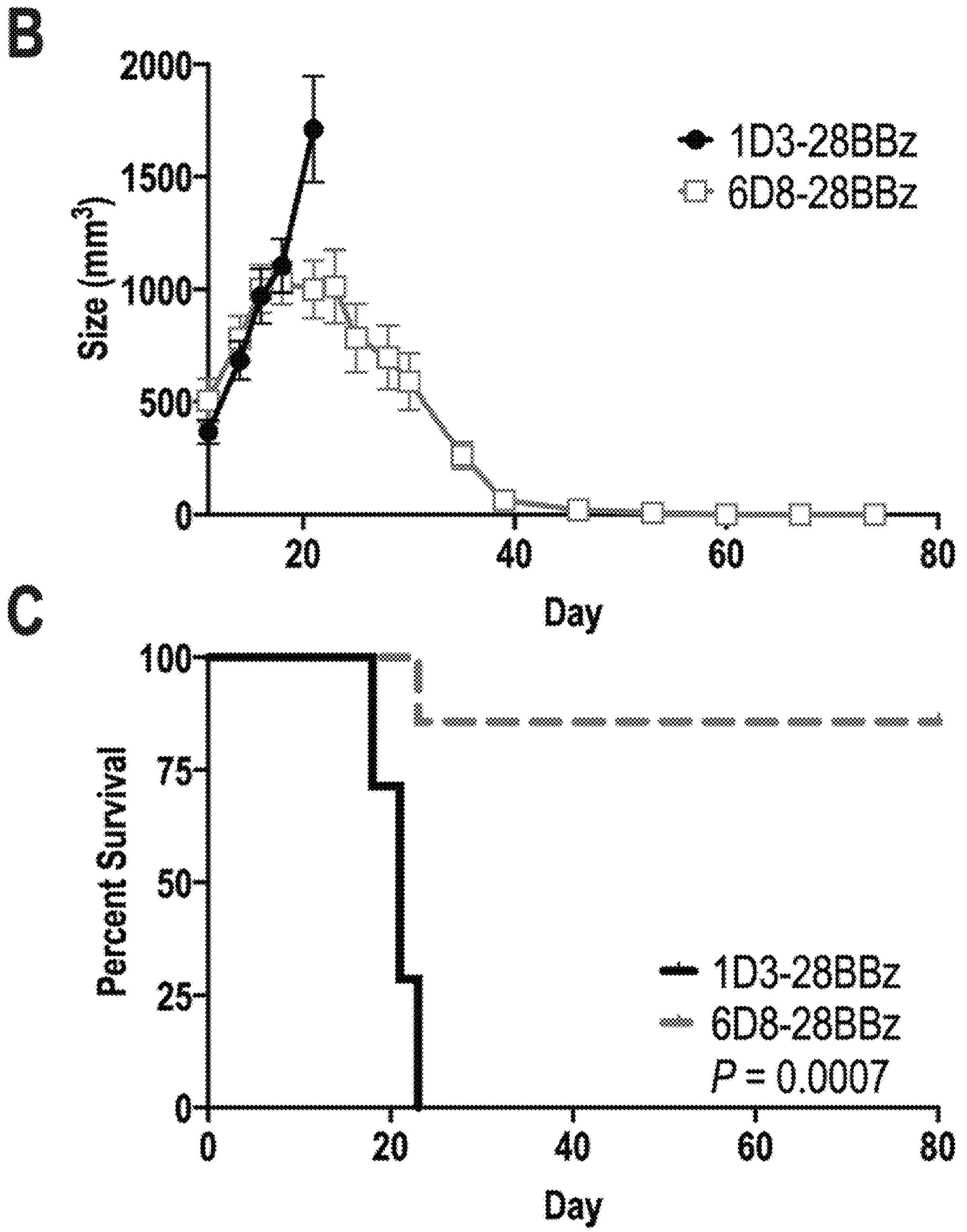

Following successful and specific recognition of Dsg2-expressing A431 SCC cells in vitro (FIG. 10 and FIG. 11), luciferase-expressing A431 tumors were established subcutaneously in NSG mice (FIG. 12). Control or 6D8 CAR-T cells were administered on day 12 when tumors averaged 500 $mm^3$. While tumors quickly progressed in control animals (FIGS. 12A and B), resulting in 100% mortality within 10 days of administration (FIG. 12C), tumors were eliminated in nearly all 6D8-28BBz CAR-T cell-treated animals (FIGS. 12A and B) which survived >80 days without relapse (FIG. 12C).

Dsg2 CAR-T Cells Persist Long Term

Figures 13A, 13B:
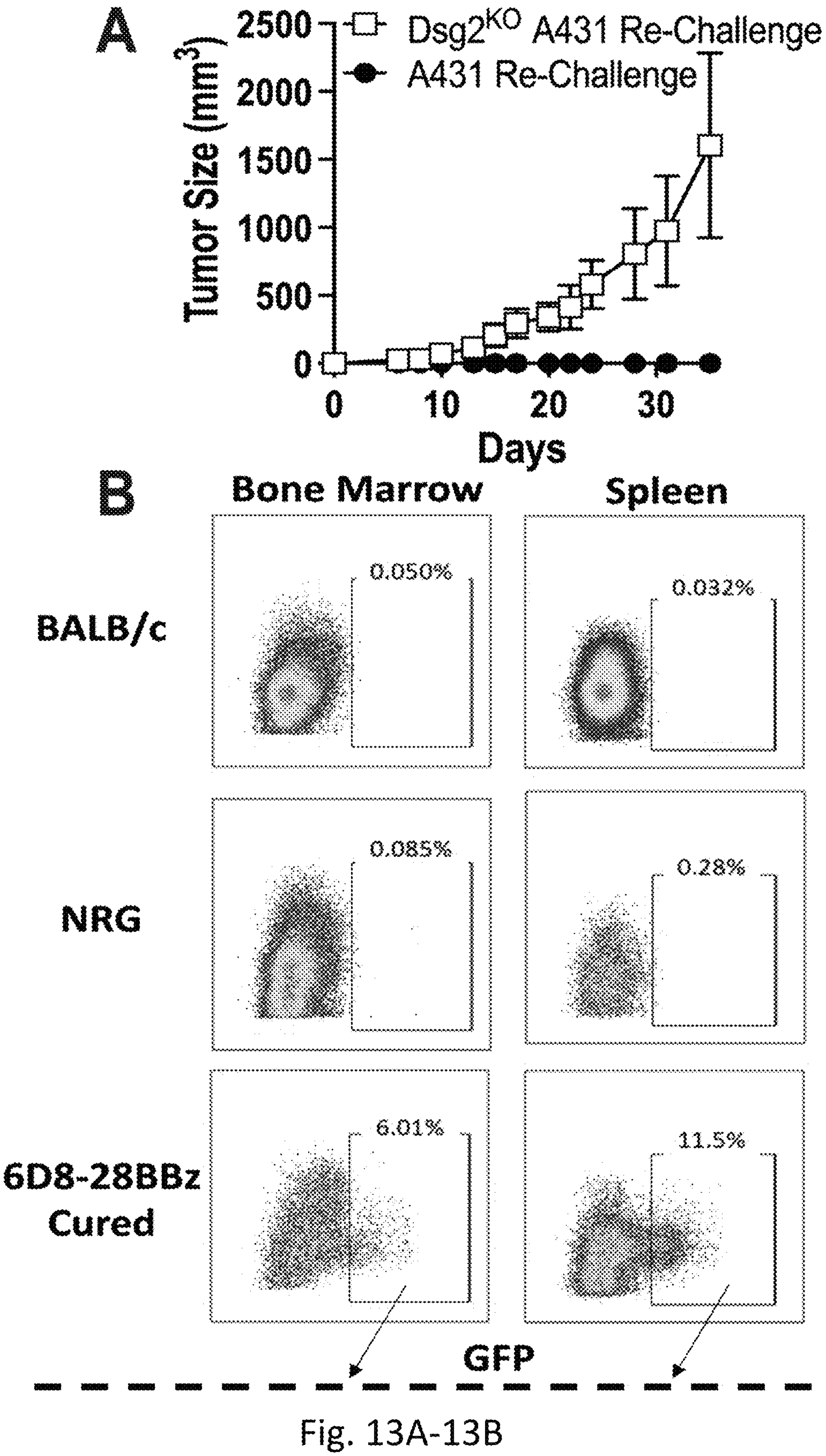
FIG. 13A through 13C depicts results of exemplary experiments demonstrating in vivo persistence of Dsg2-directed CAR-T cells. In vivo resistance of previously treated mice (100 days after initial tumor challenge in FIG. 12) to a second challenge with A431 cells, but not Dsg2 knockout A431 cells (FIG. 13A). Flow cytometry analyses of bone marrow and spleen demonstrate persistence of CAR+ (GFP+) T cells (FIG. 13B) with memory and effector phenotypes (FIG. 13C).
Figure 13C:
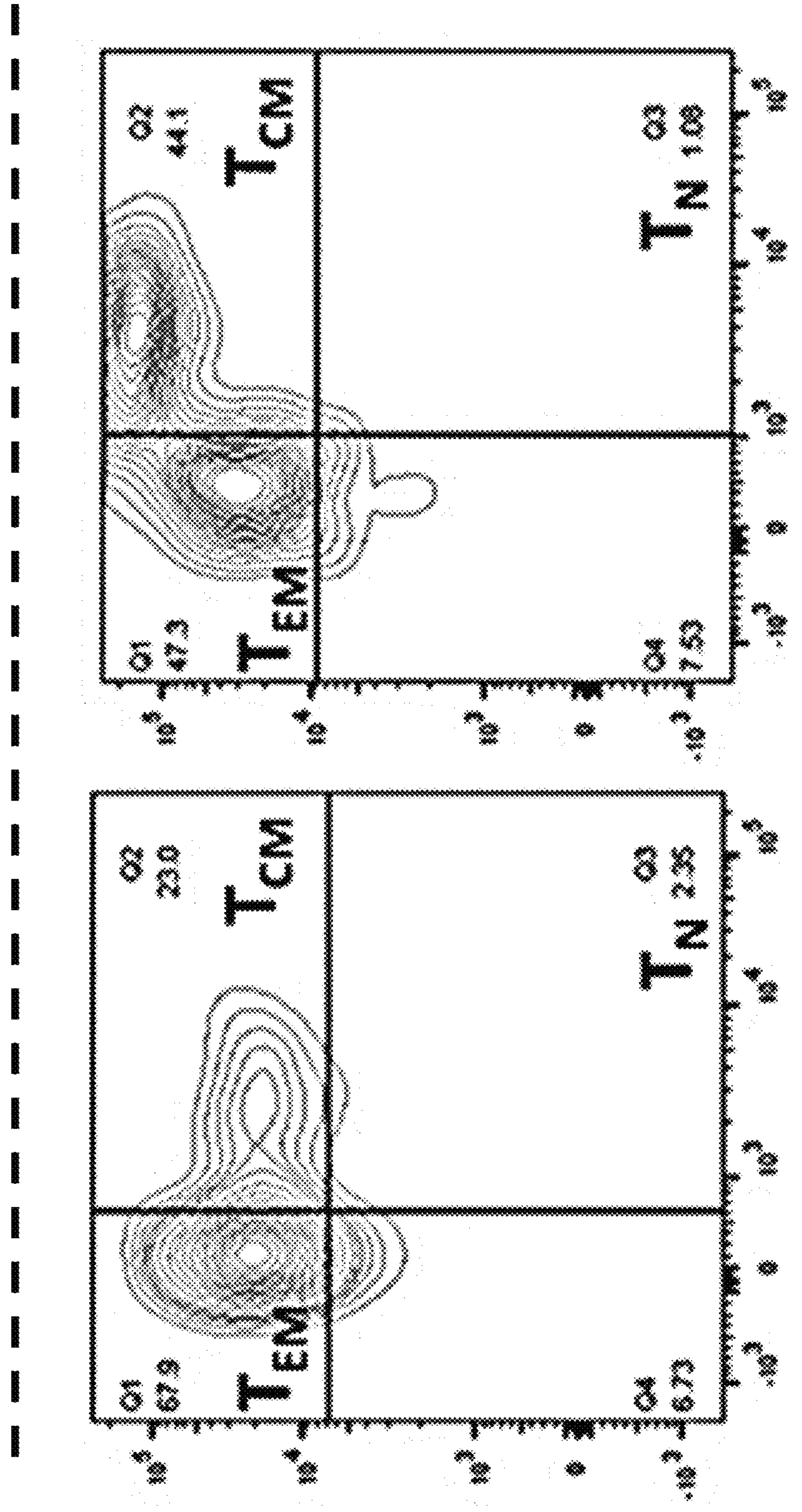

Following successful and specific elimination of Dsg2-expressing A431 SCC tumors in vivo (FIG. 12), surviving animals were re-challenged with A431 or Dsg2-knockout A431 cancer cells subcutaneously in NSG mice (FIG. 13). Re-challenged mice resisted A431 cells, but not Dsg2-knockout A431 cells (FIG. 13A). Moreover, spleen and bone marrow of those animals contained CAR-T cells (GFP+ cells; FIG. 13B) with a mixture of central and effector memory phenotypes (FIG. 13C).

10D2 CAR-T Cells

In addition to 6D8 CAR-T cells, 10D2 CAR-T cells were produced and their activity was explored. 10D2 CAR-T cells produce IFNγ and TNFα upon Dsg2 recognition and lyse Dsg2-expressing A431 SCC cells, although lysis is less than 6D8 CAR-T cells (FIG. 14A).

10D2 CAR-t Cell Safety

Unlike 6D8 mAb (and CAR-T) which recognizes only huma Dsg2, 10D2 mAb recognizes human and murine Dsg2, (Brennan and Mahoney, 2009, Cell Adh Migr. 3(2): 148-154; Gupta et al. 2015, Plos One, 10(3):e0120091) permitting safety evaluation in conventional mice. 10D2 CAR-T cells successfully lyse A431 SCC cells (FIG. 14A) but produce no toxicity in mice (FIG. 14B). Animals receiving $10^7$ CAR-T cells show no toxicity within ~2 wks (FIG. 14B), a timeframe in which CAR-T cell therapies have produced severe toxicity and death in patients (Hay et al., 2017, Blood, 130:2295-2306; Morgan et al., 2010, Mol Ther, 18:843-851) and mice (20% body weight loss in 3-4 days)(Yang et al. 2019, Journal for immunotherapy of cancer, 7:171).

10D2 and 6D8 CAR-T Cell Safety in Human Dsg2 Transgenic Mice

Human Dsg2 transgenic mice ($hDsg2^{Tg}$) produced from a BAC of the human Dsg2 locus were acquired from the University of Washington. These mice produce hDsg2 with a similar tissue and cellular distribution to humans (FIG. 14C) and are an excellent model for hDsg2 studies (Wang et al., 2012, J Virol, 86(11):6286-6302). Importantly, skin from these mice possesses robust Dsg2 expression which is recognizable by CAR-T cells. Keratinocytes isolated as single cell suspensions from hDsg2$^{Tg}$, but not wildtype, mice successfully stimulated 6D8 CAR-T cell cytokine secretion ex vivo (FIG. 14D). Control, 6D8, or 10D2 CAR-T cells were administered ($10^7$ CAR-T cells) to hDsg2$^{Tg}$ mice. Despite the expression of hDsg2 in tissues (FIG. 14C), including skin (FIG. 14D), animals showed no toxicity over 4 weeks of observation by body weight (FIG. 14E) and histology, a timeframe in which CAR-T cell therapies have produced severe toxicity and death in patients (Hay et al., 2017, Blood, 130:2295-2306; Morgan et al., 2010, Mol Ther, 18:843-851) and mice (Castellarin et al., 2020, CI Insight, 5:e136012; Qin et al., 2020, Oncoimmunology, 9(1):1806009).

Dsg2-Directed CAR-T Cell Therapy for Other Cancers

Recognition of numerous other cancer cells by 6D8 CAR-T cells resulting in effector cytokine production (FIG. 15A) and killing (FIG. 15B) was examined. All cancer lines tested successfully activated 6D8 CAR-T cells and were killed by them. Moreover, 6D8 CAR-T cells administered on day 17 of tumor growth successfully cured mice with DLD-1 colorectal cancer xenografts (FIG. 16).

Example 2: Dsg2-CARs

Figure 7:
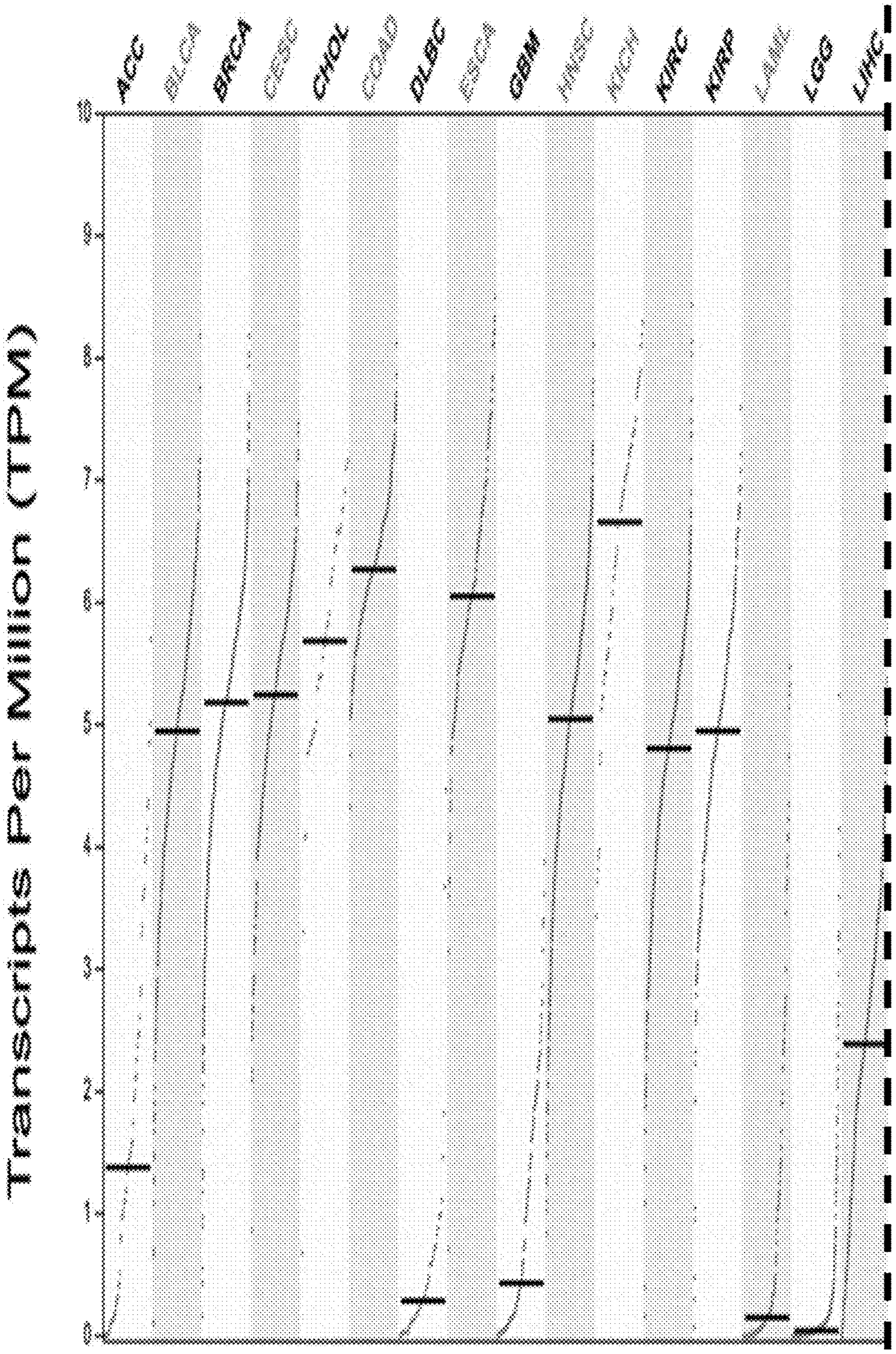
FIG. 7 depicts Dsg2 expression in selected solid cancers. RNAseq data was compiled from the TCGA and GTEx projects and analyzed and displayed using GEPIA (gepia.cancer-pku.cn). ACC, Adrenocortical carcinoma; BLCA, Bladder Urothelial Carcinoma; BRCA, Breast invasive carcinoma; CESC, Cervical squamous cell carcinoma and endocervical adenocarcinoma; CHOL, cholangiocarcinoma; COAD, Colon adenocarcinoma; DLBC, Lymphoid Neoplasm Diffuse Large B-cell Lymphoma; ESCA, Esophageal carcinoma; GBM, Glioblastoma multiforme; HNSC, Head and Neck squamous cell carcinoma; KICH, Kidney Chromophobe; KIRC, Kidney renal clear cell carcinoma; KIRP, Kidney renal papillary cell carcinoma; LAML, Acute Myeloid Leukemia; LGG, Brain Lower Grade Glioma; LIHC, Liver hepatocellular carcinoma; LUAD, Lung adenocarcinoma; LUSC, Lung squamous cell carcinoma; MESO, Mesothelioma; OV, Ovarian serous cystadenocarcinoma; PAAD, Pancreatic adenocarcinoma; PCPG, Pheochromocytoma and Paraganglioma; PRAD, Prostate adenocarcinoma; READ, Rectum adenocarcinoma; SARC, Sarcoma; SKCM, Skin Cutaneous Melanoma; STAD, Stomach adenocarcinoma; TGCT, Testicular Germ Cell Tumors; THCA, Thyroid carcinoma; THYM, Thymoma; UCEC, Uterine Corpus Endometrial Carcinoma; UCS, Uterine Carcinosarcoma; UVM, Uveal Melanoma.
Figure 7:
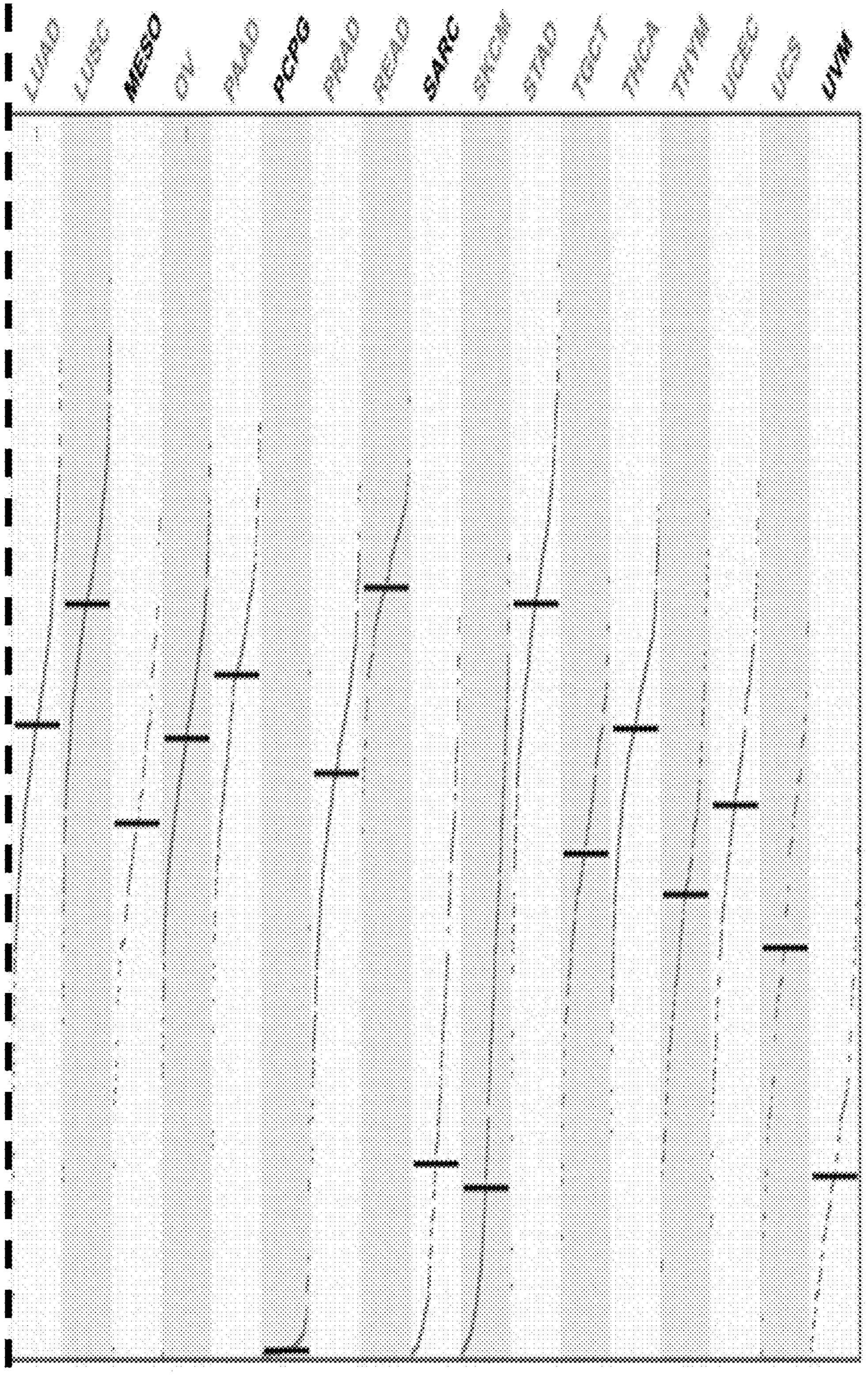

Solid tumor malignancies collectively remain the primary cause of cancer-related mortality. However, adoptive cell therapies have emerged as powerful tools within the immuno-oncology repertoire capable of directly addressing present obstacles. Previous demonstrations utilizing adoptively-transferred chimeric antigen receptor (CAR) engineered T cells targeting the 1B-cell-specific antigen, CD19, have proven highly efficacious for treatment of certain lymphomas and leukemias. Unlike CD19 which is restricted to a subset of liquid tumors and similar solid tumor targets (PSMA only in prostate, GUCY2C only in GI cancers, etc), desmoglein-2 (Dsg2) is a tumor-associated antigen that is expressed in many healthy tissues and is universally overexpressed in nearly all solid tumor cell types (FIG. 7).

Figure 9:
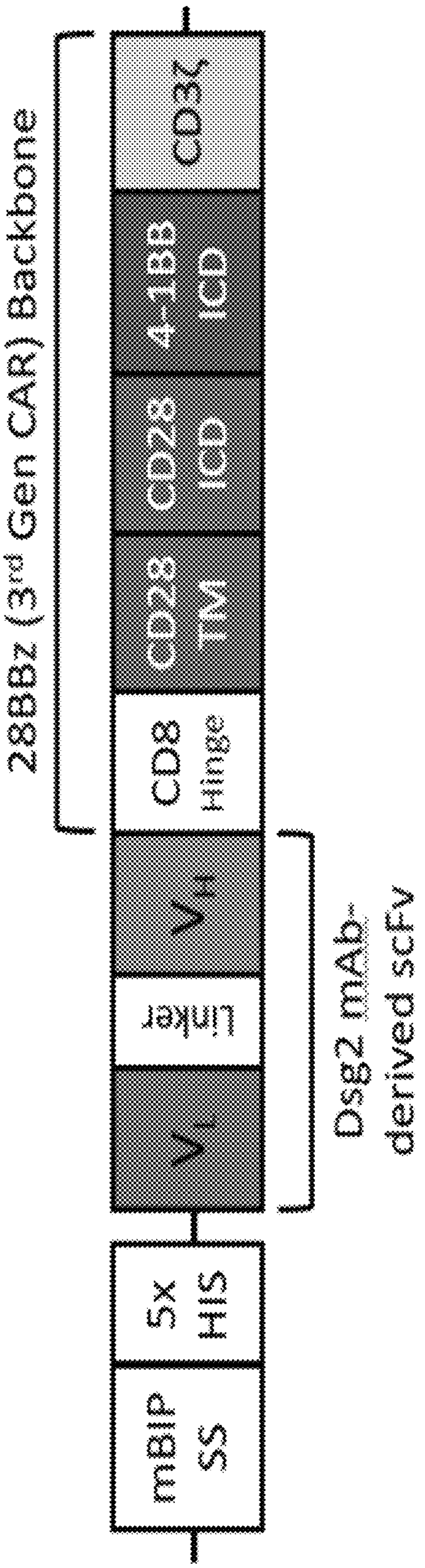
FIG. 9 depicts a 3rd generation CAR construct backbone combined with Dsg2-mAb-derived scFv. Current iteration of the CAR incorporated into mouse CD8+ T cells for testing Dsg2 antigen stimulation and effector functions in subsequent Figures. From left to right: (mBIP-SS) murine ER chaperone and signal sequence, (5×HIS) penta-histidine repeat, (VL) Dsg2 mAb-derived variable light chain, (Linker) scFv (G4S)4 flexible linker, (VH) Dsg2 mAb-derived variable heavy chain, (CD8 Hinge) non-signaling extracellular flexible module, (CD28 TM) CD28 costimulatory transmembrane domain, (CD28 ICD) CD28 costimulatory intracellular signaling domain, (4-1BB ICD) CD137 costimulatory intracellular signaling domain (CD3) intracellular signaling domain.

Dsg2 is a desmosomal cadherin protein expressed at basal levels and sequestered between cell-to-cell junctions in normal epithelia, but greatly overexpressed on the surface of transformed and malignant epithelial cells. While initially counterintuitive as a CAR target reflecting wide-spread expression in many vital tissues (such as heart), this unique sub-cellular expression profile implies an exploitable paradigm in which de-sequestration of Dsg2 can be targeted in solid tumors, without collateral toxicity in normal epithelia (FIG. 8 and FIG. 14B). CAR constructs (FIG. 9) containing single-chain variable fragments (scFvs), adapted from proprietary monoclonal antibodies (mAbs), capable of targeting huma Dsg2 protein have been developed. Expression of these constructs in T cells, producing Dsg2-directed CAR-T cells, confers the ability to detect surface Dsg2 on a variety of cancer cell lines, as well as by plate-coated Dsg2 protein (FIG. 10). Dsg2-directed CAR-T cells kill solid tumor cells in vitro, without cytolysis in Dsg2-knockout cells, indicating Dsg2-specificity (FIG. 11). Moreover, administration of Dsg2 CAR-T cells targeting mouse Dsg2 produced no toxicity upon administration to mice (FIG. 13B). Together, Dsg2-targeted CARs provide potent cytolytic effector function and antitumor efficacy when expressed in T cells. Moreover, other cell types are likely to provide similar benefits (such as NK cells) and CAR-T/NK cells could be modified and/or combined with other strategies to improve safety and efficacy, including but not limited to those listed below (Potential Modifications, Combinations, and/or Variants).

In its most basic form:

1. T cells are collected from a patient, Dsg2 CAR (FIG. 9) is engineered into the cells, and the newly formed CAR-T cells are administered to the same patient.

Or

2. NK cells are collected from a centralized source (blood banks or cord blood banks), modified to express a Dsg2 CAR at large-scale, producing CAR-NK cells that are banked and administered to any patient with a Dsg2-expressing solid tumor. This is a large-scale manufacturing approach for universal, off-the-shelf Dsg2 CAR-NK cell therapy that can be used in nearly any cancer patient, in contrast to the bespoke cancer-restricted, patient-specific CAR-T cell approach used now.

The CAR can be expressed in various T cells (e.g., αβ, γδ; CD4+, CD8+), natural killer cells, (e.g., NK-92, NK-92MI, NKL), macrophages (e.g., M1, M2), and other cell types.

The CAR can be a 1st generation CAR (scFV+CD3ζ), a 2nd generation CAR (scFv+CD28/4-1BB/OX40/ICOS+CD3ζ), a 3rd generation CAR construct (2$^{nd}$ generation CAR backbone+additional CD28/4-1BB/OX40/ICOS), a 4th generation CAR construct or T-cells redirected for universal cytokine-mediated killing (TRUCKs), (2nd generation CAR backbone+constitutive/inducible chemokine [e.g. IL-2, IL-12, IL-15, etc.] component), or a 5th generation CAR (4th generation CAR+intracellular domains of cytokine receptors [e.g. IL-2Rβ]) constructs.

The Dsg2 CAR can be used in combination with suicide genes: inducible caspase 9 ("iCasp9"), herpes simplex virus thymidine kinase (HSV-TK), etc.

The Dsg2 CAR can be a "DualCAR" (more than one CAR per immune cell) and/or "TandemCAR" (single bivalent/bispecific CAR targeting more than one antigen) formats.

The Dsg2 CAR can be a logic-gated CAR ("OR", "AND" and "NOT" Boolean-gated safety switches) formats.

The Dsg2 CAR can be used in combination with "iCARs" (normal tissue antigen-specific inhibitory CARs conjugated to PD-1, CTLA-4, etc.) The Dsg2 CAR can be a "SynNotch" (synthetic Notch receptors) CAR.

The immune cell can be a CRISPR/Cas9-modified immune cell (e.g. removal of PD-1, CTLA-4, TIM-3, LAG-3, etc.) The Dsg2 CAR can be used in combination with immune checkpoint blockade therapies (anti-PD-1/PD-L1, anti-CTLA-4, anti-TIM-3, etc.) The Dsg2 CAR can be used in combination with addition of cytokines (IL-2, IL-15, IL-18, etc.) before/during/after adoptive transfer.

The Dsg2 CAR can be used in tandem with vaccination or oncolytic viruses.

The Dsg2 CAR can be used for targeting of tumor-specific variations of Dsg2 (mutations, cleavage productions, differential glycosylation, etc).

The Dsg2 CAR can be used for modification of CAR-T cell homing (IV vs. IP vs. local/regional delivery, CRISPR-targeting of homing molecules, homing molecule transgene delivery), etc.

Example 3: Sequences

TABLE 1

| 6D8 Antibody | | | | |
|---|---|---|---|---|
| | SEQ ID NO: | Sequence | SEQ ID NO: | Sequence |
| Heavy Chain | | | | |
| CDR1 | 1 | ggctacacgttcaccaactacggt | 2 | gytftnyg |
| CDR2 | 3 | atcaatacttacaccggtaatcca | 4 | intytgnp |
| CDR3 | 5 | gctcgcgacaggggcaactccttcgac<br>tat | 6 | ardrgnsfdy |
| Full length | 7 | cagatccagcttgtgcagageggcccc<br>gagctgaagaagcccggggagactgt<br>caagatctcttgcaaggcgtccggctac<br>acgttcaccaactacggtatgaactggg<br>tgaagcaggccccggggcgtggcttg<br>aaatggatgggttggatcaatacttaca<br>ccggtaatccaacctacgcggatgactt<br>caagggccgcttcgatttttcgctggag<br>acctccgctagcactgcctacctgcaaa<br>ttaacaacctcaaaaacgaggacatgg<br>ccatctatttctgtgctcgcgacagggg<br>caactccttcgactattggggccagggt<br>accacactgaccgtctcttct | 8 | qiqlvqsgpelkkpget<br>vkisckasgytftnygm<br>nwvkqapgrglkwmg<br>wintytgnptyaddfkg<br>rfdfsletsastaylqinnl<br>knedmaiyfcardrgns<br>fdywgqgttltvss |
| Light Chain | | | | |
| CDR1 | 9 | gagaacatctactcgaac | 10 | eniysn |
| CDR2 | 11 | atcgccatt | 12 | iai |
| CDR3 | 13 | cagcacttttggggcactccgcgcacc | 14 | qhfwgtprt |
| Full length | 15 | gacatccagatgacccagagccctgct<br>agtctctccgtgtccgttggcgagacgg<br>tgaccatcacctgccgcgcatccgaga<br>acatctactcgaacctggcctggtacca<br>gcagaagcagggcaagagccctcag<br>ctgctggtgtacatcgccattaacctgg<br>cggacggcgtaccctctcggttttcagg<br>gagcggctcggggacccagtacagtc<br>taaaaattaattcccttcagtccgaagatt<br>tcggcaactattactgtcagcacttttgg<br>ggcactccgcgcaccttcggcggagg<br>taccaagctggagatcaag | 16 | diqmtqspaslsvsvge<br>tvtitcraseniysnlawy<br>qqkqgkspqllvyiainl<br>adgvpsrfsgsgsgtqy<br>slkinslqsedfgnyycq<br>hfwgtprtfgggtkleik |

TABLE 2

| 10D2 Antibody | | | | |
|---|---|---|---|---|
| | SEQ ID NO: | Sequence | SEQ ID NO: | Sequence |
| Heavy Chain | | | | |
| CDR1 | 17 | agctacatcttgcat | 18 | syilh |
| CDR2 | 19 | tatattaacccgtacaacgacgccacca<br>agtacaacgagaaatttaagggc | 20 | yinpyndatkynekfkg |
| CDR3 | 21 | acaccacagcctat | 22 | ittay |
| Full length | 23 | gaggtgcagctgcagcagagcgggc<br>ccgagctggtgaatccaggcgcgtca<br>gtgaagatgtcatgcaaagcttctggct<br>actccttcaccagctacatcttgcattgg<br>gtcaagcagaagcctggacagggtct<br>ggagtggatcggttatattaacccgtac<br>aacgacgccaccaagtacaacgagaa<br>atttaagggcaaggccacgctcactag<br>cgataaaagctcgtccacggcctacat<br>ggaattgagttccgtcacctccgagga<br>cagcgcggtgtactactgttgctctatga<br>tcaccacagcctattgggcgtactggg<br>gccagggcactcttgttacagtatctgct | 24 | evqlqqsgpelvnpgas<br>vkmsckasgysftsyil<br>hwvkqkpgqglewig<br>yinpyndatkynekfkg<br>katltsdkssstaymels<br>svtsedsavyyccsmitt<br>aywaywgqgtlvtvsa |

TABLE 2-continued

| 10D2 Antibody | SEQ ID NO: | Sequence | SEQ ID NO: | Sequence |
|---|---|---|---|---|
| Light Chain | | | | |
| CDR1 | 25 | aaatcctctcaatctatcctgtacggctc gacccagaagaactacctggca | 26 | kssqsilygstqknyla |
| CDR2 | 27 | tgggcttccactcgtgagagc | 28 | wastres |
| CDR3 | 29 | caccagtacctttcgagctacacc | 30 | hqylssyt |
| Full length | 31 | aacatcatgatgacccagagcccgtcg tccctcaccgtgtccgctggcgagaag gtgaccatgtcttgcaaatcctctcaatc tatcctgtacggctcgacccagaagaa ctacctggcatggtaccagcagaagcc cgggcagagccctaagctgctgatttat tgggcttccactcgtgagagcggggtc cccgaccgcttcaccggctccggctcc ggcaccgacttcaccctgaccatctctt ccgtgcaggccgaagatctggccgtgt attactgtcaccagtacctttcgagctac accttcggcggtggcactaagttagag atcaag | 32 | nimmtqspssltvsage kvtmsckssqsilygstq knylawyqqkpgqsp klliywastresgvpdrft gsgsgtdftltissvqaed lavyychqylssytfgg gtkleik |

SEQ ID NO: 33 - 6D8-28BBz_CAR_(DNA)
CD8 Leader Sequence (nt 1-63); 6D8 scFv (nt 64 . . . 798); 6D8 Kappa Light Chain (nt 64 . . . 384); 6D8 Kappa Light Chain CDR1 (nt 142 . . . 159); 6D8 Kappa Light Chain CDR2 (nt 211 . . . 219); 6D8 Kappa Light Chain CDR3 (nt 328 . . . 354); Linker (nt 385 . . . 447); 6D8 Heavy Chain (nt 448 . . . 798); 6D8 Heavy Chain CDR1 (nt 523 . . . 546); 6D8 Heavy Chain CDR2 (nt 598 . . . 621); 6D8 Heavy Chain CDR3 (nt 736 . . . 765); CD8 Hinge (nt 799 . . . 933); CD8 Transmembrane (nt 934 . . . 1005); CD28 ICD (nt 1006 . . . 1128); 4-1BB ICD (nt 1129 . . . 1254); CD3} ICD (nt 1255 . . . 1590)

atggcattgcctgttacagctctgctgctgcccctggctctgcttctgcatgctgccagacctgacatccagatgacccagagccc tgctagtctctccgtgtccgttggcgagacggtgaccatcacctgccgcgcatccgagaacatctactcgaacctggcctggtac cagcagaagcagggcaagagccctcagctgctggtgtacatcgccattaacctggcggacggcgtaccctctcggttttcagg gagcggctcggggacccagtacagtctaaaaattaattcccttcagtccgaagatttcggcaactattactgtcagcacttttgggg cactccgcgcaccttcggcggaggtaccaagctggagatcaagtcgggcggaggaggcagcggcggcgggggttccggtg gaggcggctctggcggcgggggttctcagatccagcttgtgcagagcggccccgagctgaagaagcccggggagactgtca agatctcttgcaaggcgtccggctacacgttcaccaactacggtatgaactgggtgaagcaggccccggggcgtggcttgaaat ggatgggttggatcaatacttacaccggtaatccaacctacgcggatgacttcaagggccgcttcgatttttcgctggagacctcc gctagcactgcctacctgcaaattaacaacctcaaaaacgaggacatggccatctatttctgtgctcgcgacaggggcaactcctt cgactattggggccagggtaccacactgaccgtctcttctacaacaacccctgctcctcggcctcctacaccagctcctacaattg ccagccagcctctgtctctgaggcccgaagcttgtagacctgctgctggcggagccgtgcatacaagaggactggatttcgcct gcgacatctacatctgggctcctctggccggaacatgtggcgtgctgctgctgagcctggtcatcaccctgtactgccggtccaa gagaagcagactgctgcacagcgactacatgaacatgacccctagacggcccggacctaccagaaagcactaccagccttac gctcctcctcgggacttcgctgcctacagaagcaagcggggcagaaagaagctgctgtacatcttcaagcagcccttcatgcgg cccgtgcagaccacacaagaggaagatggctgctcctgcagattccccgaggaagaagaaggcggctgcgagctgagagtg aagttcagcagatccgctgacgcccctgcctacaagcagggacagaaccagctgtacaacgagctgaacctggggagaaga gaagagtacgacgtgctggacaagcggagaggcagagatcctgagatgggcggcaagcccagacggaagaatcctcaaga gggcctgtataatgagctgcagaaagacaagatggccgaggcctacagcgagatcggaatgaagggcgagcgcagaagag gcaagggacacgatggactgtaccagggcctgagcaccgccaccaaggatacctatgatgccctgcacatgcaggccctgcc tccaagatag -continued SEQ ID NO: 34 - 6D8-28BBz_CAR (amino acid)
CD8 Leader Sequence (residues 1 . . . 21); 6D8 scFV (residues 22 . . . 266); 6D8 Kappa Light Chain (residues 22 . . . 128); 6D8 Kappa Light Chain CDR1 (residues 48 . . . 53); 6D8 Kappa Light Chain CDR2 (residues 71 . . . 73); 6D8 Kappa Light Chain CDR3 (residues 110 . . . 118); Linker (residues 129 . . . 149); 6D8 Heavy Chain (residues 150 . . . 266); 6D8 Heavy Chain CDR1 (residues 175 . . . 182); 6D8 Heavy Chain CDR2 (residues 200 . . . 207); 6D8 Heavy Chain CDR3 (residues 246 . . . 255); CD8 Hinge (residues 267 . . . 311); CD8 Transmembrane (residues 312 . . . 335); CD28 ICD (residues 336 . . . 376); 4-1BB ICD (residues 377 . . . 418); CD32 ICD (residues 419 . . . 530)

malpvtalllplalllhaarpdiqmtqspaslsvsvgetvtitcraseniysnlawyqqkqgkspqllvyiainladgvpsrfsg sgsgtqyslkinslqsedfgnyycqhfwgtprtfgggtkleiksggggsggggsggggsggggsqiqlvqsgpelkkpget vkisckasgytftnygmnwvkqapgrglkwmgwintytgnptyaddfkgrfdfsletsastaylqinnlknedmaiyfca rdrgnsfdywgqgttltvssttpaprpptpaptiasqplslrpeacrpaaggavhtrgldfacdiyiwaplagtcgvlllslvitl ycrskrsrllhsdymnmtprrpgptrkhyqpyapprdfaayrskrgrkkllyifkqpfmrpvqttqeedgcscrfpeeeegg celrvkfsrsadapaykqgqnqlynelnlgrreeydvldkrrgrdpemggkprrknpqeglynelqkdkmaeayseigm kgerrrgkghdglyqglstatkdtydalhmqalppr SEQ ID NO: 35 10D2-28BBz_CAR_(DNA)
CD8 Leader Sequence (nt 1 . . . 63); 10D2 scFv (nt 64 . . . 816); 10D2 Kappa Light Chain (nt 64 . . . 399); 10D2 Kappa Light Chain CDR1 (nt 133 . . . 183); 10D2 Kappa Light Chain CDR2 (nt 229 . . . 249); 10D2 Kappa Light Chain CDR3 (nt 346 . . . 369); Linker (nt 400 . . . 462); 10D2 Heavy Chain (nt 463 . . . 816); 10D2 Heavy Chain CDR1 (nt 553 . . . 567); 10D2 Heavy Chain CDR2 (nt 610 . . . 660); 10D2 Heavy Chain CDR3 (nt 760 . . . 774); CD8 Hinge (nt 817 . . . 951); CD8 Transmembrane (nt 952 . . . 1023); CD28 ICD (nt 1024 . . . 1146); 4-1BB ICD (nt 1147 . . . 1272); CD32 ICD (nt 1273 . . . 1608)

atggcattgcctgttacagctctgctgctgcccctggctctgcttctgcatgctgccagacctaacatcatgatgacccagagccc gtcgtccctcaccgtgtccgctggcgagaaggtgaccatgtcttgcaaatcctctcaatctatcctgtacggctcgacccagaaga actacctggcatggtaccagcagaagcccgggcagagccctaagctgctgatttattgggcttccactcgtgagagcggggtcc ccgaccgcttcaccggctccggctccggcaccgacttcaccctgaccatctcttccgtgcaggccgaagatctggccgtgtatta ctgtcaccagtacctttcgagctacaccttcggcggtggcactaagttagagatcaagtcgggggggggaggaagtggcgggg gtggttctggcggcggtggttccggcggaggagggtccgaggtgcagctgcagcagagcgggcccgagctggtgaatccag gcgcgtcagtgaagatgtcatgcaaagcttctggctactccttcaccagctacatcttgcattgggtcaagcagaagcctggaca gggtctggagtggatcggttatattaacccgtacaacgacgccaccaagtacaacgagaaatttaagggcaaggccacgctca ctagcgataaaagctcgtccacggcctacatggaattgagttccgtcacctccgaggacagcgcggtgtactactgttgctctatg atcaccacagcctattgggcgtactggggccagggcactcttgttacagtatctgctacaacaacccctgctcctcggcctcctac accagctcctacaattgccagccagcctctgtctctgaggcccgaagcttgtagacctgctgctggcggagccgtgcatacaag aggactggatttcgcctgcgacatctacatctgggctcctctggccggaacatgtggcgtgctgctgctgagcctggtcatcacc ctgtactgccggtccaagagaagcagactgctgcacagcgactacatgaacatgacccctagacggcccggacctaccagaa agcactaccagccttacgctcctcctcgggacttcgctgcctacagaagcaagcggggcagaaagaagctgctgtacatcttca agcagcccttcatgcggcccgtgcagaccacacaagaggaagatggctgctcctgcagattccccgaggaagaagaaggcg gctgcgagctgagagtgaagttcagcagatccgctgacgcccctgcctacaagcagggacagaaccagctgtacaacgagct gaacctggggagaagagaagagtacgacgtgctggacaagcggagaggcagagatcctgagatgggcggcaagcccaga cggaagaatcctcaagagggcctgtataatgagctgcagaaagacaagatggccgaggcctacagcgagatcggaatgaag ggcgagcgcagaagaggcaagggacacgatggactgtaccagggcctgagcaccgccaccaaggatacctatgatgccctg cacatgcaggccctgcctccaagatag -continued SEQ ID NO: 36 10D2-28BBz_CAR_(amino acid)
CD8 Leader Sequence (residues 1 . . . 21); 10D2 scFv (residues 22 . . . 272); 10D2 Kappa Light Chain (residues 22 . . . 133); 10D2 Kappa Light Chain CDR1 (residues 45 . . . 61); 10D2 Kappa Light Chain CDR3 (residues 77 . . . 83); 10D2 Kappa Light Chain CDR3 (residues 116 . . . 123); Linker (residues 134 . . . 154); 10D2 Heavy Chain (residues 155 . . . 272); 10D2 Heavy Chain CDR1 (residues 185 . . . 189); 10D2 Heavy Chain CDR2 (residues 204 . . . 220); 10D2 Heavy Chain CDR3 (residues 254 . . . 258); CD8 Hinge (residues 273 . . . 317); CD8 Transmembrane (residues 318 . . . 341); CD28 ICD (residues 342 . . . 382); 4-1BB ICD (residues 383 . . . 424); CD32 ICD (residues 425 . . . 536)

```
malpvtalllplalllhaarpnimmtqspssltvsagekvtmsckssqsilygstqknylawyqqkpgqspklliywastres

gvpdrftgsgsgtdftltissvqaedlavyychqylssytfgggtkleiksggggsggggsggggsggggsevqlqqsgpelv

npgasvkmsckasgysftsyilhwvkqkpgqglewigyinpyndatkynekfkgkatltsdkssstaymelssvtsedsa

vyyccsmittaywaywgqgtlvtvsatttpaprpptpaptiasqplslrpeacrpaaggavhtrgldfacdiyiwaplagtcg

vlllslvitlycrskrsrllhsdymnmtprrpgptrkhyqpyapprdfaayrskrgrkkllyifkqpfmrpvqttqeedgcscrf

peeeeggcelrvkfsrsadapaykqgqnqlynelnlgrreeydvldkrrgrdpemggkprrknpqeglynelqkdkmae

ayseigmkgerrrgkghdglyqglstatkdtydalhmqalppr
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A composition comprising a chimeric antigen receptor (CAR) molecule comprising a domain that specifically binds to Dsg2, wherein the domain that specifically binds to Dsg2 comprises an antibody or fragment thereof selected from the group consisting of:

a) an antibody or fragment thereof comprising a variable heavy chain sequence comprising the CDR sequences of SEQ ID NO:2, SEQ ID NO:4 and SEQ ID NO: 6 and a variable light chain sequence comprising the CDR sequences of SEQ ID NO: 10, SEQ ID NO:12 and SEQ ID NO: 14; and b) an antibody or fragment thereof comprising a variable heavy chain sequence comprising the CDR sequences of SEQ ID NO:18, SEQ ID NO:20 and SEQ ID NO: 22 and a variable light chain sequence comprising the CDR sequences of SEQ ID NO: 26, SEQ ID NO:28 and SEQ ID NO:30.

2. The composition of claim 1, wherein the domain that specifically binds to Dsg2 comprises an scFv antibody fragment.

3. The composition of claim 1, wherein the antibody comprises a variable heavy chain and variable light chain sequence selected from the group consisting of:

a) a variable heavy chain sequence of SEQ ID NO:8 and a variable light chain sequence of SEQ ID NO: 16;

b) a variable heavy chain sequence of SEQ ID NO:24 and a variable light chain sequence of and SEQ ID NO: 32 c) a sequence having at least 95% identity to a variable heavy chain sequence selected from the group consisting of SEQ ID NO:8 and a variable light chain sequence of SEQ ID NO:16, wherein the variation is outside of the CDR sequences;

d) a sequence having at least 95% identity to a variable heavy chain sequence of SEQ ID NO:24 and a variable light chain sequence of SEQ ID NO:32, wherein the variation is outside of the CDR sequences;

e) a fragment comprising at least 80% of the full-length sequence of a variable heavy chain sequence of SEQ ID NO:8 and a variable light chain sequence of SEQ ID NO:16, wherein the fragment comprises at least the CDR sequences; and f) a fragment comprising at least 80% of the full-length sequence of a variable heavy chain sequence of SEQ ID NO:24 and a variable light chain sequence of and SEQ ID NO:32, wherein the fragment comprises at least the CDR sequences.

4. The composition of claim 1, wherein the CAR comprises a sequence selected from the group consisting of:

a) a sequence selected from the group consisting of SEQ ID NO:34 and SEQ ID NO:36;

b) a sequence having at least 95% identity to a sequence selected from the group consisting of SEQ ID NO:34 and SEQ ID NO:36; and c) a fragment comprising at least 80% of the full-length sequence of a sequence selected from the group consisting of SEQ ID NO:34 and SEQ ID NO:36.

5. The composition of claim 1, further comprising at least one selected from the group consisting of a pharmaceutically acceptable excipient and an adjuvant.

6. A composition comprising a nucleic acid molecule, or combination of nucleic acid molecules, encoding a CAR molecule comprising a domain that specifically binds to Dsg2 wherein the domain that specifically binds to Dsg2 comprises an antibody or fragment thereof selected from the group consisting of:

a) an antibody or fragment thereof comprising a variable heavy chain sequence comprising the CDR sequences of SEQ ID NO:2, SEQ ID NO:4 and SEQ ID NO: 6 and a variable light chain sequence comprising the CDR sequences of SEQ ID NO: 10, SEQ ID NO: 12 and SEQ ID NO: 14; and b) an antibody or fragment thereof comprising a variable heavy chain sequence comprising the CDR sequences of SEQ ID NO:18, SEQ ID NO:20 and SEQ ID NO: 22 and a variable light chain sequence comprising the CDR sequences of SEQ ID NO: 26, SEQ ID NO:28 and SEQ ID NO:30.

7. The composition of claim 6, wherein the domain that specifically binds to Dsg2 comprises an scFv antibody fragment.

8. The composition of claim 6, wherein the nucleic acid molecule encodes an antibody or fragment thereof comprising a variable heavy chain and variable light chain sequence selected from the group consisting of:

a) a variable heavy chain sequence of SEQ ID NO:8 and a variable light chain sequence of SEQ ID NO: 16;

b) a variable heavy chain sequence of SEQ ID NO:24 and a variable light chain sequence of and SEQ ID NO: 32 c) a sequence having at least 95% identity to a variable heavy chain sequence of SEQ ID NO:8 and a variable light chain sequence of SEQ ID NO: 16, wherein the variation is outside of the CDR sequences;

d) a sequence having at least 95% identity to a variable heavy chain sequence of SEQ ID NO:24 and a variable light chain sequence of SEQ ID NO:32, wherein the variation is outside of the CDR sequences;

e) a fragment comprising at least 80% of the full-length sequence of a variable heavy chain sequence of SEQ ID NO:8 and a variable light chain sequence of SEQ ID NO: 16, wherein the fragment comprises at least the CDR sequences; and f) a fragment comprising at least 80% of the full-length sequence of a variable heavy chain sequence of SEQ ID NO:24 and a variable light chain sequence of SEQ ID NO:32, wherein the fragment comprises at least the CDR sequences.

9. The composition of claim 8, wherein the nucleic acid molecule, or combination thereof, comprises nucleotide sequences encoding CDRs selected from the group consisting of:

a) SEQ ID NO:1, SEQ ID NO:3, SEQ ID NO:5, SEQ ID NO:9, SEQ a) ID NO: 11 and SEQ ID NO: 13; and b) SEQ ID NO: 17, SEQ ID NO:19, SEQ ID NO:21, SEQ ID NO:25, SEQ ID NO:27 and SEQ ID NO:29.

10. The composition of claim 9, wherein the nucleic acid molecule, or combination thereof, comprises at least one nucleotide sequences selected from the group consisting of:

a) a nucleotide sequence, or combination thereof, comprising SEQ ID NO:7 and SEQ ID NO: 15;

b) a nucleotide sequence, or combination thereof, comprising SEQ ID NO:23 and SEQ ID NO:31;

c) a nucleotide sequence, or combination thereof, having at least 95% identity to SEQ ID NO:7 and SEQ ID NO:15, wherein the variation is outside of the CDR coding sequences;

d) a nucleotide sequence, or combination thereof, having at least 95% identity to SEQ ID NO:23 and SEQ ID NO:31, wherein the variation is outside of the CDR coding sequences;

e) a fragment of a nucleotide sequence, or combination thereof, comprising at least 80% of the full-length sequence of SEQ ID NO:7 and SEQ ID NO:15, wherein the fragment comprises at least the CDR coding sequences; and f) a fragment of a nucleotide sequence, or combination thereof, comprising at least 80% of the full-length SEQ ID NO:23 and SEQ ID NO:31, wherein the fragment comprises at least the CDR coding sequences.

11. The composition of claim 6, wherein the nucleic acid molecule encoding the CAR comprises a sequence selected from the group consisting of a) a nucleotide sequence selected from the group consisting of SEQ ID NO: 33 and SEQ ID NO:35;

b) a sequence having at least 95% identity to a nucleotide sequence selected from the group consisting of SEQ ID NO:33 and SEQ ID NO:35, wherein the variation is outside of the CDR coding sequences; and c) a fragment comprising at least 80% of the full-length sequence of a nucleotide sequence selected from the group consisting of SEQ ID NO:33 and SEQ ID NO: 35, wherein the fragment comprises at least the CDR coding sequences.

12. The composition of claim 6, further comprising at least one selected from the group consisting of a pharmaceutically acceptable excipient and an adjuvant.

13. The composition of claim 6, comprising an isolated cell comprising the nucleic acid molecule encoding a CAR molecule comprising a domain that specifically binds to Dsg2.

14. The composition of claim 13, wherein the isolated cell comprises an immune cell.

15. The composition of claim 14, wherein the immune cell comprises a natural killer cell.

16. A method of treating a disease or disorder associated with cancer in a subject in need thereof, the method comprising administering a composition of claim 1.

17. A method of treating a disease or disorder associated with cancer in a subject in need thereof, the method comprising administering a composition of claim 6.

18. A method of treating a disease or disorder associated with cancer in a subject in need thereof, the method comprising administering a composition of claim 13.

19. A chimeric antigen receptor comprising a domain that specifically binds to Dsg2, wherein the domain that specifically binds to Dsg2 comprises an antibody or fragment thereof comprising a variable heavy chain sequence comprising the CDR sequences of SEQ ID NO:2, SEQ ID NO:4 and SEQ ID NO:6 and a variable light chain sequence comprising the CDR sequences of SEQ ID NO:10, SEQ ID NO:12 and SEQ ID NO:14.

20. The chimeric antigen receptor of claim 19, wherein the variable heavy chain sequence comprises an amino acid sequence having at least 90% identity to SEQ ID NO: 8, and the variable light chain sequence comprises an amino acid sequence having at least 90% identity to SEQ ID NO: 16.

21. The chimeric antigen receptor of claim 19, wherein the chimeric antigen receptor comprises an amino acid sequence having at least 90% identity to SEQ ID NO: 34.

* * * * *